United States Patent
Li et al.

(10) Patent No.: US 6,469,024 B2
(45) Date of Patent: Oct. 22, 2002

(54) TETRAHYDROISOQUINOLINE ANALOGS USEFUL AS GROWTH HORMONE SECRETAGOGUES

(75) Inventors: James J. Li, Pennington; Joseph A. Tino, Lawrenceville, both of NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/852,565

(22) Filed: May 10, 2001

(65) Prior Publication Data

US 2002/0022637 A1 Feb. 21, 2002

Related U.S. Application Data

(60) Provisional application No. 60/203,335, filed on May 11, 2000.

(51) Int. Cl.[7] ........................ C07D 217/26; A61K 31/47
(52) U.S. Cl. ........................ 514/307; 514/311; 546/139; 546/152
(58) Field of Search ........................ 546/139, 152; 514/307, 311

(56) References Cited

U.S. PATENT DOCUMENTS

| | | |
|---|---|---|
| 5,206,235 A | 4/1993 | Fisher et al. |
| 5,283,241 A | 2/1994 | Bochis et al. |
| 5,284,841 A | 2/1994 | Chu et al. |
| 5,310,737 A | 5/1994 | Fisher et al. |
| 5,317,017 A | 5/1994 | Ok et al. |
| 5,374,721 A | 12/1994 | Schoen et al. |
| 5,430,144 A | 7/1995 | Schoen et al. |
| 5,434,261 A | 7/1995 | Schoen et al. |
| 5,438,136 A | 8/1995 | Devita et al. |
| 5,536,716 A | 7/1996 | Chen et al. |
| 5,545,735 A | 8/1996 | Bochis et al. |
| 5,578,593 A | 11/1996 | Chen et al. |
| 5,583,130 A | 12/1996 | Bochis et al. |
| 5,606,054 A | 2/1997 | Fisher et al. |
| 5,622,973 A | 4/1997 | Morriello et al. |
| 5,652,235 A | 7/1997 | Chen et al. |
| 5,663,171 A | 9/1997 | Chen et al. |
| 5,672,596 A | 9/1997 | Wyratt et al. |
| 5,726,307 A | 3/1998 | Schoen et al. |
| 5,811,402 A | 9/1998 | Klimkowski et al. |

FOREIGN PATENT DOCUMENTS

| | | |
|---|---|---|
| EP | 421 436 | 4/1990 |
| EP | 330 469 | 5/1990 |
| EP | 1113007 | 7/2001 |
| JP | 4099722 | 3/1992 |
| WO | WO93/02679 | 2/1993 |
| WO | WO93/20099 | 11/1993 |
| WO | WO94/19367 | 1/1994 |
| WO | WO95/16675 | 2/1995 |
| WO | WO 95/13069 | 5/1995 |
| WO | WO96/05195 | 2/1996 |
| WO | WO96/22997 | 8/1996 |
| WO | WO97/24369 | 7/1997 |
| WO | WO98/18763 | 5/1998 |
| WO | WO98/58948 | 12/1998 |
| WO | WO00/010975 | 3/2000 |
| WO | WO00/10975 | 3/2000 |
| WO | WO 00/24398 | 5/2000 |
| WO | WO 00/54729 | 9/2000 |
| WO | WO 01-13917 | 3/2001 |

OTHER PUBLICATIONS

Ornstein et al., "6–substituted Decahydroisoquinoline–3–carboxylic Acids as Potent and Selective Conformationally Constrained NMDA Receptor Antagonists", J. Med. Chem., (1992), 35, pp. 3547–3560.

Weisbach et al. "Synthesis and Pharmacology of Some alpha–Oxy–and alpha–Hydroxy–a–enzyltetrahydroisoquinolines", (1968) vol. II, pp. 752–760.

Anderson et al., Synthesis and Murine Antineoplastic Activity of Bis[(carbamoyloxy)methyl] Derivative of Pyrrolo[2,1–a]isoquinoline, J. Med. chem., (1984) 27, pp. 1321–1325.

Primary Examiner—Zinna Northington Davis
(74) Attorney, Agent, or Firm—Ronald S. Hermenau

(57) ABSTRACT

Tetrahydroisoquinoline analogs are provided which are useful in stimulating endogenous production or release of growth hormone and in treating obesity, osteoporosis (improving bone density) and in improving muscle mass and muscle strength.

The tetrahdroisoquinoline analogs thereof have the structure

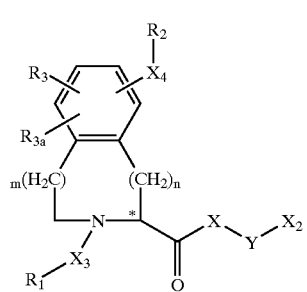

wherein $R_1$, $R_2$, $R_3$, $R_{3a}$, $X_1$, $X_2$, $X_3$, $X_4$, m and n are as described herein.

30 Claims, No Drawings

TETRAHYDROISOQUINOLINE ANALOGS USEFUL AS GROWTH HORMONE SECRETAGOGUES

This application claims priority to U.S. Provisional Application Serial No. 60/203,335 filed May 11, 2000 the entirety of which is incorporated herein by reference.

FIELD OF THE INVENTION

The present invention relates to novel tetrahydroisoquinoline analogs which are growth hormone secretagogues, that is they stimulate endogenous production and/or release of growth hormone, and to methods for treating obesity and diabetes, improving bone density (to treat osteoporosis) and stimulating increase in muscle mass and muscle strength employing such compounds.

BACKGROUND OF THE INVENTION

The pituitary gland secretes growth hormone which stimulates growth in body tissue capable of growing and affects metabolic processes by increasing rate of protein synthesis and decreasing rate of carbohydrate synthesis in cells. Growth hormone also increases mobilization of free fatty acids and use of free fatty acids for energy.

The prior art is replete with patents/applications which disclose compounds which are useful as growth hormone secretagogues.

The following patents/applications, disclose benzofused lactams which are disclosed as being useful in promoting release of growth hormone:

U.S. Pat. Nos. 5,206,235; 5,283,741; 5,284,841; 5,310,737; 5,317,017; 5,374,721; 5,430,144; 5,434,261; 5,438,136; 5,545,735; 5,583,130; 5,606,054; 5,672,596 and 5,726,307; WO 96-05195 and WO 95-16675.

The following patents/applications disclose diverse chemotypes as being useful in promoting release of growth hormone:

U.S. Pat. Nos. 5,536,716; 5,578,593; 5,622,973; 5,652,235; 5,663,171; WO 94-19367; WO 96-22997; WO 97-24369, WO 98-58948 and WO 00-10975.

SUMMARY OF THE INVENTION

In accordance with the present invention, novel tetrahydroisoquinoline analogs are provided which are growth hormone secretagogues and have the structure I

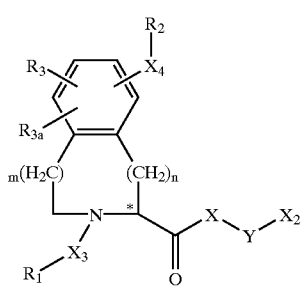

I wherein $R_1$ is alkyl, aryl, alkenyl, alkynyl, arylalkyl, arylalkenyl, cycloalkyl, cycloalkylalkyl, cycloalkylalkoxy, alkoxyalkyl, alkylthioalkyl, aryloxyalkyl, arylalkoxyalkyl, cycloheteroalkyl, cycloheteroalkylalkyl, heteroaryl, or heteroarylalkyl, and where these groups may be optionally substituted with 1 to 3 J1 groups which may be the same or different and the $R_1$ aryls may be further optionally substituted with 1 to 5 halogens, aryl, $-CF_3$, $-OCF_3$, 1-3 hydroxyls, 2 of which substituents where possible, may be joined by a methylene bridge;

$R_2$ is H, alkyl, aryl, alkenyl, alkynyl, arylalkyl, arylalkenyl, cycloalkyl, cycloalkylalkyl, alkoxyalkyl, aryloxyalkyl, arylalkoxyalkyl, cycloheteroalkyl, cycloheteroalkylalkyl, cycloalkylalkoxy, heteroaryl, or heteroarylalkyl, and where these groups may be optionally substituted with a J1a group and the aryls may be further optionally substituted with 1 to 5 halogens, $-CF_3$, $-OCF_3$, or 1-3 hydroxyls;

X is a bond, $-O-$, or $-NR_4-$;

$R_3$ and $R_{3a}$ are the same or different and are independently selected from H, alkoxy, halogen, $-CF_3$, alkyl, or aryl;

$R_4$, $R_{4a}$, $R_{4b}$, $R_{4c}$, $R_{4d}$, $R_{4d}$, $R_{4f}$, $R_{4g}$, $R_{4h}$, $R_{4i}$, $R_{4j}$, $R_{4k}$, and $R_{4l}$ are the same or different and are independently selected from H, $C_1-C_6$ alkyl, or aryl;

m and n are the same or different and are independently 0 or 1;

Y is

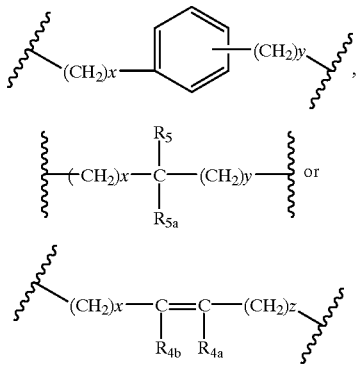

where x and y are the same or different and are independently 0 to 3 and z is 1 to 3;

$R_5$ and $R_{5a}$ are the same or different and are independently H, alkyl, alkoxy, hydroxyl, halogen, $-CF_3$, aryl, alkaryl, and cycloalkyl; or $R_5$ and $R_{5a}$ can be independently joined to one or both of $R_6$ and $R_7$ groups (see $X_2$) to form an alkylene bridge of 1 to 5 carbon atoms; or $R_5$ and $R_{5a}$ can be joined together to form a ring of from 4–7 carbon atoms;

$X_2$ is

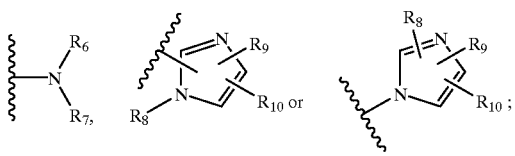

$R_6$ and $R_7$ are the same or different and are independently H or alkyl where the alkyl may be optionally substituted with halogen, 1 to 3 hydroxys, 1 to 3 $C_1-C_{10}$ alkanoyloxy, 1 to 3 $C_1-C_6$ alkoxy, phenyl, phenoxy, or $C_{1-6}$ alkoxycarbonyl; or $R_6$ and $R_7$ can together form $-(CH_2)_tX_5(CH_2)_u-$ where $X_5$ is $-C(R_{4c})(R_{4d})-$, $-O-$ or $-N(R_{4e})-$, t and u are the same or different and are independently 1–3;

$R_8$ is H, $C_1-C_6$ alkyl, $-CF_3$, alkaryl, or aryl, and with the alkyl and aryl groups being optionally substituted with 1 to 3 hydroxys, 1 to 3 $C_1$–$C_{10}$alkanoyloxy, 1 to 3 $C_1$–$C_6$ alkoxy, phenyl, phenoxy or $C_1$–$C_6$alkoxycarbonyl;

$R_9$ and $R_{10}$ are the same or different and are independently H, $C_1$–$C_6$alkyl, —$CF_3$, alkaryl, aryl, or halogen, and with the alkyl and aryl groups being optionally substituted with 1 to 3 hydroxys, 1 to 3 $C_1$–$C_{10}$ alkanoyloxy, 1 to 3 $C_{1-6}$ alkoxy, phenyl, phenoxy or $C_1$–$C_6$ alkoxycarbonyl;

$X_3$ is a bond, —C(O)—, —C(O)O—, —C(O)N($R_{4f}$)-, —S(O)$_2$—, or —S(O)$_2$N($R_{4f}$)-;

$X_4$ is a bond, —O—, —OC(O)—, —N($R_{4g}$)-, —N($R_{4g}$)C(O)—, —N($R_{4g}$)C(O)N($R_{4h}$)—, —N($R_{4g}$)S(O)$_2$—, —N($R_{4g}$)S(O)$_2$N($R_{4h}$), —OC(O)N($R_{4g}$)-, —C(O)—, —C(O)N($_{4g}$)—, —S—, —S(O)$_2$—, or —S(O)$_2$N($R_{4g}$)-;

J1 and J1a are the same or different and are independently nitro, halogen, hydroxyl, —$OCF_3$, —$CF_3$, alkyl, —$(CH_2)_v$CN, —$(CH_2)_v$N($T_{1a}$)C(O)$T_1$, —$(CH_2)_v$N($T_{1a}$)C(O)O$T_1$, —$(CH_2)_v$N($T_{1a}$)C(O)N($T_{1a}$)$T_1$, —$(CH_2)_v$N$T_1$($T_{1a}$), —$(CH_2)_v$N($T_{1a}$)SO$_2$$T_1$, —$(CH_2)_v$C(O)N($T_{1a}$)$T_1$, —$(CH_2)_v$C(O)O$T_1$, —$(CH_2)_v$OC(O)O$T_1$, —$(CH_2)_v$OC(O)$T_1$, —$(CH_2)_v$OC(O)O$T_1$, —$(CH_2)_v$OC(O)$T_1$, —$(CH_2)_v$OC(O)N($T_{1a}$)$T_1$, —$(CH_2)_v$N($T_{1a}$)SO$_2$N($T_{1b}$)$T_1$, —$(CH_2)_v$O$T_1$, —$(CH_2)_v$SO$_2$$T_1$, —$(CH_2)_v$SO$_2$N($T_{1a}$)$T_1$, —$(CH_2)_v$C(O)$T_1$, —$(CH_2)_v$CH(OH)$T_1$, or heteroaryl as defined below, with v being 0–3;

$T_1$, $T_{1a}$ and $T_{1b}$ are the same or different and are independently H, alkyl, alkenyl, alkynyl, lower alkythioalkyl, alkoxyalkyl, aryl, arylalkyl, heteroaryl, heteroarylalkyl, cycloheteroalkyl, or cycloalkyl, each of which may be optionally substituted with halogen, hydroxyl, —C(O)NR$_{4i}$R$_{4j}$, —NR$_{4i}$C(O)R$_{4j}$, —CN, —N(R$_{4i}$)SO$_2$R$_{11}$, —OC(O)R$_{4i}$, —SO$_2$ NR$_{4i}$R$_{4j}$, —SOR$_{11}$, —SO$_2$R$_{11}$, alkoxy, —COOH, cycloheteroalkyl, or —C(O)OR$_{11}$; with the proviso that $T_1$ cannot be hydrogen when it is connected to sulfur, as in SO$_2$T$_1$; or $T_1$ and $T_{1a}$ or $T_1$ and $T_{1b}$ can together form —$(CH_2)_r$X$_{5a}$(CH$_2$)$_s$— where $X_{5a}$ is —C(R$_{4k}$)(R$_{4l}$)-, —O— or —N(R$_{4k}$)-, r and s are the same or different and are independently 1–3;

$R_{11}$ is $C_1$–$C_6$alkyl or aryl;

or a pharmaceutically acceptable salt thereof, or a prodrug ester thereof, and including all stereoisomers thereof;

(1) with the proviso that where m is 0 and n is 1, the moiety -$X_4$-$R_2$ is other than alkyl or alkoxy and (2) where X is a bond and $X_2$ is amino, then m is 1.

Thus, the compounds of formula I of the invention include compounds of the following structures.

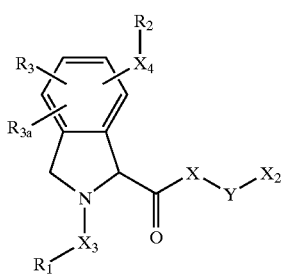

IA (where m is 0 and n is 0)

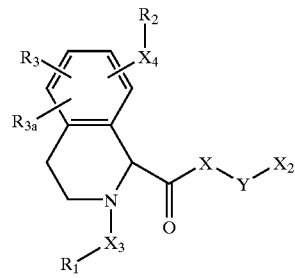

IB (where m is 1 and n is o)

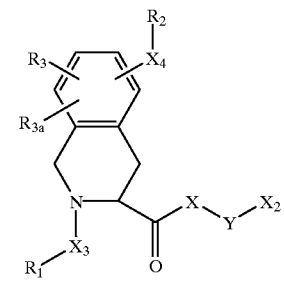

IC (where m is 0 and n is 1)

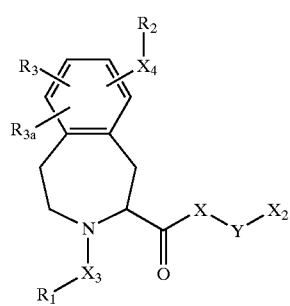

ID (where m is 1 and n is 1)

The compounds of the instant invention all have at least one asymmetric center as noted by the asterisk in structural formula I. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. The racemic mixtures may be separated into individual optical isomers employing conventional procedures such as by chromatography or fractional crystallization. In the case of the asymmetric center represented by the asterisk in formula I, it has been found that compounds with either the R or S configuration are of almost equal activity. Therefore one isomer might be only slightly preferred, therefore both are claimed.

The pharmaceutically acceptable salts of the compounds of formula I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In addition, in accordance with the present invention, a method for increasing levels of endogenous growth hormone or increasing the endogenous production or release of growth hormone is provided wherein a compound of formula I as defined hereinbefore is administered in a therapeutically effective amount.

Furthermore, in accordance with the present invention, a method is provided for preventing or treating osteoporosis (improving bone density and/or strength), or treating obesity, or increasing muscle mass and/or muscle strength, or maintenance of muscle strength and function in elderly humans, or reversal or prevention of fraility in elderly humans, wherein a compound of formula I as defined hereinbefore is administered in a therapeutically effective amount.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 3 substituents including alkyl, aryl, alkenyl, alkynyl, hydroxy, arylalkyl, cycloalkyl, cycloalkylalkyl, alkoxy, arylalkyloxy, alkanoyl, amino, haloaryl, $CF_3$, $OCF_3$, aryloxy, heteroaryl, cycloalkylalkoxyalkyl, or cycloheteroalkyl.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, cyclohexenyl,

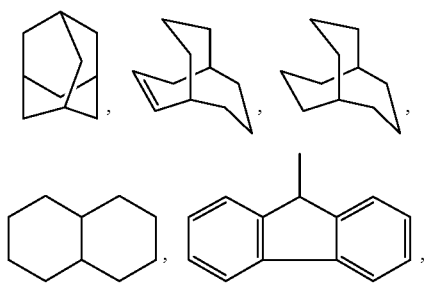

-continued

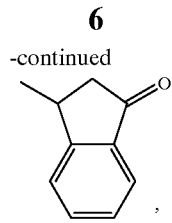

any of which groups may be optionally substituted with 1 to 3 substituents as defined above for alkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or cycloheteroalkyl rings) and may be optionally substituted through available carbon atoms with 1 to 5 halo, 1, 2, or 3 groups selected from hydrogen, haloalkyl, alkyl, haloalkyl, alkoxy, haloalkoxy, alkenyl, trifluoromethyl, trifluoromethoxy, alkynyl, cycloalkylalkyl, fluorenyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or preferably any of the aryl substituents as set out above.

Preferred aryl groups include phenyl, biphenyl or naphthyl.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxyl", "alkoxyl", "aryloxyl" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", "alkylthio", "alkylthioalkyl", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 2 to 6 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the substituents for alkyl as set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the substituents for alkyl as set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Examples of $(CH_2)_m$, $(CH_2)_n$, $(CH_2)_p$, $(CH_2)_r$, $(CH_2)_s$, $(CH_2)_t$, $CH_2)_u$, $(CH_2)_v$, $(CH_2)_x$, $(CH_2)_y$, $(CH_2)_z$, and other groups (which may include alkylene, alkenylene or alkynylene groups as defined herein, and may optionally include 1, 2, or 3 substituents which may be any of the substituents for alkyl set out herein), are as follows:

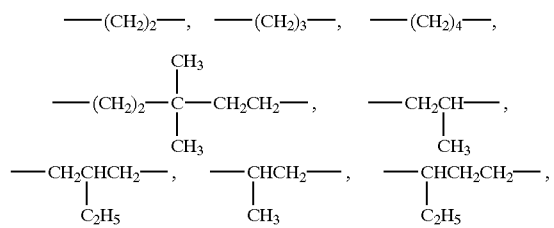

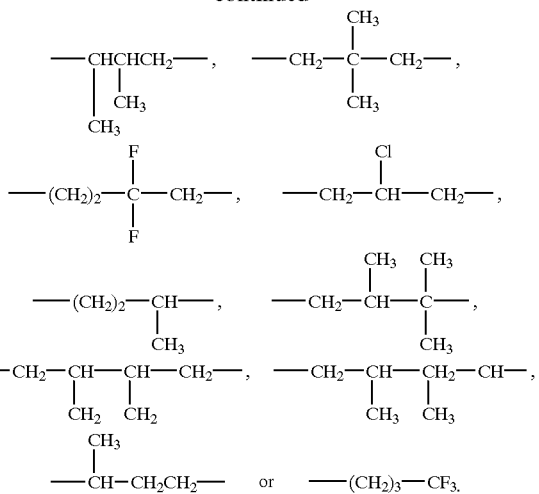

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocyclic", "heterocyclo" or "heterocycle" as employed herein alone or as part of another group refers to "heteroaryl" groups or "cycloheteroalkyl" groups.

The term "cycloheteroalkyl" as used herein alone or as part of another group refers to a 4-, 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

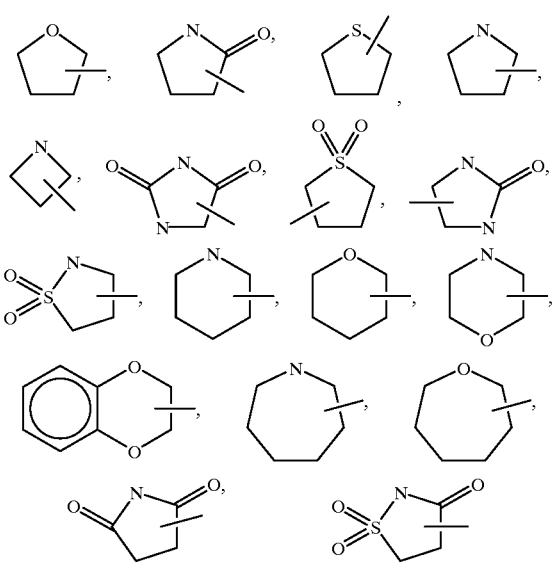

and the like. The above groups may include 1 to 4 substituents such as alkyl, halo, oxo and/or any of of the aryl substituents set out herein. In addition, any of the above rings can be fused to a cycloalkyl, aryl, heteroaryl or cycloheteroalkyl ring.

The term "heteroaryl" as used herein alone or as part of another group refers to a 5- or 6- membered aromatic ring which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides, such as and the like.

The heteroaryl groups may optionally include 1 to 4 substituents such as any of the aryl substituents set out herein as well as carbonyl and arylcarbonyl. In addition, any of the above rings can be fused to a cycloalkyl, aryl, heteroaryl or cycloheteroalkyl ring.

Preferred are compounds of formula IB wherein $R_1$ is alkyl, aryl, arylalkyl, cycloalkyl, cycloalkylalkyl, alkoxyalkyl, aryloxyalkyl, heteroaryl, or heteroarylalkyl, and where these groups may be further optionally substituted with a J1 group;

$R_2$ is alkyl, aryl, arylalkyl, alkoxyalkyl, aryloxyalkyl, heteroaryl, cycloalkyl, cycloalkylalkyl, or heteroarylalkyl, and these groups may be further optionally substituted by J1a;

X is —O— or —N-$R_4$;

$R_3$ and $R_{3a}$ are the same or different and are independently H, alkoxy, halogen, —CF3;

$R_4$ is H or $C_1$-$C_6$ alkyl;

m and n are independently 0 or 1;

Y is or

-continued where x and y are independently 0 to 3;

$R_5$ and $R_{5a}$ are the same or different and are independently H, alkyl, —$CF_3$, or $R_5$ and $R_{5a}$ can be independently joined to one or both of $R_6$ and $R_7$ groups (see $X_2$) to form an alkylene bridge of 1 to 5 carbon atoms;

$X_2$ is $R_6$ and $R_7$ are the same or different and are independently H or alkyl, where alkyl can optionally be substituted with halogen, 1 or 2 hydroxyls, 1 or 2 $C_1$-$C_{10}$ alkanoyloxy, 1 or 2 $C_1$-$C_6$ alkoxy, phenyl, phenoxy, $C_1$-$C_6$ alkoxycarbonyl; or $R_6$ and $R_7$ can together form —$(CH_2)_t X_5 (CH_2)_u$— where $X_5$ is $C(R_4)$ $(R_{4a})$ or O, t and u are independently 1–3;

$X_3$ is —C(O)—, —C(O)O—, or —S(O)$_2$N ($R_4$)

$X_4$ is a bond, —O—, —OC(O)—, or —N($R_4$)C(O)—;

J1 is —$(CH_2)_v$CN, —$(CH_2)_v$N$(T_{1a})$C(O)$T_1$, —$(CH_2)_v$N $(T_{1a})$C(O)O$T_1$, —$(CH_2)_v$N$(T_{1a})$C(O)N$(T_{1b})T_1$, —$(CH_2)_v$SO$_2T_1$, —$(CH_2)_v$N$(T_{1a})$SO$_2T_1$, —$(CH_2)_v$C(O)N$(T_{1a})T_1$, —$(CH_2)_v$C(O)O$T_1$, —$(CH_2)_v$OC(O)$T_1$, —$(CH_2)_v$OC(O)N$(T_{1a})T_1$, —$(CH_2)_v$N$(T_{1a})$SO$_2$N$(T_{1b})$ $T_1$, —$(CH_2)_v$O$T_1$, —$(CH_2)_v$SO$_2$N$(T_{1a})T_1$, —$(CH_2)_v$C(O)$T_1$, or heteroaryl, with v being 0–2;

J1a is halogen, —$(CH_2)_v$CN, —$(CH_2)_v$N$(T_{1a})$C(O)$T_1$, —$(CH_2)_v$C(O)N$(T_{1a})T_1$, —$(CH_2)_v$C(O)O$T_1$, —$(CH_2)_v$O$T_1$, or —$(CH_2)_v$C(O)$T_1$, with v being 0–2;

$T_1$, $T_{1a}$ and $T_{1b}$ are the same or different and are independently H, alkyl, aryl, alkaryl, or cycloalkyl; each optionally substituted with halogen, hydroxyl or alkoxy; with the proviso that $T_1$ cannot be hydrogen when it is connected to sulfur as in SO$_2T_1$;

Most preferred are compounds of the formula IB, wherein $R_1$ is alkyl, aryl, arylakyl, cycloalkyl, and cycloalkylalkyl and where these groups may be further optionally substituted with a J1 group;

$R_2$ is alkyl, aryl, arylalkyl, or cycloalkyl, and these groups may be further optionally substituted by J1a;

X is —NH or —NCH$_3$;

$R_3$ and $R_{3a}$ are each H;

m is 1;

n is 0;

Y is where x and y are independently 0 or 1, with the proviso that both cannot be 0;

$R_5$ and $R_{5a}$ are the same or different and are independently H, alkyl, —$CF_3$; or $R_5$ and $R_{5a}$ can be independently joined to one or both of $R_6$ and $R_7$ groups (see $X_2$) to form an alkylene bridge of 1 to 5 carbon atoms;

$X_2$ is

$R_6$ and $R_7$ are the same or different and are independently H or alkyl where alkyl may be optionally substituted with halogen, or 1 to 2 hydroxyls;

$X_3$ is —C(O)—, —C(O)O—, or —S(O)$_2$N(R$_{4f}$);

$X_4$ is —O—, or —OC(O)—;

J1 is —(CH$_2$)vCN, —(CH$_2$)vN(T$_{1a}$)C(O)T$_1$, —(CH$_2$)$_v$N(T$_{1a}$)C(O)OT$_1$, —(CH$_2$)$_v$N(T$_{1a}$)C(O)N(T$_{1b}$)T$_1$, —(CH$_2$)$_v$SO$_2$T$_1$, —(CH$_2$)$_v$N(T$_{1a}$)SO$_2$T$_1$, —(CH$_2$)$_v$C(O)N(T$_{1a}$)T$_1$, —(CH$_2$)$_v$C(O)OT$_1$, —(CH$_2$)$_v$OC(O)T$_1$, —(CH$_2$)$_v$OC(O)N(T$_{1a}$)T$_1$, —(CH$_2$)$_v$N(T$_{1a}$)SO$_2$N(T$_{1b}$)T$_1$, —(CH$_2$)$_v$OT$_1$, —(CH$_2$)$_v$SO$_2$N(T$_{1a}$)T$_1$, —(CH$_2$)$_v$C(O)T$_1$, or heteroaryl, with v being 0–2;

J1a is halogen, —(CH$_2$)$_v$CN, —(CH$_2$)$_v$N(T$_{1a}$)C(O)T$_1$, —(CH$_2$)$_v$C(O)N(T$_{1a}$)T$_1$, —(CH$_2$)$_v$C(O)OT$_1$, —(CH$_2$)$_v$OT$_1$, or —(CH$_2$)$_v$C(O)T$_1$, with v being 0–2;

$T_1$, $T_{1a}$ and $T_{1b}$ are the same or different and are independently H, alkyl, aryl or alkaryl, each optionally substituted with halogen, hydroxyl or alkoxy; with the proviso that $T_1$ cannot be hydrogen when it is connected to carbonyl or sulfur, as in C(O)T$_1$ or SO$_2$T$_1$;

Examples of preferred compounds of the invention include the following:

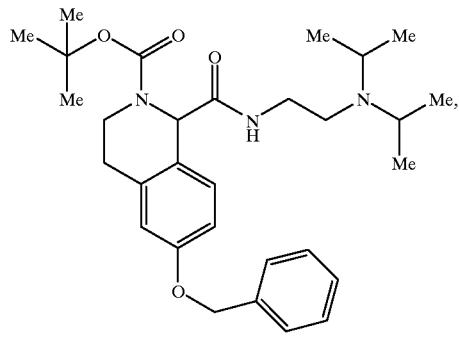

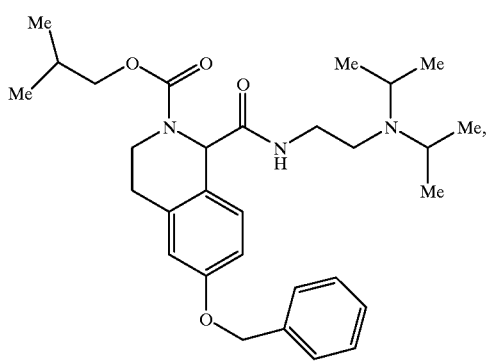

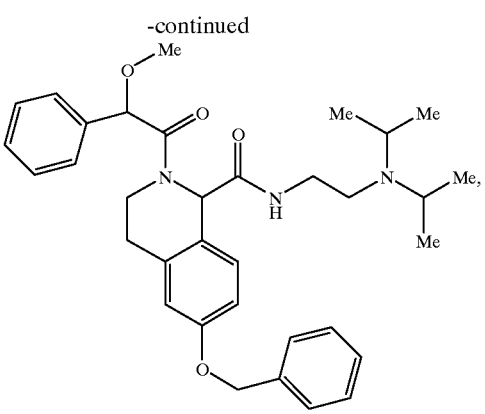

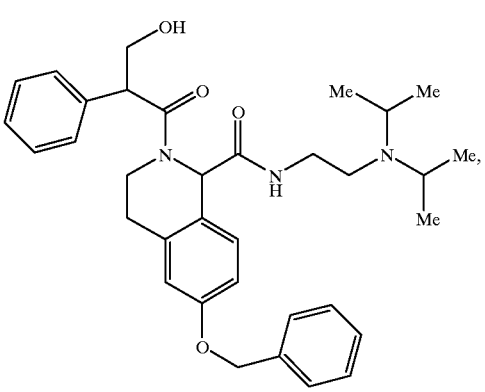

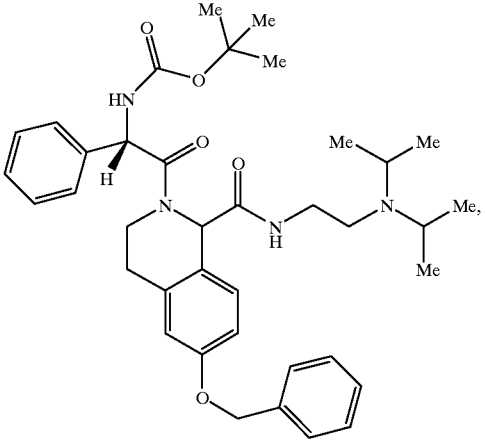

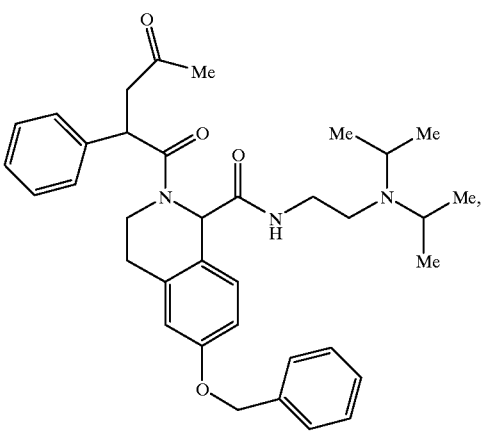

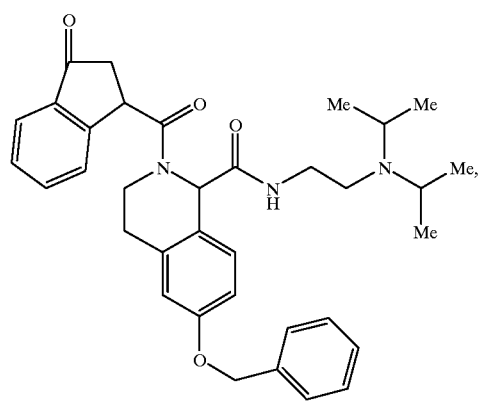
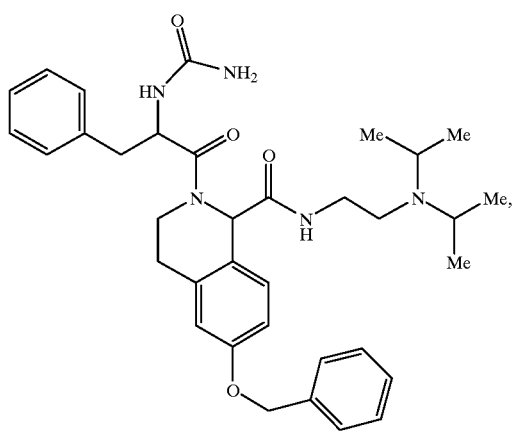
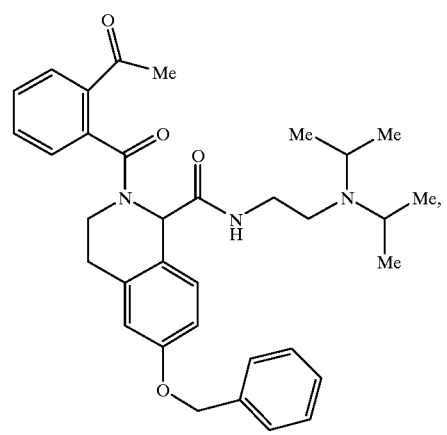
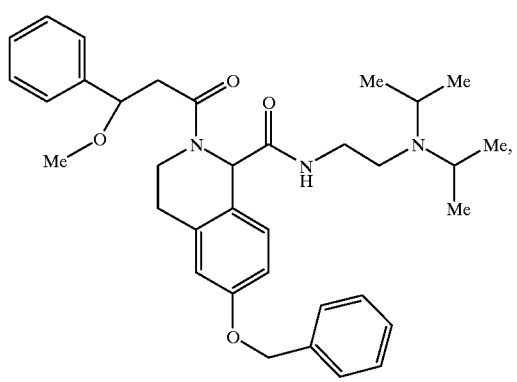
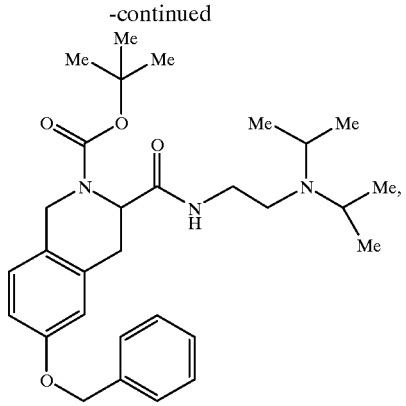
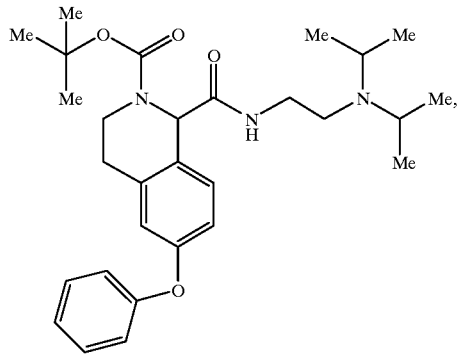
racemic
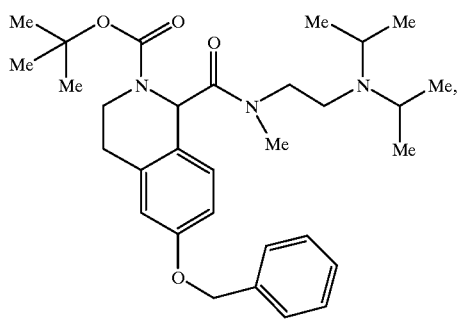
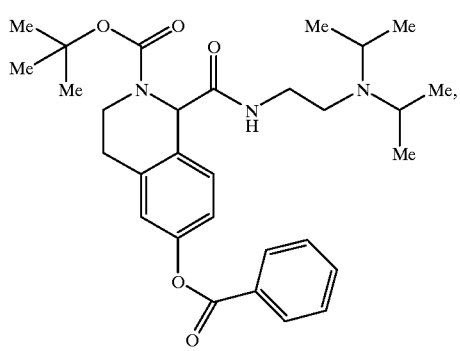

-continued
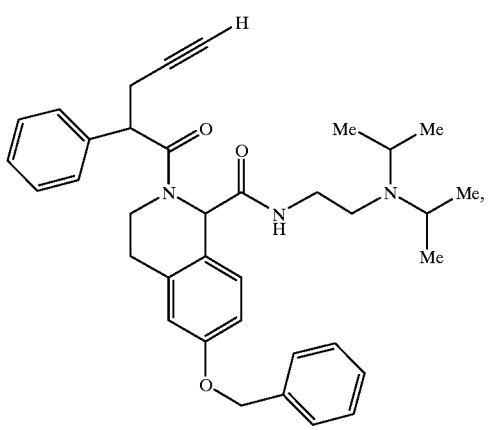
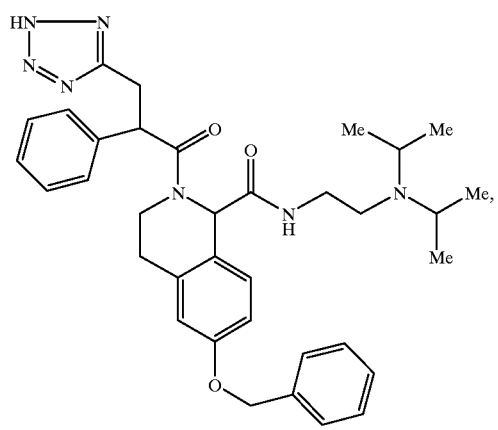
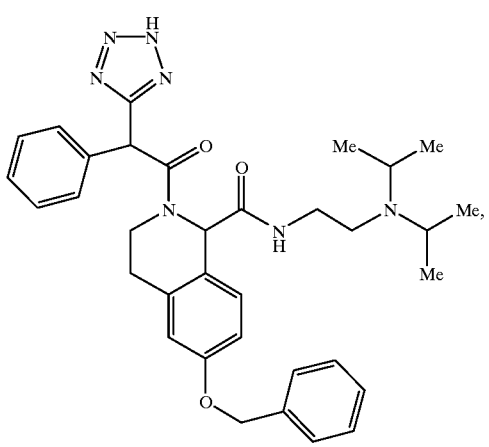
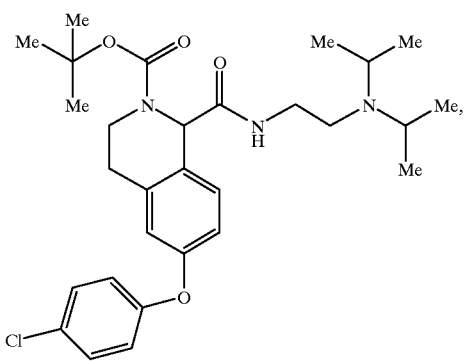
-continued
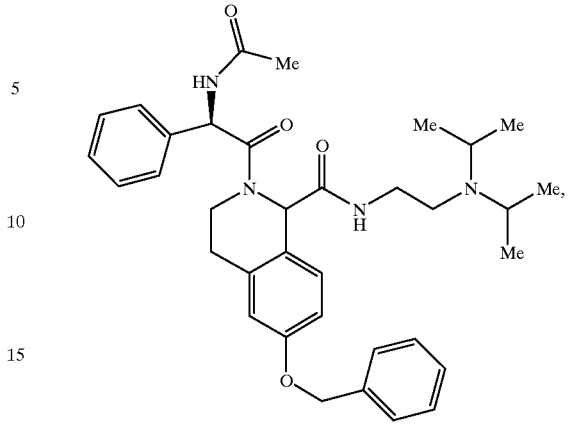
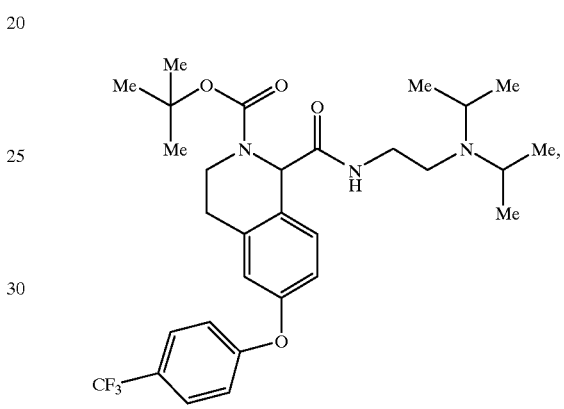
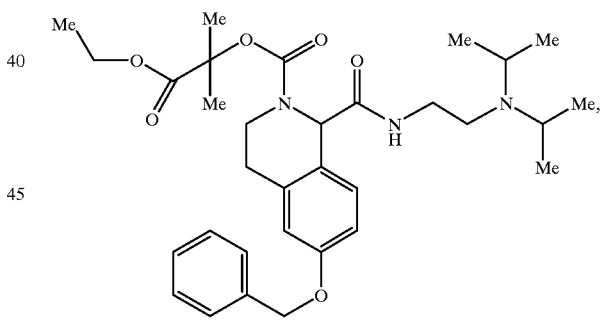
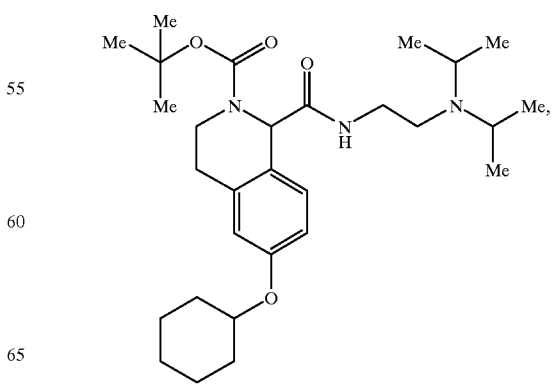

-continued
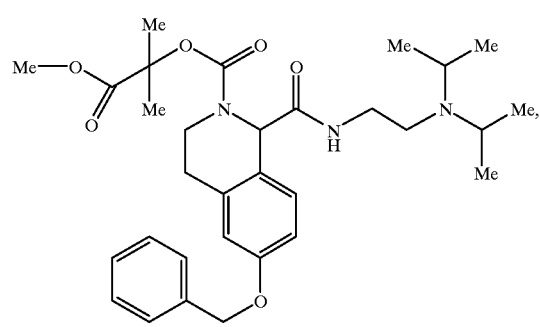
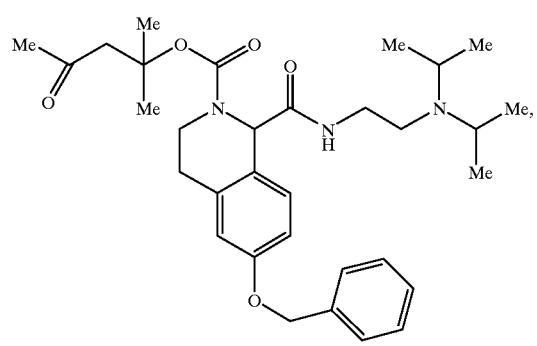
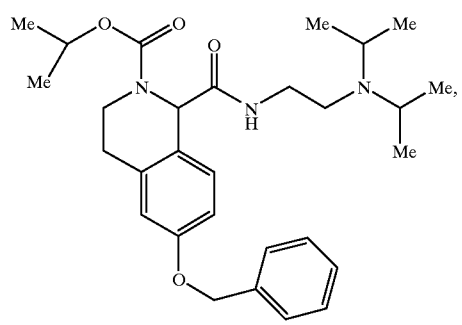
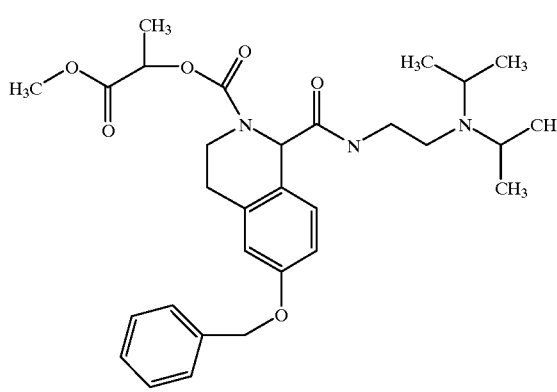
-continued
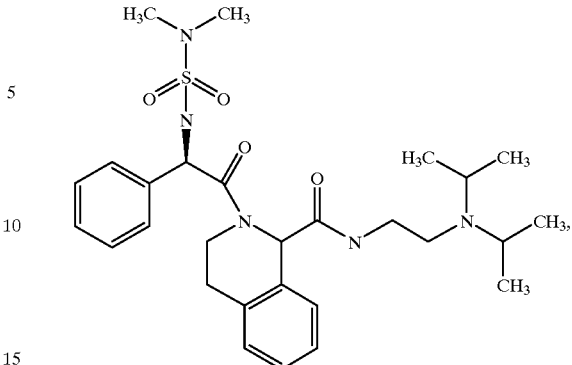
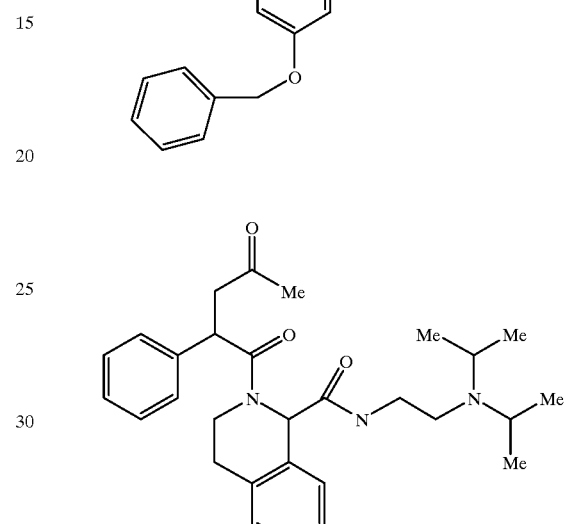
Diastereomer A
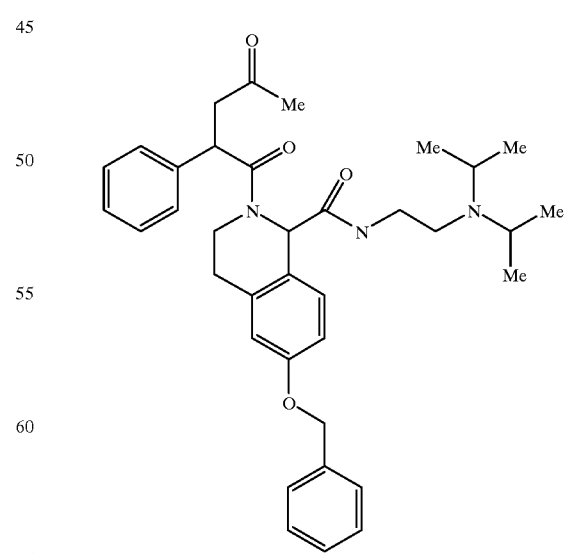
Diastereomer A

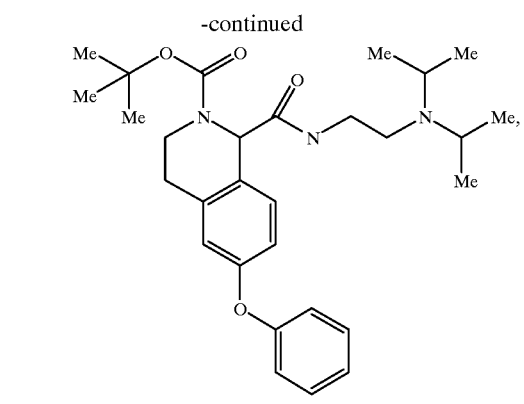
Isomer A
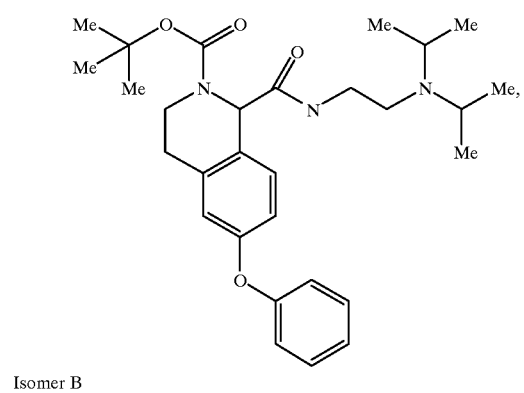
Isomer B
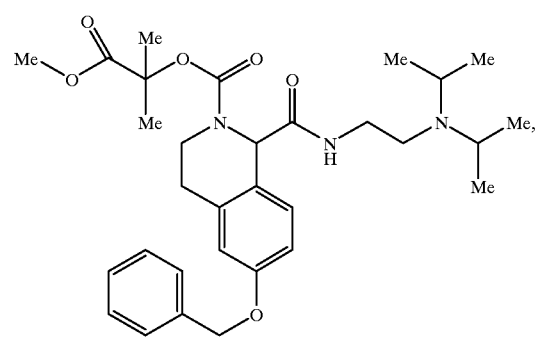
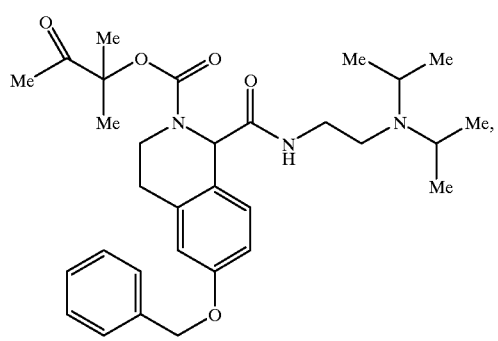
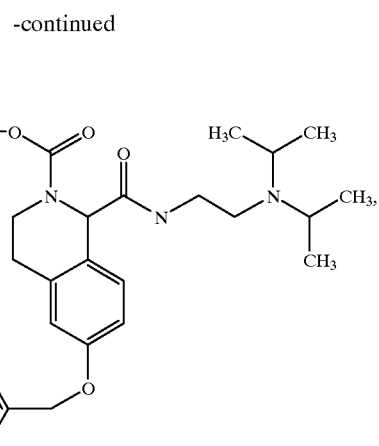
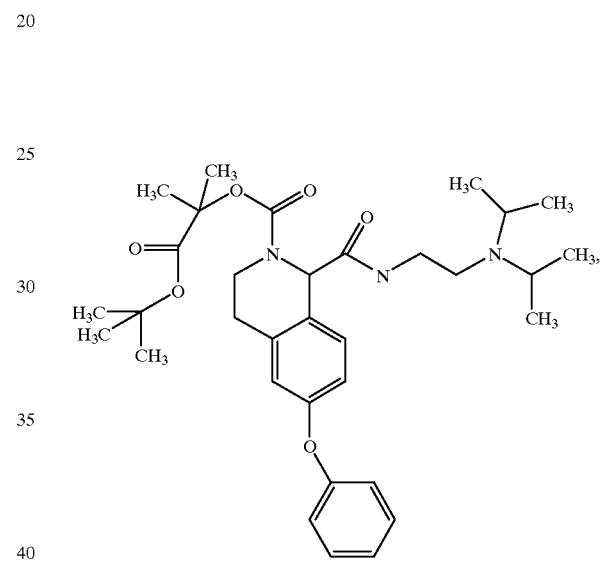
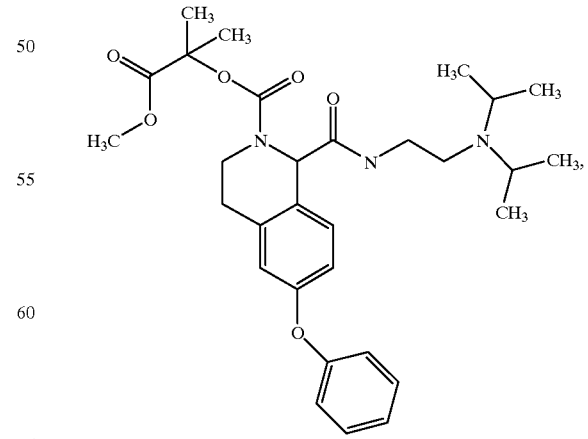
Isomer A

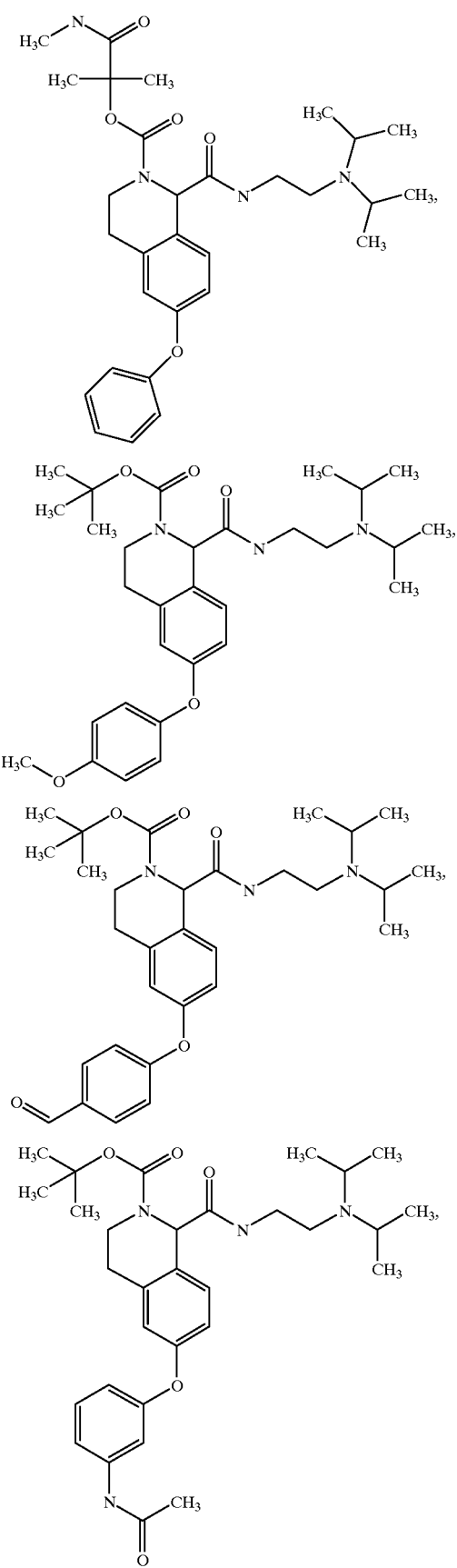
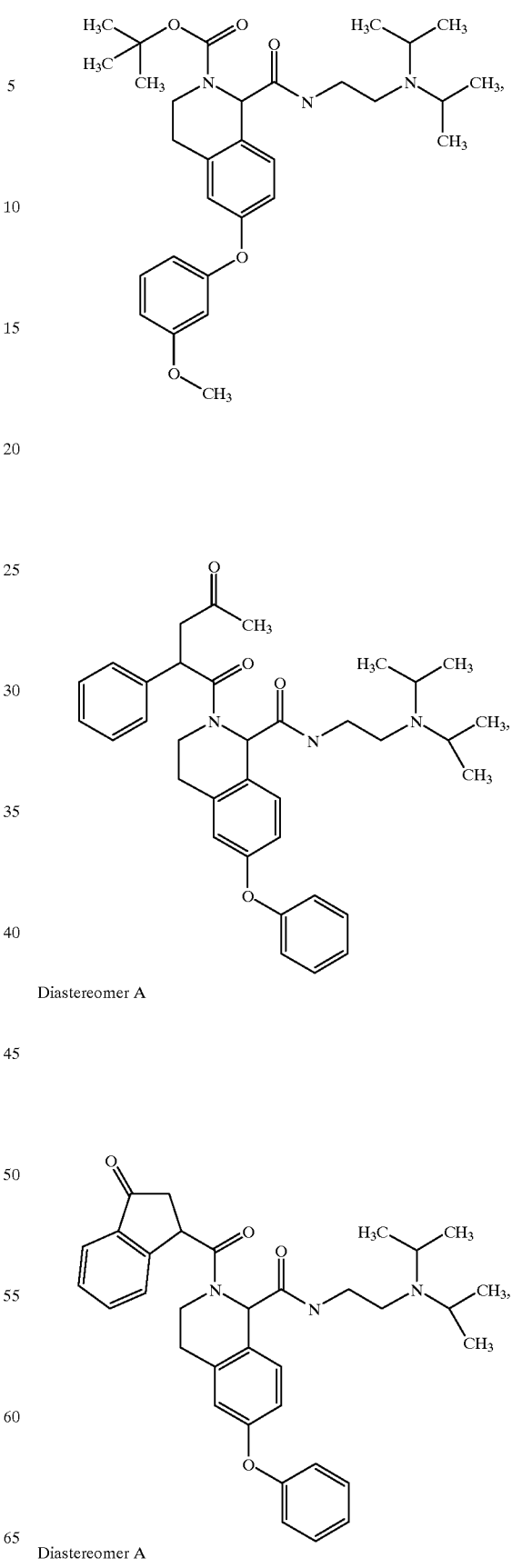
Diastereomer A
Diastereomer A

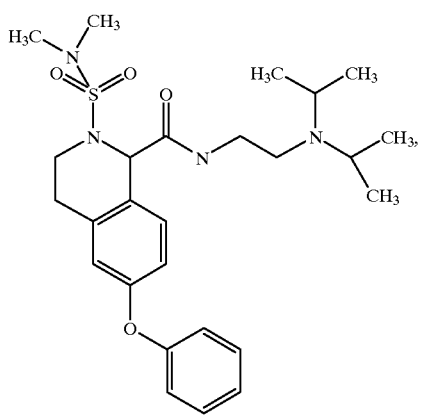
Isomer A
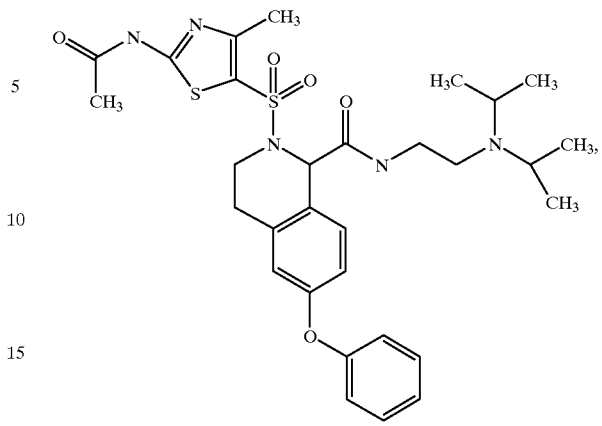
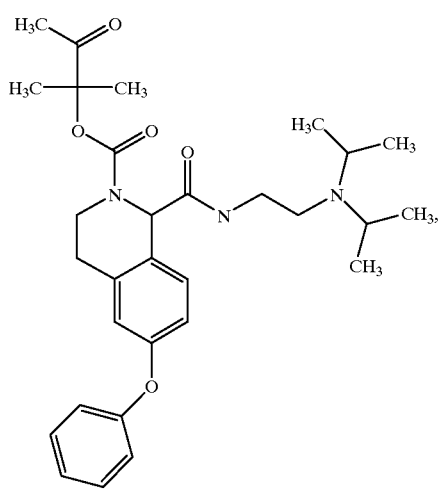
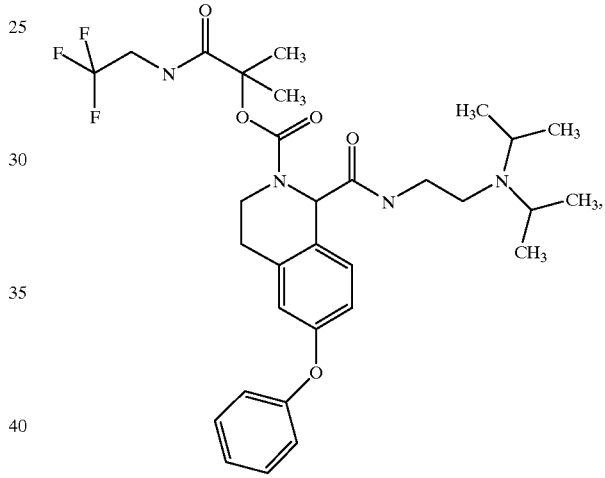
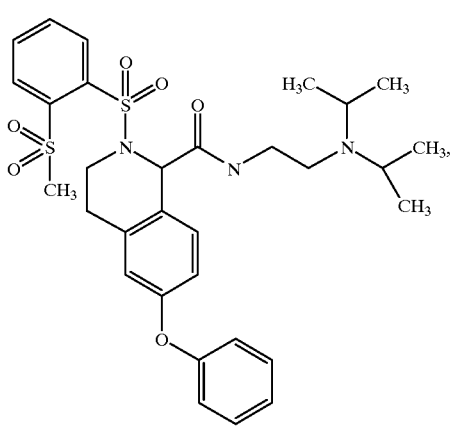
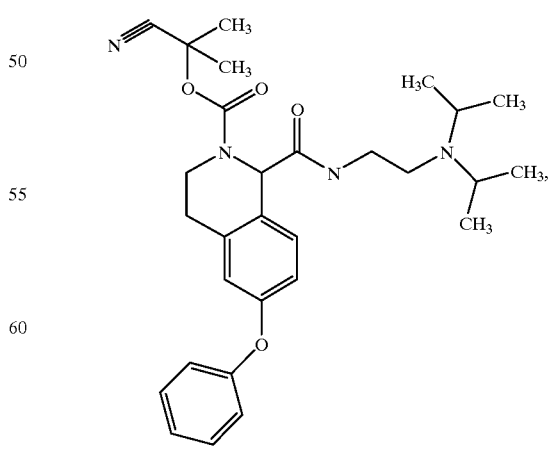

-continued

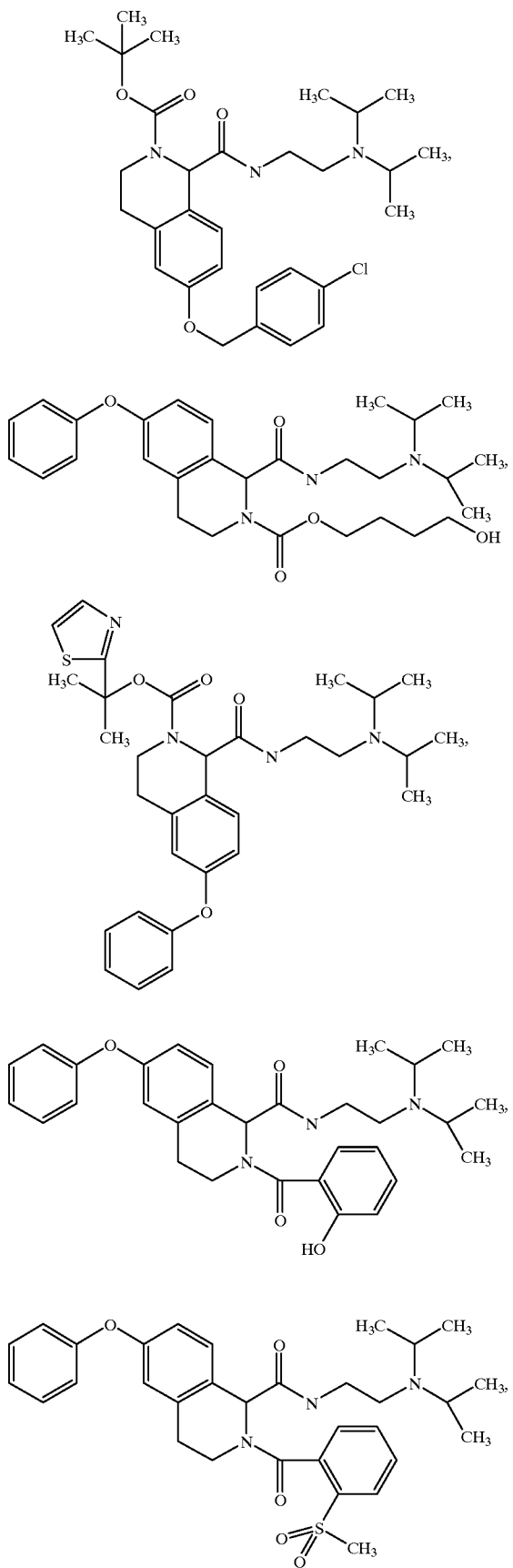
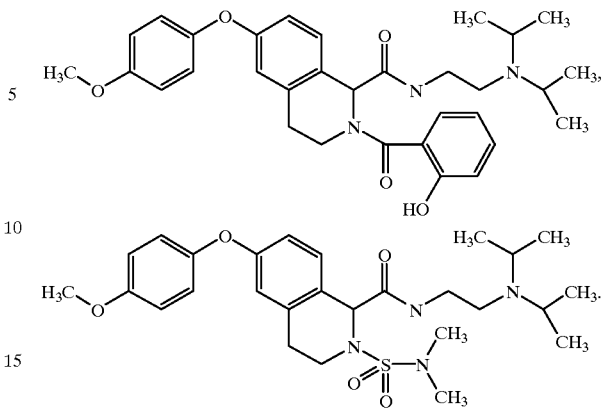

General Synthetic Schemes

The compounds of the present invention may be prepared according to the following general synthetic schemes, as well as relevant published literature procedures that are used by one skilled in the art. Exemplary reagents and procedures for these reactions appear hereinafter and in the working Examples. Unless otherwise specified, the various substituents of the compounds are defined in the same manner as the formula I compound of the invention.

With respect to the following reaction schemes, amide bond forming reactions are conducted under standard peptide coupling procedures know in the art. Optimally, the reaction is conducted in a solvent such as DMF at 0° C. to room temperature using EDAC (WSC) (1-ethyl-3-(dimethyl- aminopropyl) carbodiimide), HOBt(1-hydroxybenzotriazole) or HOAt (1-hydroxy-7-azabenzotriazole) and a base (Hunigs base). Carbamates of formula IE can be formed under standard conditions known in the art from chloroformates, the piperidine amine and a base.

Tetrahydroisoquinolines can be formed as shown in Scheme 1. Suitable cyclization procedures are described in *J. Med. Chem.*, 87, 1821–1825 (1984), *Tet. Lett*, 21, 4819 (1980), *Synthesis*, 824 (1987). Alternative examples are shown in Scheme 8 (*J. Org. Chem.*, 61, 8103–8112 (1996); *Tetrahedron*, 43, 5095 (1987)), Scheme 9 (*Syn. Com.* 23, 473–486 (1993); *J Chem. Soc., Perkin Trans* 1, 2497 (1996); *Tet. Lett.*, 37, 5329 (1996)), and Scheme 10 (*Tetrahedron*, 50, 6193 (1994); *Tet. Lett.*, 34, 5747–5750 (1993); *J Chem Soc, Chem Commun*, 11, 966 (1993)) and Scheme 11. The intermediate A in Scheme 8 can be prepared by suitable methods known in the art, such as in *Tet. Lett*, 37, 5453 (1996) and *Synthesis*, 824 (1987). The protecting group Pc in Scheme 8 can be chiral (formamidine activation Meyers, A. I., *J. Org. Chem.*, 61, 8103–8112 (1990)), imparting chirality to compounds 48–50. The synthesis outlined in Scheme 10 can also lead to chiral induction in intermediates 66–71. Intermediates 49, 50, 61, 71 and 78 in Schemes 8 to 11 can be further transformed by methods disclosed in Schemes 1–7.

Protection and deprotection in the Schemes below may be carried out by procedures generally known in the art. See, for example, T. W. Greene, Protecting Groups in Organic Synthesis, Second Edition, 1991. P in the Schemes below denotes a nitrogen protecting group, optimally BOC or Cbz. The BOC group can be removed under acidic conditions, optimally HCl or trifluoroacetic acid. The Cbz group can be removed via hydrogenolysis, optimally using a palladium catalyst and hydrogen, or using TMSI. P1 in the Schemes below denotes a phenol protecting group such as BOC (removed by acid or base hydrolysis) or benzyl (removed by hydrogenolysis or TMSI).

Phenol intermediates shown in the General Schemes below may be acylated by methods known in the art to prepare esters and carbamates. The same phenol intermediates may be transformed into anilines by methods known in the art, such as Rossi, *J Org Chem,* 37 (1972). The anilines may be acylated by methods known in the art to prepare amides, ureas, and other derivatives covered by X4. The same phenol intermediates can be transformed to acids, esters or amides through an activated intermediate, such as triflate, by methods known in the art; phenol to acid: Jutand *J Chem Soc.,* 23, 1729–1730 (1992), Wang *Tet. Lett.,* 37, 6661–6664 (1996); to esters: Fretz *Tet. Lett.,* 37, 8475–8478 (1996), Horikawa *Heterocycles,* 40, 1009–1014 (1995) ; to amides: Cacchi *Tet. Lett.,* 27, 3931 (1986); to sulfides: Arould *Tet. Lett.,* 37, 4523–4524 (1996), Percec *J Org Chem,* 60, 6895–6903 (1995), Meier *Angew Chem,* 106, 493–495 (1994), Wong *J Med Chem,* 27, 20 (1984). The resulting sulfides can be oxidized to sulfones and sulfoxides by standard methods known in the art, such as meta-chloroperoxybenzoic acid.

The arylation reaction covered in Scheme 2 can be performed under the coupling conditions in the literature described in Evans et al, *Tet Lett,* 39, 2937–2940 (1998).

Please note that in the following Schemes 1–10 the compounds of formula IB (m=1 and n=0) are shown. However, the schemes are also applicable in preparing all compounds of the formula I invention including compounds of formulae IA, IC and ID of the invention employing reagents or starting materials analogous to those shown in the schemes as will be apparent to one skilled in the art. In the following schemes $R_2$ is other than hydrogen.

General Scheme 1: Carbamates

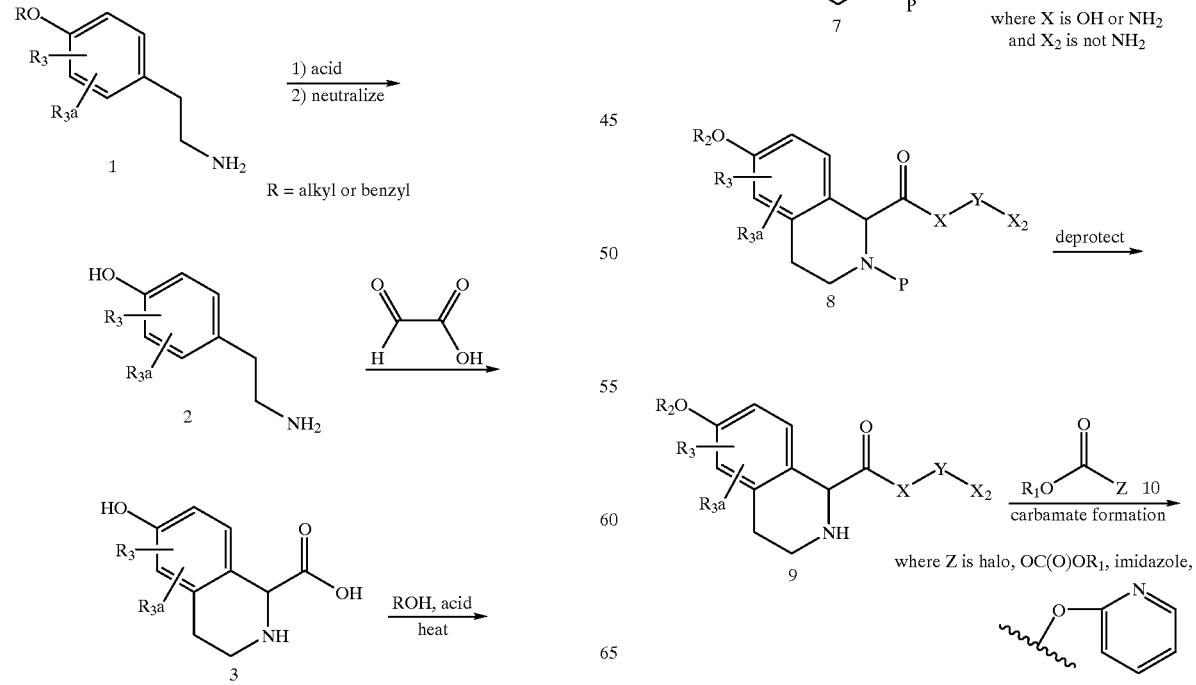
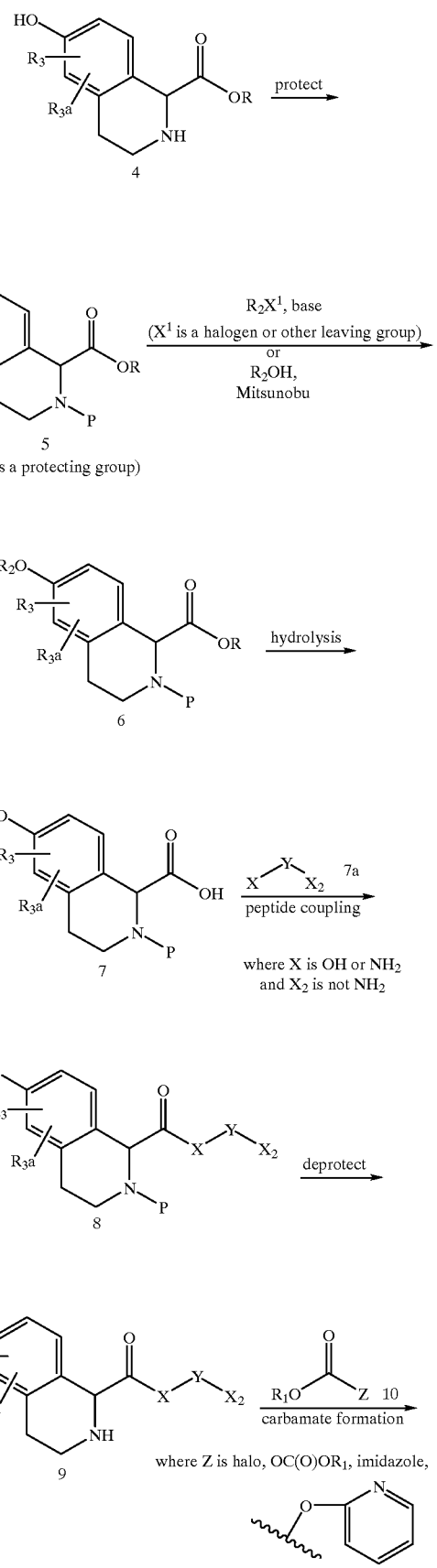

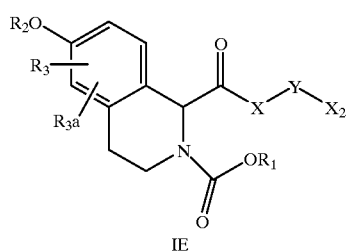
IE
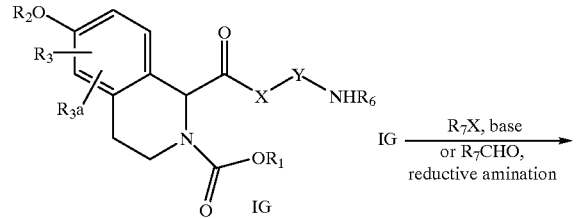
General Scheme 1 alternate: Carbamates
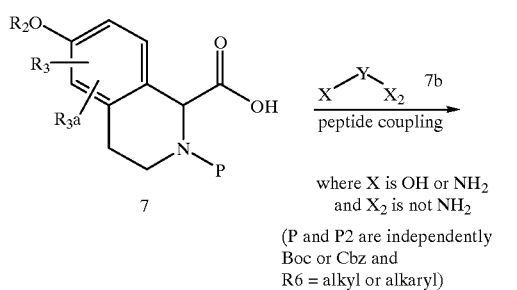
where X is OH or NH$_2$
and X$_2$ is not NH$_2$
(P and P2 are independently
Boc or Cbz and
R6 = alkyl or alkaryl)
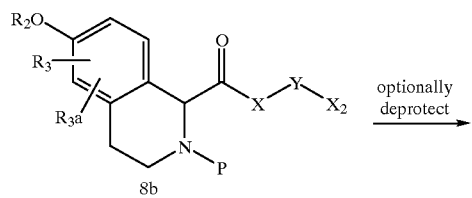
8b
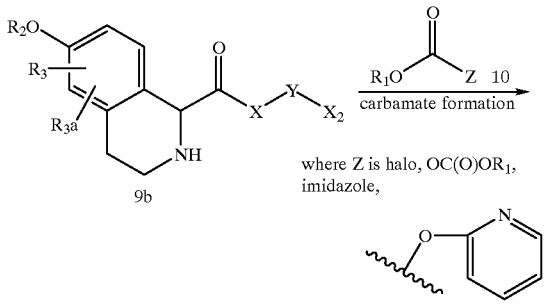
9b
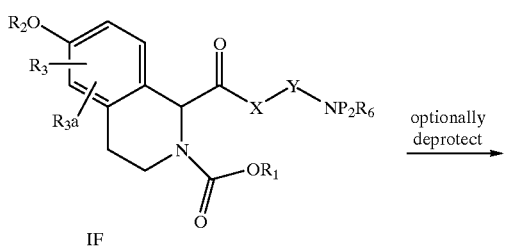
IF
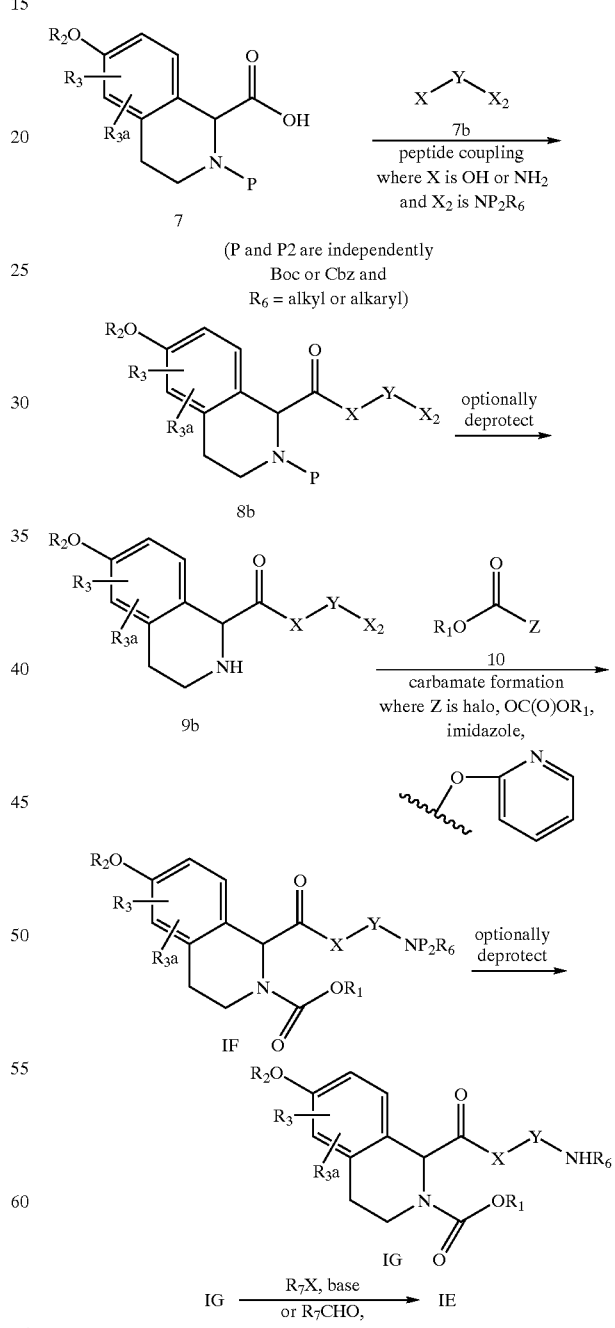

General Scheme 1a: Ureas
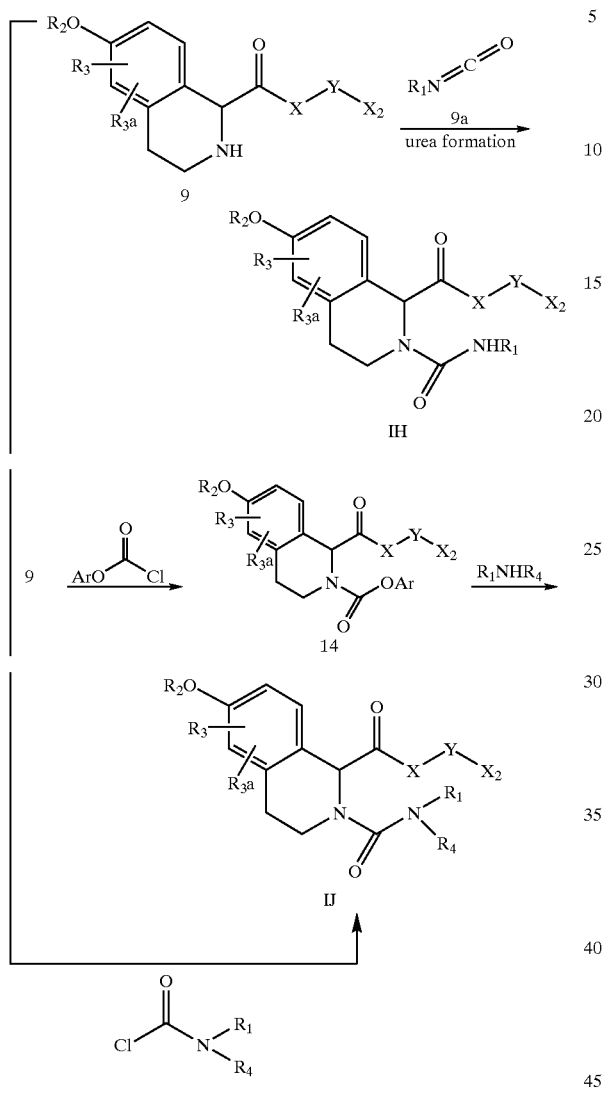
General Scheme 1b: Amides
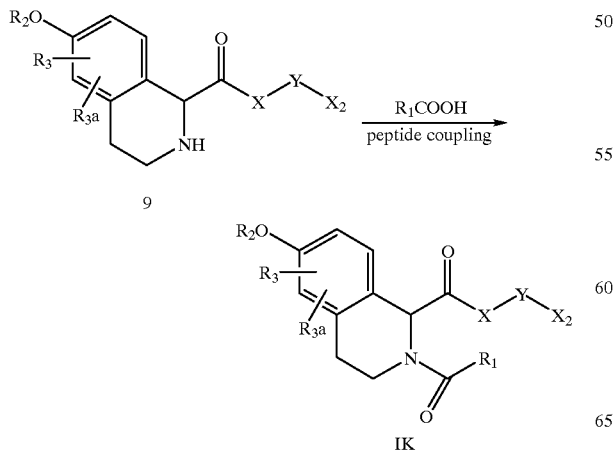
-continued
9 →[R₁C(O)Cl / base] IK
General Scheme 1c: SulfonylUreas
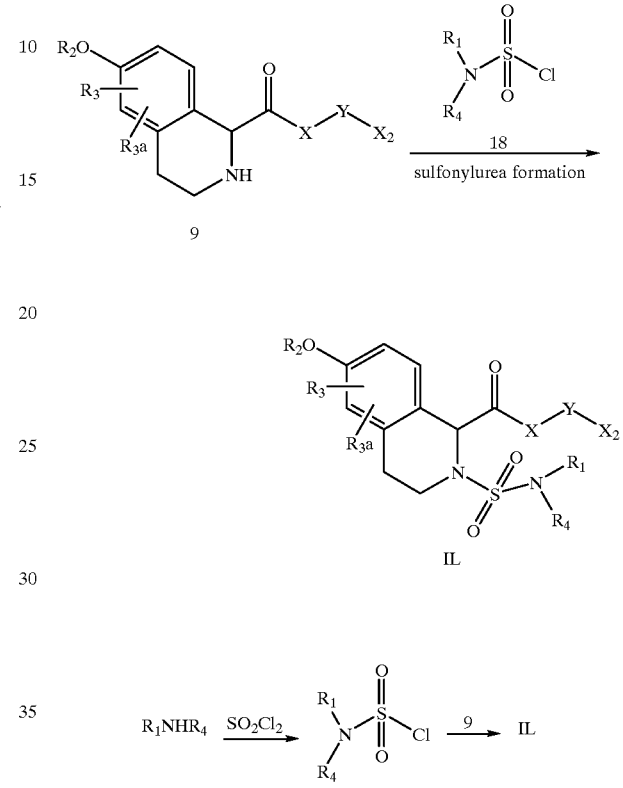
General Scheme 1d: Sulfonylamides
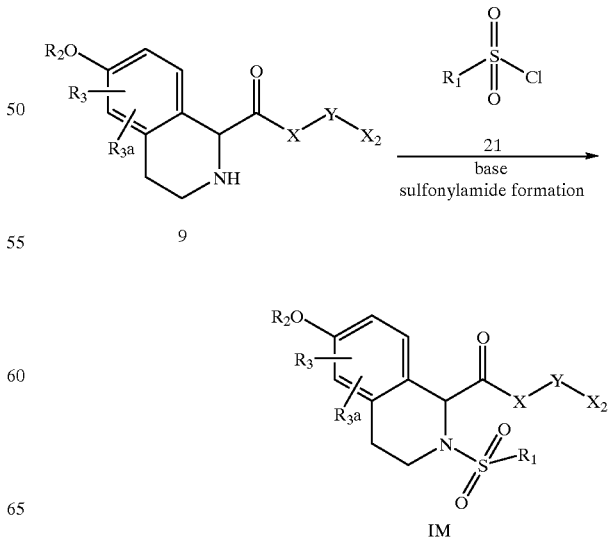

General Scheme 1e: Amines
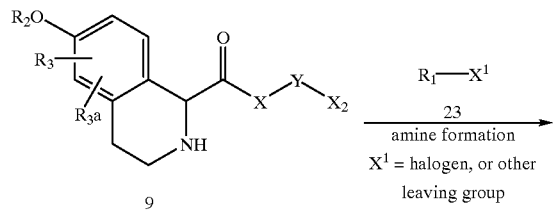
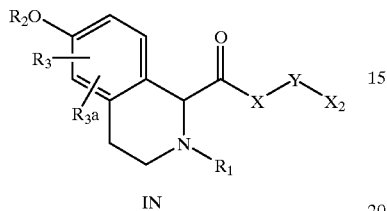
General Scheme 1f
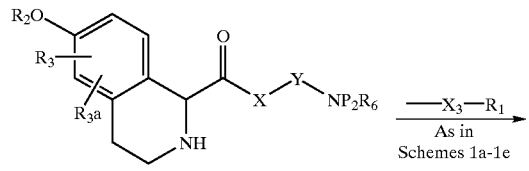
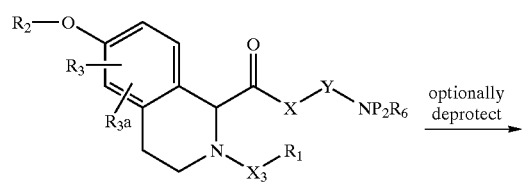
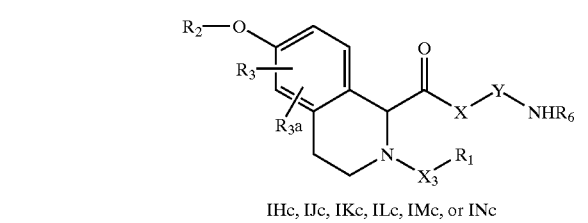
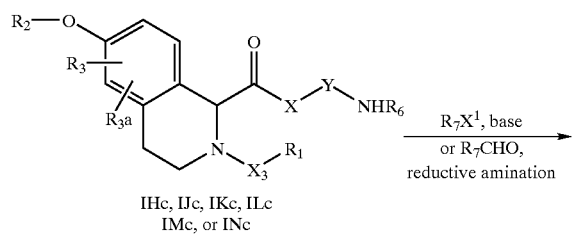
General Scheme 2: Arylation Where R₂ is Phenyl
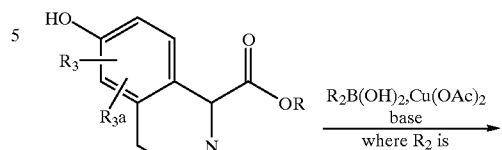
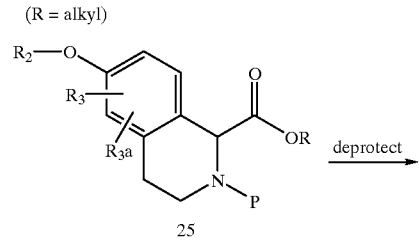
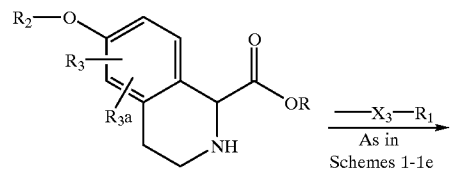
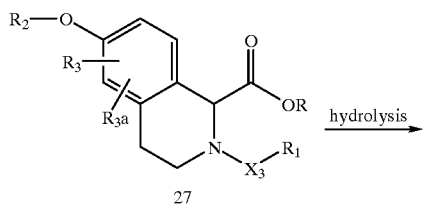
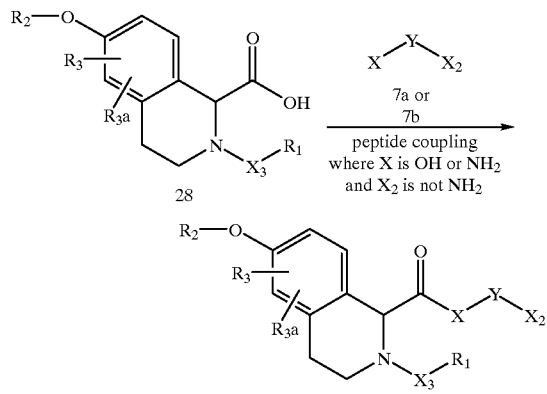

General Scheme 3
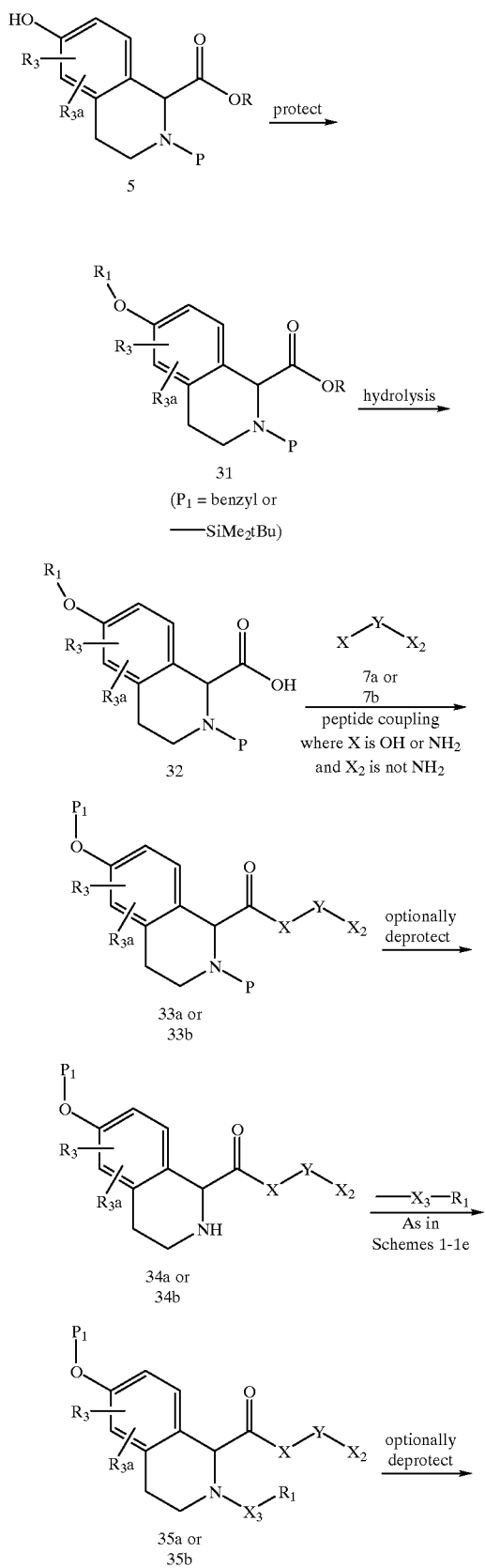
(P₁ = benzyl or —SiMe₂tBu)
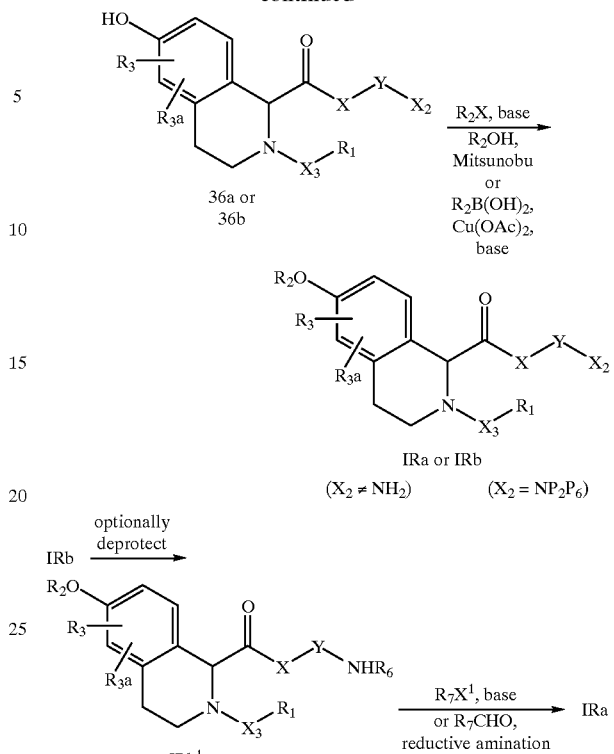
General Scheme 4: Alternate to 9 or 9b
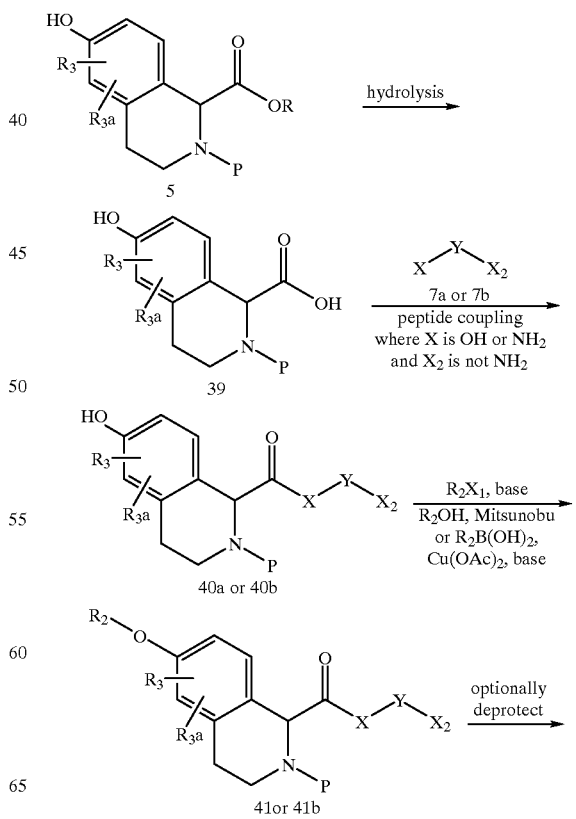

37
-continued
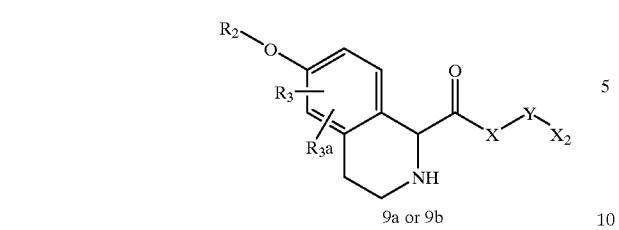
9a or 9b
General Scheme 5
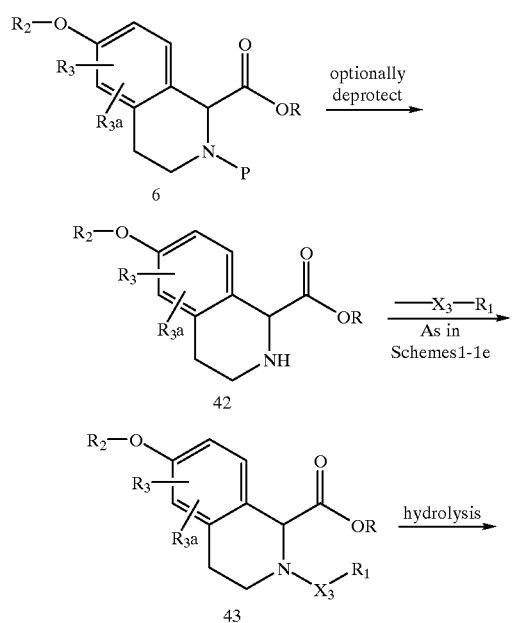
General Scheme 6: Intermediate 39
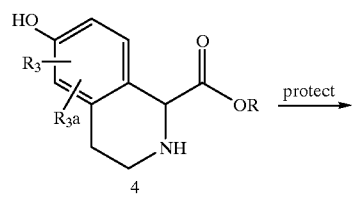
38
-continued
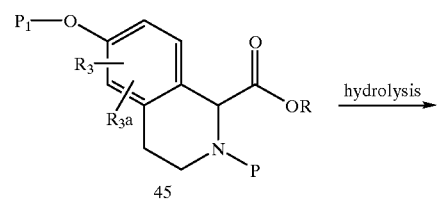
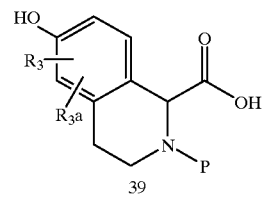
39
General Scheme 7
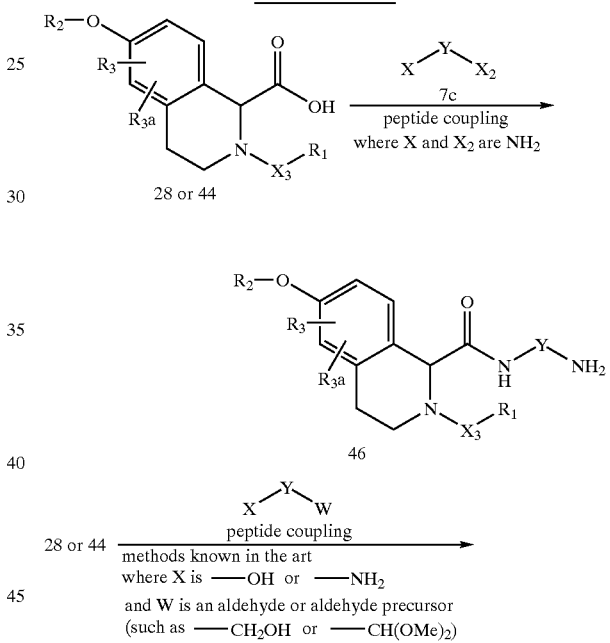
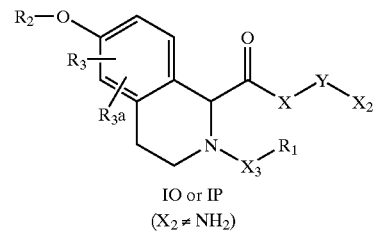
IO or IP
($X_2 \neq NH_2$)

General Scheme 8: Alternate Routes to Core
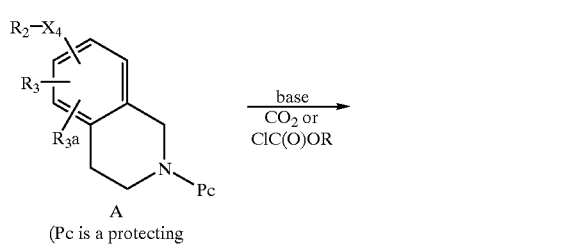
A
(Pc is a protecting group such as Boc or a chiral imine)
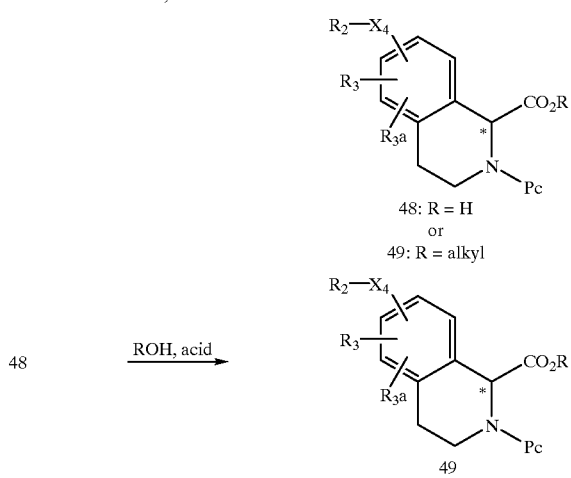
48: R = H
or
49: R = alkyl
48 →(ROH, acid)→ 49
49 →(1) optionally deprotect 2) protect)→ 50
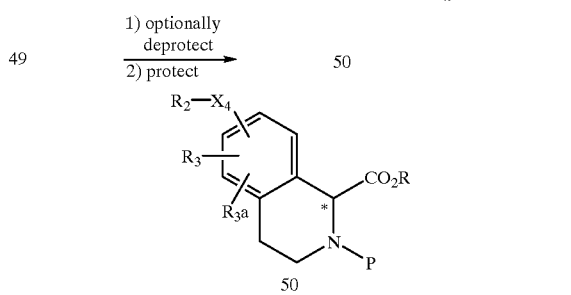
50
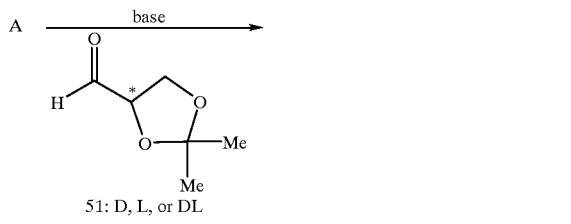
51: D, L, or DL
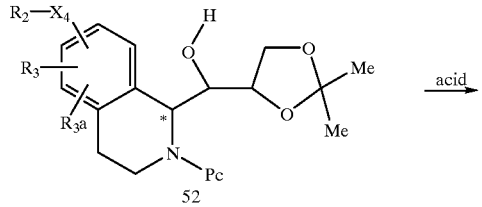
52
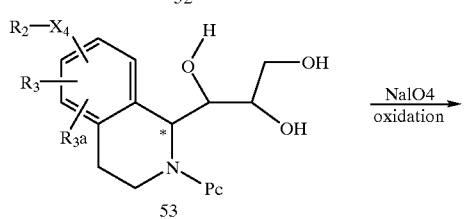
53
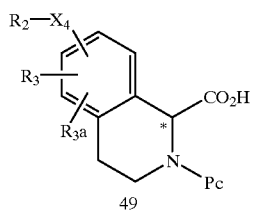
49
General Scheme 9: Alternate Routes to Core
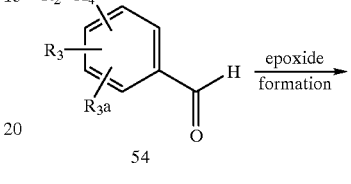
54
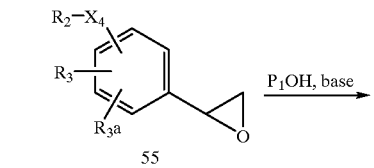
55
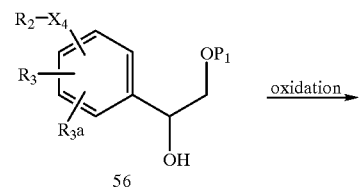
56
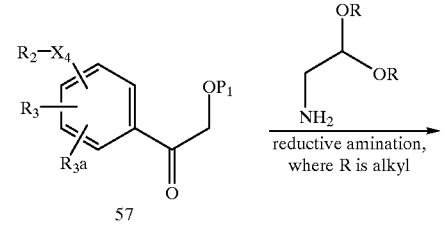
57
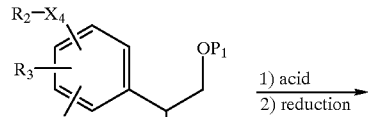
58
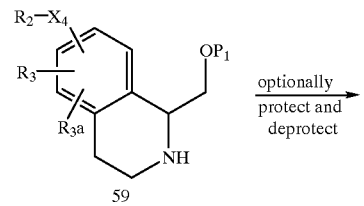
59

-continued
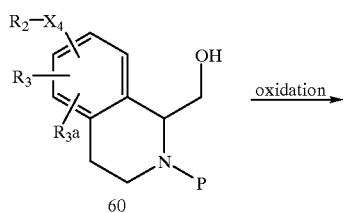
60
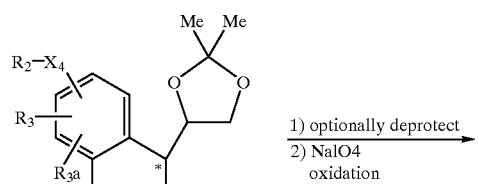
69
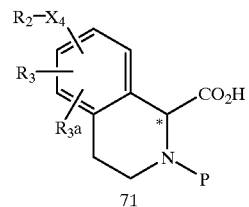
71
Alternatively:
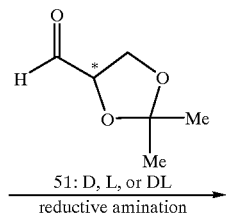
63
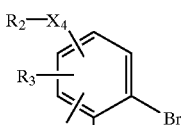
72
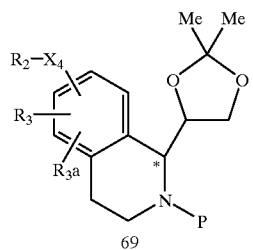
69
General Scheme 10: Alternate Routes to Core
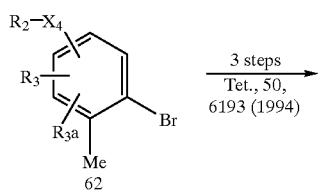
62
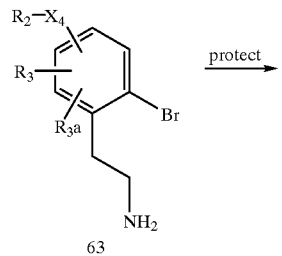
63
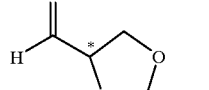
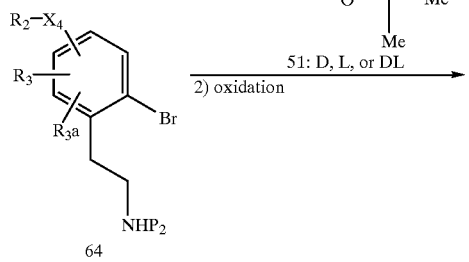
64
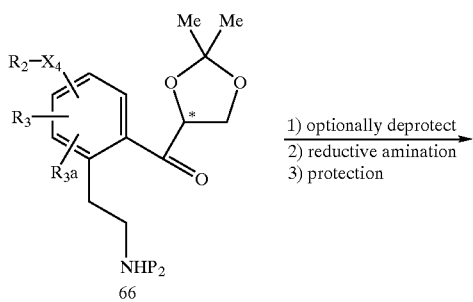
66
Scheme 11: Alternate Core
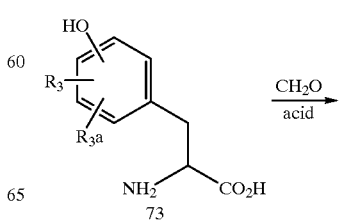
73

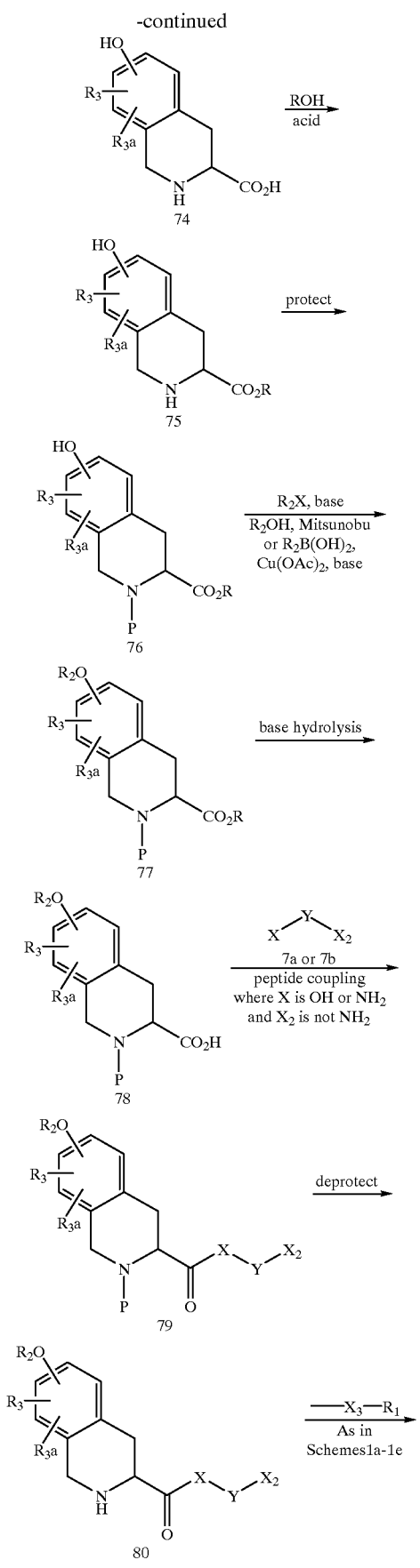

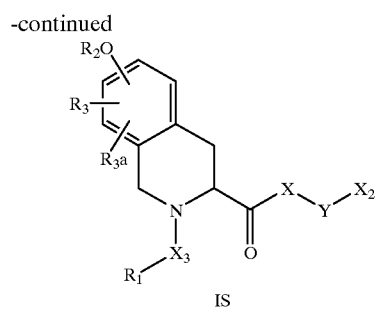

The growth hormone releasing compounds of formula I can be administered to animals, including man, to release growth hormone in vivo. For example, the compounds can be administered to commercially important animals such as swine, cattle, sheep and the like to accelerate and increase their rate and extent of growth, and to increase milk production in such animals.

The present invention includes within its scope pharmaceutical compositions comprising, as an active ingredient, at least one of the compounds of formula I in association with a pharmaceutical carrier or diluent. Optionally, the active ingredient of the pharmaceutical compositions can comprise a growth promoting agent in addition to at least one of the compounds of formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed compounds of formula I of the invention is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed compounds of formula I of the invention is in combination with parathyroid hormone or bisphosphonates, such as MK-217 (alendronate), in the treatment of osteoporosis.

A still further use of the disclosed compounds of formula I is in combination with estrogen, testosterone, a selective estrogen receptor modulator, such as tamoxifen or raloxifene, or a selective androgen receptor modulator, such as disclosed in Edwards, J. P. et al., *Bio. Med. Chem. Let.,* 9, 1003–1008 (1999) and Hamann, L. G. et al., *J. Med. Chem.,* 42, 210–212 (1999), for the treatment of aspects of Metabolic Syndrome, maintenance of muscle strength and function in elderly humans, reversal or prevention of fraility in elderly humans, stimulation and increase in muscle mass and muscle strength, attenuation of protein catabolic response after a major operation or trauma; reducing cachexia and protein loss due to chronic illness such as cancer or AIDS; improvement in muscle mobility, and maintenance of skin thickness.

A further use of the compounds of this invention is in combination with progestin receptor agonists ("PRA").

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself.

To those skilled in the art, it is well known that the current and potential uses of growth hormone are varied and multitudinous. Thus, compounds of formula I can be administered for purposes stimulating release of endogenous growth hormone and would thus have similar effects or uses as growth hormone itself. Compounds of formula I are useful for stimulation of growth hormone release (e.g., in the elderly); maintenance of muscle strength and function (e.g., in the elderly); reversal or prevention of frailty or age-related functional decline ("ARFD") in the elderly; prevention of catabolic side effects of glucocorticoids; prevention and treatment of osteoporosis; treatment of chronic fatigue syndrome (CFS); treatment of acute fatigue syndrome and muscle loss following election surgery; stimulation of the immune system, including improvement of immune response to vaccination; acceleration of wound healing; accelerating bone fracture repair (such as accelerating the recovery of hip fracture patients); accelerating healing of complicated fractures, e.g. disctraction osteogenesis; acceleration of tooth repair or growth; maintenance of sensory function (e.g., hearing, sight, olefaction and taste); treatment of wasting secondary to fractures; treatment of growth retardation; treatment of growth retardation resulting from renal failure or insufficiency; treatment of cardiomyopathy; treatment of wasting in connection with chronic liver disease; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of wasting in connection with chronic obstructive pulmonary disease (COPD); treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of growth retardation associated with the Prader-Willi syndrome and Turner's syndrome; increasing the growth rate of a patient having partial growth hormone insensitive syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients; treatment of osteochondrodysplasias; treatment of Noonan's syndrome; treatment of schizophrenia; treatment of depression; improvement of cognitive function (e.g., treatment of dementia; treatment of Alzheimer's disease; treatment of delayed wound healing and psychosocial deprivation; treatment of catabolism in connection with pulmonary dysfunction and ventilator dependency; treatment of cardiac dysfunction (e.g. associated with valvular disease, myocarial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; adjuvant treatment for ovulation induction; stimulation of thymic development and prevention of the age-related decline of thymic function; treatment of immunosuppressed patients; treatment of sarcopenia; treatment of wasting in connection with AIDS; treatment of wasting in connection with multiple sclerosis or other neurodegenerative disorders; improvement in muscle strength, mobility, maintenance of skin thickness; hair/nail growth; treatment of metabolic homeostasis and renal homeostasis (e.g., in the frail elderly); stimulation of osteoblasts, bone remodelling and cartilage growth; regulation of food intake; stimulation of the immune system in companion animals and treatment of disorders of aging in companion animals; promoting growth in livestock; stimulation of wool growth in sheep; increasing milk production in livestock; treatment of insulin resistance including NIDDM, in mammals (e.g. humans); treatment of insulin resistance in the heart; improvement of sleep quality and correction of the relative hyposomatotropism of senescence due to high increase in REM sleep and a decrease in REM latency; treatment of hypothermia; treatment of frailty such as that associated with aging; treatment of congestive heart failure; treatment of hip fractures; treatment of immune deficiency in individuals with a depressed T4/T8 cell ratio; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in elderly); enhancing the activity of protein kinase B (PKB); improvement of the overall pulmonary function; treatment of sleep disorders; and the treatment of the catabolic state of prolonged critical illness. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

The compounds of the present invention are agents that are growth hormone secretagogues and can be administered to various mammalian species, such as monkeys, dogs, cats, rats, humans, etc., in need of treatment. These agents can be administered systemically, such as orally or parenterally.

The compounds of the invention can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral, intranasal or aerosol forms are quite satisfactory as well.

The dose administered must be carefully adjusted according to the age, weight, and condition of the patient, as well as the route of administration, dosage form and regimen, and the desired result. In general, the dosage forms described above may be administered in amounts from about 0.0001 to about 100 mg/kg or body weight or in an amount within the range from about 1 to about 1000 mg per day, preferably, from about 5 to about 500 mg per day in single or divided doses of one to four times daily.

The compounds of the present invention may be employed alone or in combination with each other and/or other growth hormone secretagogues or other suitable therapeutic agents useful in the treatment of the aforementioned disorders including: Anti-diabetic agents; anti-osteoporosous agents; anti-obesity agents; anti-inflammatory agents; anti-anxiety agents; anti-depressants; anti-hypertensive agents; anti-platelet agents; antithrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; and/or anti-ulcer and gastroesopheageal reflux disease agents.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, non-steroidal progestin receptor agonists, RANK ligand agonists, calcium sensing receptor antagonists, TRAP inhibitors, selective estrogen receptor modulators (SERM), estrogen and AP-1 inhibitors;

Examples of suitable anti-obesity agents for use in combination with the compounds of the present invention include aP2 inhibitors such as those disclosed in U.S. Ser. No. 09/519,079 filed Mar. 6, 2000, PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-COA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, choesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitiors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, MLIB agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

Compounds of the present invention may further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

The above other therapeutic agents, when employed in combination with the compounds of the present invention, may be used, for example, in those amounts indicated in the Physicians' Desk Reference (PDR) or as otherwise determined by one of ordinary skill in the art.

The following Examples represent preferred embodiments of the invention. All temperatures are in ° C. unless indicated otherwise.

General Experimental

HPLCa: Shimadzu, 0–100% B [MeOH:H$_2$O:0.2% H$_3$PO$_4$], 4 min. gradient, 1 min. hold, 220 nM, YMC S5 ODS 4.6×50 mm. HPLCal: Shimadzu, 0–100% B [MeOH: H$_2$O:0.2% H$_3$PO$_4$], 2 min. gradient, 1 min. hold, 220 nM, YMC S5 ODS4.6×33 mm. HPLCb: Shimadzu, 0–100% B [MeOH:H$_2$O:0.1% TFA], 4 min. gradient, 1 min. hold, 220 nM, YMC S5 ODS 4.6×50 mm.

EXAMPLE 1

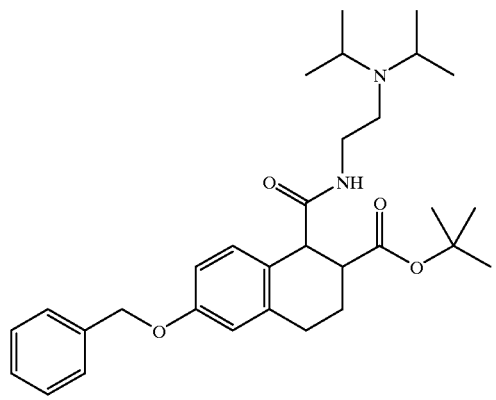

1-[[[2-[Bis(1-methylethyl)amino]ethyl]amino]carbonyl]-3,4-dihydro-6-(phenylmethoxy)-2(1H)-isoquinoline-carboxylic acid, 1,1-dimethylethyl ester

A.

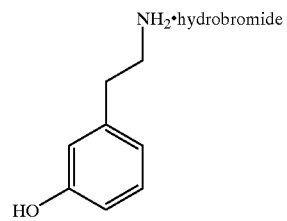

Hydrobromic acid (48%, 500 mL) was added to 3-methoxyphenethylamine (150 g, 0.992 mmol). The formed white solid dissolved upon warming. The reaction mixture was heated at reflux for 3 days. Water was removed by coevaporation with toluene to give the title compound (298 g, >100%) as a white solid % ): LC/MS (electrospray, +ions) m/z 138(M+H).

B.

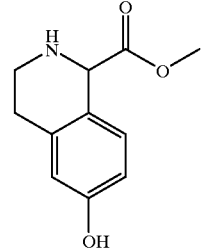

A mixture of Part A compound (266 g, 1.22 mol), glyoxylic acid monohydrate (130 g, 1.41 mol) and 5% hydrochloric acid solution (2 L) was warmed at 80° C. under nitrogen for 8 h. Water was removed by azeotroping with toluene. The residue was dissolved in methanol (1500 mL), and then chlorotrimethylsilane (200 mL, 1.58 mol) was added. The suspension became clear after warming to 49° C. Stirring was continued at 49° C. for 12 h. The reaction mixture was concentrated, and the residue was treated with saturated aqueous sodium bicarbonate solution to make it basic. The aqueous solution (saturated with sodium chloride) was extracted with ethyl acetate (6×300 mL) until no product was visible in the aqueous layer by TLC. Solvent was removed in vacuo. Ethanol was added to the residue, and the yellow solid that formed was collected by filtration to give the title compound (87 g, 35%): LC/MS (electrospray, +ions) m/z 208(M+H).

C.

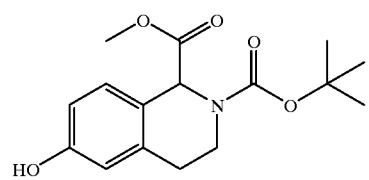

A solution of di-tert-butyl dicarbonate (89 g, 0.40 mol) in tetrahydrofuran (500 mL) was slowly added to a suspension of Part B compound (76 g, 0.37 mol) in tetrahydrofuran (800 mL) and triethylamine (5 mL, 0.036 mol). The reaction was stirred at ambient temperature for 2 h until bubbling stopped. The reaction solution was passed through a pad of silica gel, rinsing with tetrahydrofuran. The solvent was removed, and the residue was dissolved in ethyl acetate (400 mL). The ethyl acetate solution was washed with water (500 mL), 10% aqueous citric acid solution (200 mL) and brine. The organic layer was dried over sodium sulfate, and the mixture was filtered. The filtrate was concentrated to give the title compound (128 g, 100%) as a light brown oil: LC/MS (electrospray, +ions) m/z 308(M+H).

D.

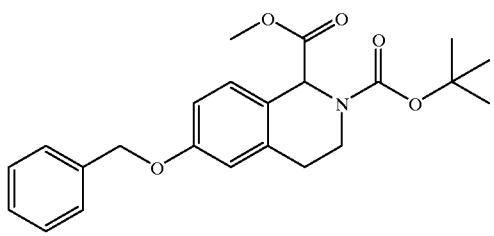

A mixture of Part C compound (48.0 g, 0.156 mol), benzyl bromide (25 mL, 0.209 mol) and potassium carbonate (74 g, 0.536 mol) in dimethylformamide (500 mL) was stirred overnight. The reaction mixture was filtered, rinsing with ethyl acetate, and the solvent was removed in vacuo. The residue was dissolved in ethyl acetate, and the organic solution was washed with water followed by 10% aqueous citric acid solution (2×) and brine and then dried over sodium sulfate. The mixture was filtered and the filtrate concentrated. Purification by silica gel column chromatography, eluting with 10% ethyl acetate in heptane (6 L) followed by 20% ethyl acetate in heptane (4 L), gave the title compound (58.0 g, 93%) as a white foam.

E.

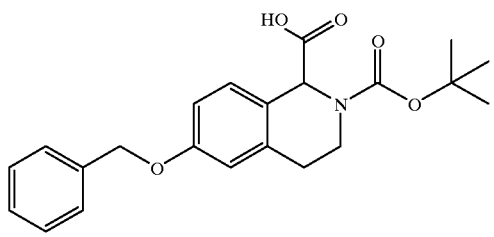

Part D compound (21.51 g, 54.12 mmol) was dissolved in methanol (50 mL) and tetrahydrofuran (50 mL), and then water (50 mL) was added. To the resultant milky mixture was added sodium hydroxide (6.49 g, 162.3 mmol). Within 10 min, the reaction temperature rose from 23° C. to 40° C., and the reaction became clear. After stirring for 2.5 h, the reaction mixture was transferred to a separatory funnel and water (50 mL) was added. The product was extracted with ethyl acetate (2×250 mL). The rich organic layer was washed with 1 N hydrochloric acid solution (250 mL) followed by brine (100 mL) and dried over sodium sulfate. The mixture was filtered, and the filtrate was concentrated and dried in vacuo to give the title compound (17.3 g, 83%) as a white foam: LC/MS (electrospray, +ions) m/z 382(M+H).

F.

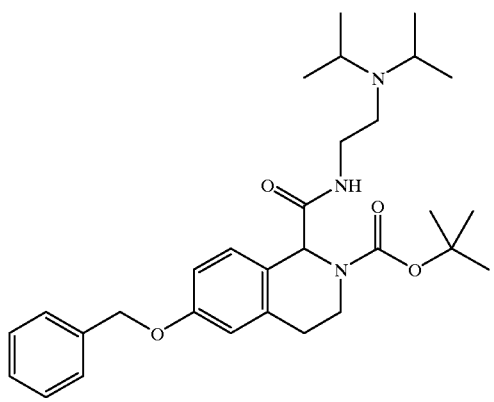

A solution of Part E compound (500 mg, 1.3 mmol) in dimethylformamide (3 mL) was treated with diisopropyl-ethylenediamine (248 μL, 1.37 mmol) followed by 1-hydroxy-7-azabenzotriazole (213 mg, 1.56 mmol) and 1-(3-dimethylaminopropyl)-3-ethylcarbodiimide hydrochloride (300 mg, 1.56 mmol). The mixture was stirred overnight at ambient temperature. Evaporation of the solvent gave a residue, which was dissolved in dichloromethane. The dichloromethane solution was washed with water (3×30 mL) and dried over magnesium sulfate. The mixture was filtered, and the filtrate was concentrated. Silica gel flash column chromatography purification gave the title product (523 mg, 79%) as a white solid: LC/MS (electrospray, +ions) m/z 510(M+H).

EXAMPLE 1A

An alternative procedure for the preparation of Example 1 Part B compound follows:

A.

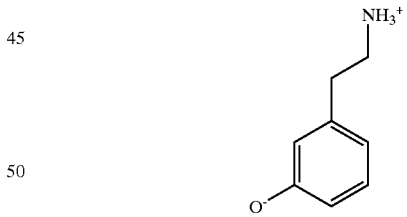

A solution of 48% hydrobromic acid (100 mL) was added slowly and cautiously to a flask at 4° C. containing m-methoxyphenethylamine (50 g, 0.331 mol). The amine salt formed as a white solid. The reaction mixture was heated at 140° C. under gentle reflux for 18 h. After cooling, the solvent was evaporated to give a white residue, which was further dried under high vacuum. The solid was then dissolved in water, and dichloromethane was added to extract the non-polar impurities. The aqueous layer was made alkaline by the addition of powdered sodium carbonate. Water was evaporated to give a white solid, which was dried in vacuo. The extraction of the product was done by the addition of ethyl acetate, with heating at reflux. Molecular sieves (4 Å) were added to absorb the residual water. The mixture was decanted. The ethyl acetate extraction was repeated until only trace amounts of product were present in the extract. The ethyl acetate extracts were combined. Ethyl acetate was evaporated to give the title product (29 g, 64%) as a white solid.

B.

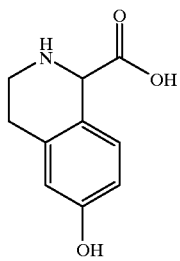

To a 4° C. solution of Part A compound (3.08 g, 22.5 mmol) in denatured ethanol (70 mL) was added a solution of glyoxylic acid monohydrate (2.0 g, 22 mmol) in ethanol (10 mL) dropwise. Shortly after the addition of glyoxylic acid, a white precipitate formed. The cooling bath was removed, and the reaction mixture was stirred for 2 h at ambient temperature. Filtration gave the title product (3.1 g, 73%) as a white solid: LC/MS (electrospray, +ions) m/z 194(M+H).

C.

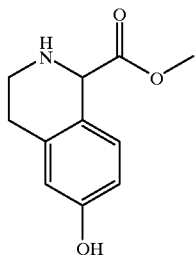

A solution of hydrogen chloride in methanol (150 mL), prepared by the addition of acetyl chloride (13 mL) to methanol (500 mL), was added to Part B compound (6.0 g, 31.1 mmol). The mixture was heated at reflux for 48 h. The solvent was evaporated to give a white residue, to which ethyl acetate and saturated aqueous sodium carbonate were added. The two layers were separated, and extraction of the aqueous layer with ethyl acetate was repeated several times. The ethyl acetate layers were combined and dried over magnesium sulfate. The mixture was filtered, and the filtrate was concentrated to give the title product (3.93 g, 61%) as a yellow solid: LC/MS (electrospray, +ions) m/z 208(M+H).

EXAMPLE 1B

An alternative procedure for the preparation of Example 1 Part C compound follows:

A.

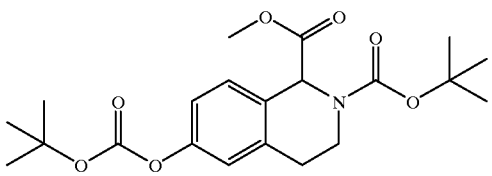

To a mixture of Example I Part B compound (3.0 g, 14.5 mmol) and di-tert-butyl dicarbonate (8.21 g, 37.6 mmol) was added tetrahydrofuran (75 mL). This mixture was stirred to give a slurry. Triethylamine (5.3 mL, 38.0 mmol) was added, and the reaction mixture was stirred at ambient temperature for 18 h. The title compound was used in the next step without work-up.

B.

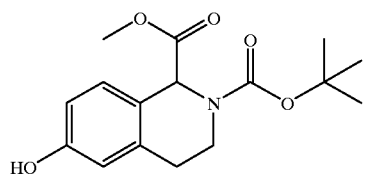

To the reaction mixture containing Part A compound was added methanol (30 mL) and then 25 wt % sodium methoxide in methanol (15 mL). The resultant viscous reaction mixture was stirred at ambient temperature for 2 h. A solution of 10% acetic acid in water (50 mL) was added. The reaction temperature rose from 22° C. to 34° C., and gas evolution was observed. Tetrahydrofuran and methanol were removed by rotovaporation. The product was extracted with dichloromethane (2×50 mL). The organic layer was washed with water (50 mL) and brine (25 mL) and dried over sodium sulfate. The mixture was filtered, and the filtrate was concentrated to give the title product (4.6 g) as a white foam: LC/MS (electrospray, +ions) m/z 308(M+H).

EXAMPLE 2

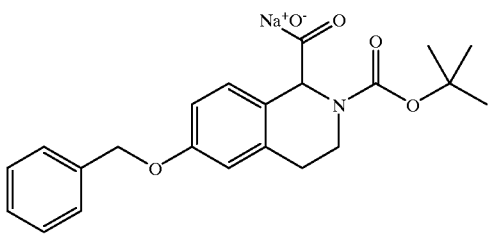

To a solution of Part D compound from Example 1 (0.60 g, 1.51 mmol) in tetrahydrofuran (6 mL) was added 1 N sodium hydroxide solution (6 mL, 6 mmol). After stirring for 45 h, the reaction mixture was transferred to a separatory funnel, and the product was extracted with ethyl acetate (2×10 mL). The organic layers were combined and washed with 1 N sodium hydroxide solution (5 mL) and brine (5 mL) and then dried over anhydrous sodium sulfate. The mixture was filtered, and the filtrate was concentrated and dried in vacuo to give the title compound (0.41 g, 67%) as a white solid.

EXAMPLE 3

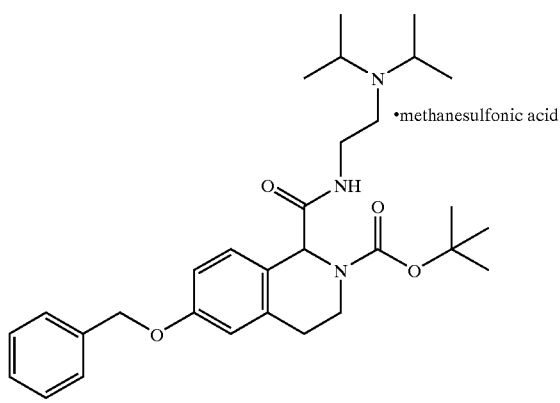

To a solution of Part F compound from Example 1 (107 mg, 0.210 mmol) in dichloromethane (10 mL) was added methanesulfonic acid (16 μL, 0.247 mmol). The solvent was evaporated, and the residue was dissolved in acetone. Hexanes was then added. Concentration gave the title product (110 mg, 86%) as a white solid: LC/MS (electrospray, +ions) m/z 510 (M+H).

EXAMPLE 4

Isomer A and Isomer B

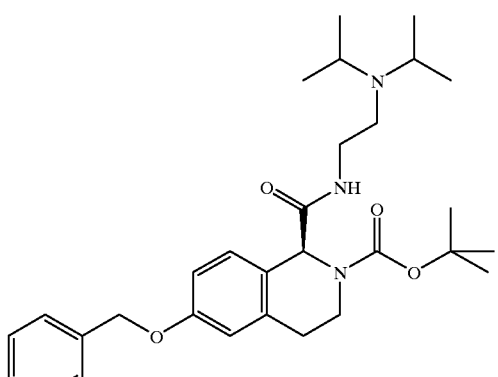

A

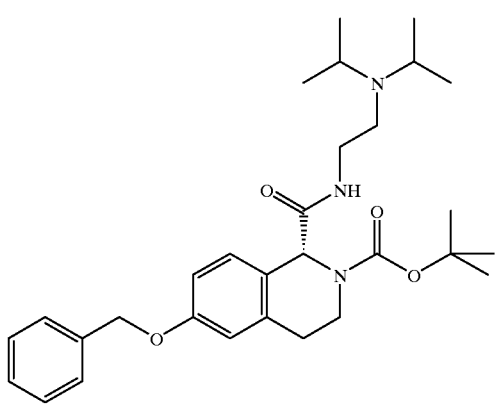

Example 1, title compound (2 batches of 500 mg) was resolved on Chiralpak OD column (50×500 mm), eluting with 20% isopropanol in hexanes to give the title compounds, Isomer A (0.350 g, 35%) and Isomer B (0.356 g, 36%).

Isomer A [α]D=−22.7° (c=0.1; methanol)

Isomer B [α]D=+28.4° (c=0.1; methanol)

EXAMPLE 5

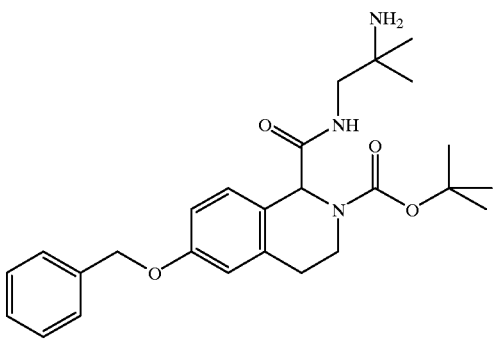

A solution of Part E compound from Example 1 (100 mg, 0.26 mmol) in dimethylformamide was treated with 1,2-diamino-2-methylpropane (27 μL, 0.26 mmol) followed by 1-hydroxy-7-azabenzotriazole (42 mg, 0.31 mmol) and 1,3-diisopropylcarbodiimide (50 μL, 0.32 mmol), and the reaction mixture was stirred overnight at ambient temperature. The crude reaction mixture was loaded onto a SCX column that had been washed with methanol. The column was washed with methanol (3×10 mL) and then the product was eluted from the column with 2.0 M ammonia in methanol (6 mL). Evaporation of the solvent gave the title product (109 mg, 92%) as a white solid: LC/MS (electrospray, +ions) m/z 454 (M+H).

EXAMPLES 6 to 26

In a manner analogous to that of Example 5, Examples 6–26 listed in the table below were prepared from Part E compound of Example 1 and the respective amines. Examples 6 to 26 compounds were purified by preparative HPLC, eluting with a gradient system of methanol and water with 0.2% trifluoroacetic acid and neutralized with sodium bicarbonate. Example 19–26 compounds were prepared as methanesulfonic acids in a manner analogous to that of Example 3, except that exactly one equivalent of methanesulfonic acid was used.

In the tables of compounds which follow, the $X_1$ designation refers to the point of attachment of the particular R1 moiety shown to the remainder of the molecule.

| Example No. | X₁—R1 | LC/MS (M + H)⁺ |
|---|---|---|
| 6 | 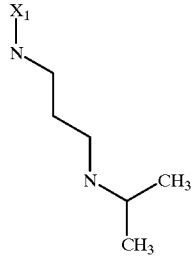 | 482 |
| 7 | 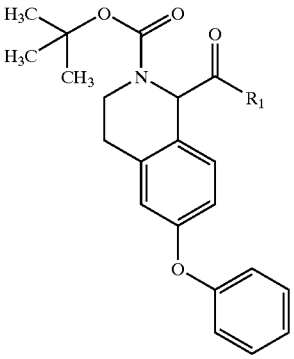 | 477 |
| 8 | 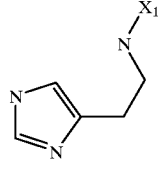 | 491 |
| 9 | 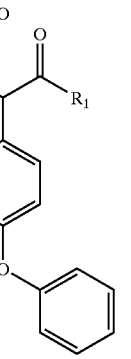 | 468 |
-continued
| Example No. | X₁—R1 | LC/MS (M + H)⁺ |
|---|---|---|
| 10 | 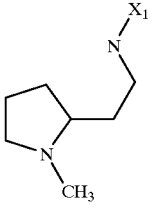 | 468 |
| 11 | 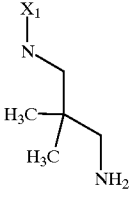 | 494 |
| 12 | 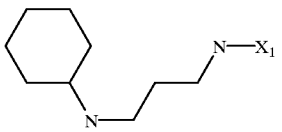 | 522 |
| 13 | 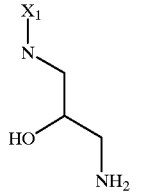 | 456 |
| 14 | 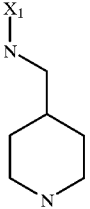 | 480 |

-continued
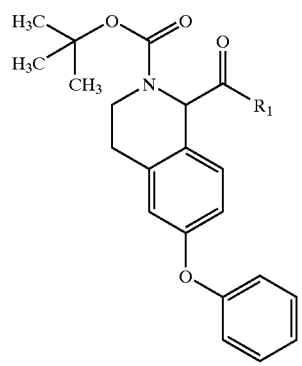
= X₁—R1
| Example No. | X₁—R1 | LC/MS (M + H)⁺ |
|---|---|---|
| 15 | 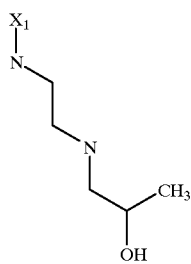 | 484 |
| 16 | 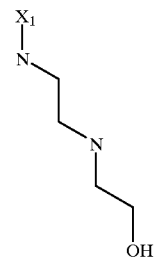 | 470 |
| 17 | 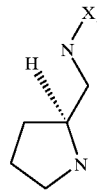 | 466 |
| 18 | 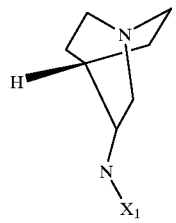 | 492 |
-continued
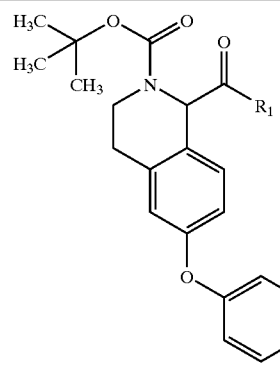
= X₁—R1
| Example No. | X₁—R1 | LC/MS (M + H)⁺ |
|---|---|---|
| 19 | 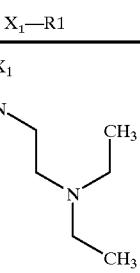 | 496 |
| 20 | 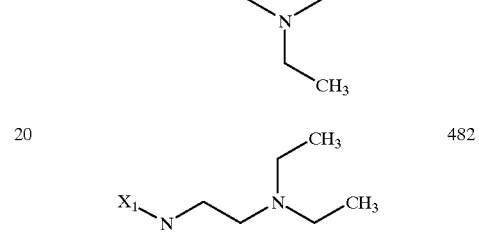 | 482 |
| 21 | 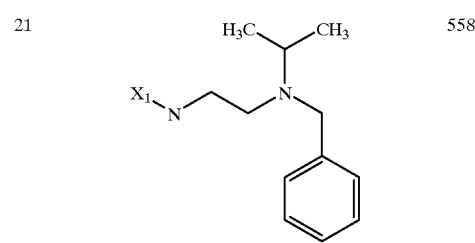 | 558 |
| 22 | 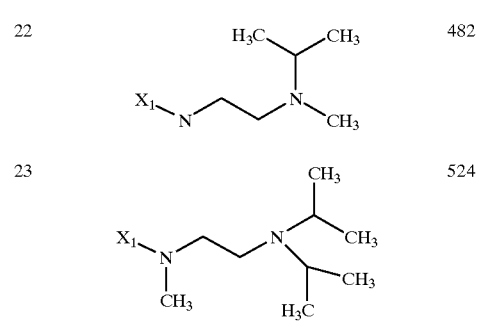 | 482 |
| 23 | 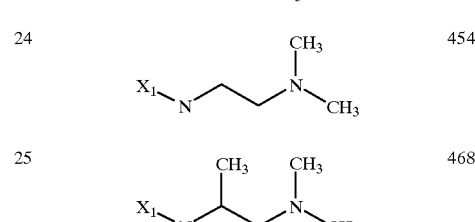 | 524 |
| 24 | 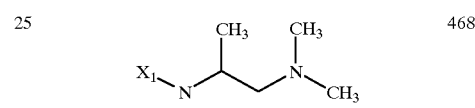 | 454 |
| 25 |  | 468 |

-continued

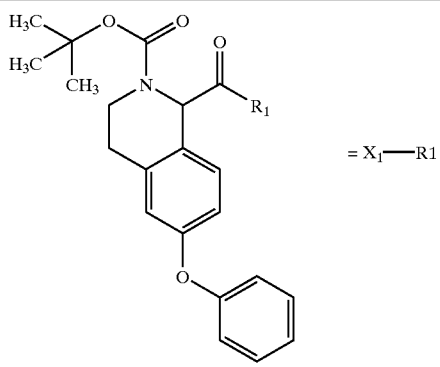

= X₁—R1

| Example No. | X₁—R1 | LC/MS (M + H)⁺ |
|---|---|---|
| 26 | 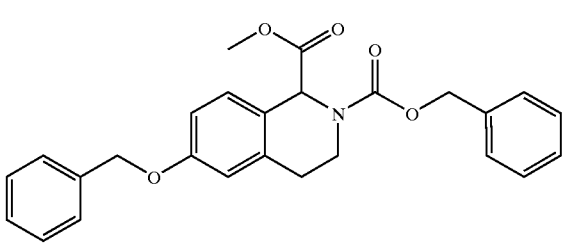 | 468 |

EXAMPLE 27

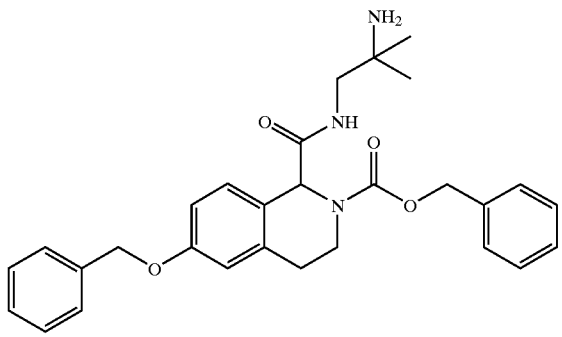

A.

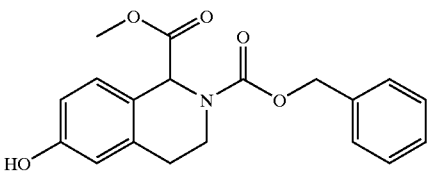

To a suspension of Part B compound from Example 1 (5.0 g, 24 mmol) in dichloromethane (100 mL) was added triethylamine (4.0 mL, 29 mmol). The mixture was cooled to 4° C. and benzylchloroformate (4.1 mL, 29 mmol) was added dropwise. The reaction mixture became clear and was stirred for 15 min. Additional dichloromethane was added and was washed with water followed by 5% citric acid solution. The organic layer was dried over magnesium sulfate, and the mixture was filtered. The filtrate was concentrated to give the title compound (8.0 g, 97%) as a yellow solid.

B.

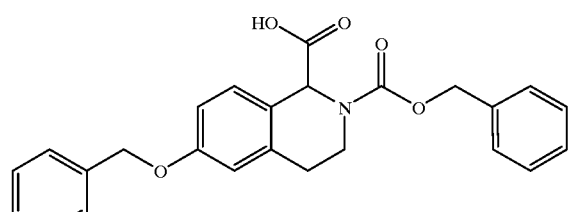

A heterogeneous mixture of Part A compound (8.0 g, 23.5 mmol), benzyl bromide (4.33 g, 23.5 mmol) and potassium carbonate (13 g, 94.1 mmol) in dimethylformamide (20 mL) was stirred at ambient temperature overnight. The reaction mixture was concentrated, and the residue was dissolved in ethyl acetate (300 mL). The organic layer was washed with water (3×200 mL) and dried over magnesium sulfate. The mixture was filtered, and the filtrate was concentrated. Flash column chromatography (1:1 ethyl acetate/hexanes) gave the title product (9.2 g, 91%) as a yellow syrup.

C.

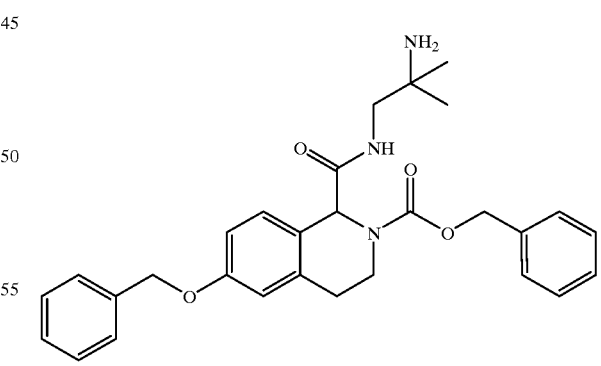

A solution of the methyl ester from Part B compound (3.6 g, 8.38 mmol) in methanol (3 mL) and tetrahydrofuran (3 mL) was treated with 10 M aqueous sodium hydroxide (2 mL, 20 mmol) and stirred at ambient temperature for 2 h. The reaction solution was acidified with 2 N hydrochloric acid solution to pH ~1–2. The product was extracted with ethyl acetate. The organic layer was washed with brine (2×) and dried over magnesium sulfate. The mixture was filtered, and the filtrate was concentrated to give the title product (3.0 g, 86%) as a yellow solid: LC/MS (electrospray, +ions) m/z 418(M+H).

D.

A solution of Part C compound (100 mg, 0.24 mmol) in dimethylformamide (3 mL) was treated with 1,2-diamino-2-methylpropane (30 μL, 0.29 mmol) followed by 1-hydroxy-7-azabenzotriazole (40 mg, 0.29 mmol) and 1,3-diisopropylcarbodiimide (45 μL, 0.29 mmol). The reaction mixture was stirred at ambient temperature overnight. The solvent was removed, and the residue was dissolved in methanol. This solution was applied to a CUBCx12M6 column, which was prewashed with methanol (10 mL). The column was washed with methanol (3×10 mL), and then the product was eluted with 2 M ammonium in methanol (10 mL). Evaporation of the solvent gave the title compound (110 mg, 94%) as a white solid: LC/MS (electrospray, +ions) m/z 488 (M+H).

EXAMPLES 28 to 45

In a manner analogous to that of Example 27, Examples 28–45 listed in the table below were prepared from Part C compound of Example 27 and the respective amines. Examples 38 and 45 compounds were purified by preparative HPLC, eluting with a gradient system of methanol and water with 0.2% trifluoroacetic acid. These compounds were isolated as trifluoroacetic acid salts.

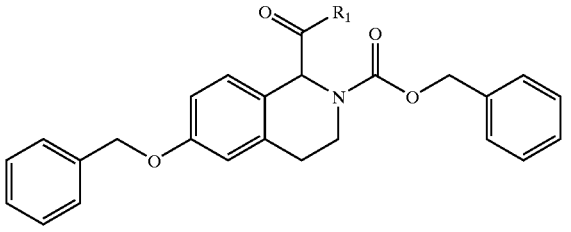

= X₁—R1

| Example No. | X₁—R1 | LC/MS (M + H)⁺ |
|---|---|---|
| 28 | 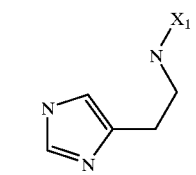 | 516 |
| 29 | 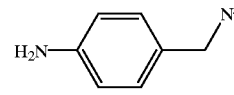 | 511 |
| 30 | 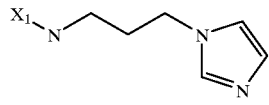 | 522 |
| 31 | 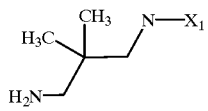 | 525 |
| 32 | 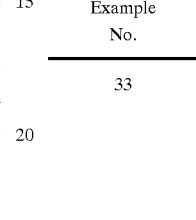 | 502 |
| 33 | 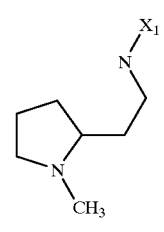 | 502 |
| 34 | 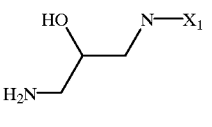 | 528 |
| 35 | 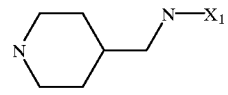 | 490 |
| 36 | 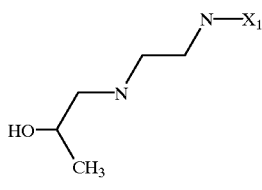 | 514 |
| 37 | 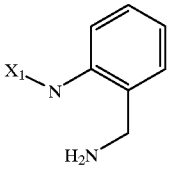 | 518 |
| 38 | 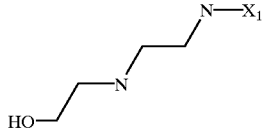 | 522 |
| 39 | | 504 |

-continued

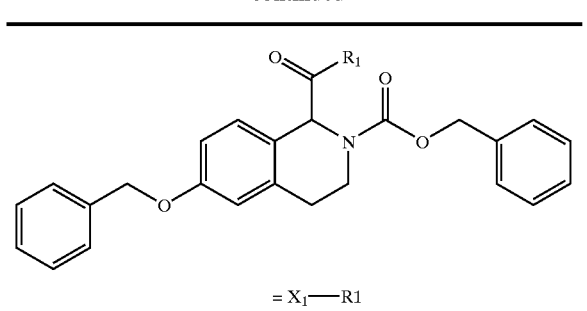

= X₁—R1

| Example No. | X₁—R1 | LC/MS (M + H)⁺ |
|---|---|---|
| 40 | (pyrrolidinylmethylamine structure) | 500 |
| 41 | (methylpiperidinyl-propylamine structure) | 556 |
| 42 | (quinuclidinylamine structure) | 526 |
| 43 | (morpholinyl-propylamine structure) | 544 |
| 44 | (N,N,N'-trimethyl-ethylenediamine structure) | 530 |
| 45 | (4-aminomethyl-piperidinyl structure) | 514 |

EXAMPLE 46

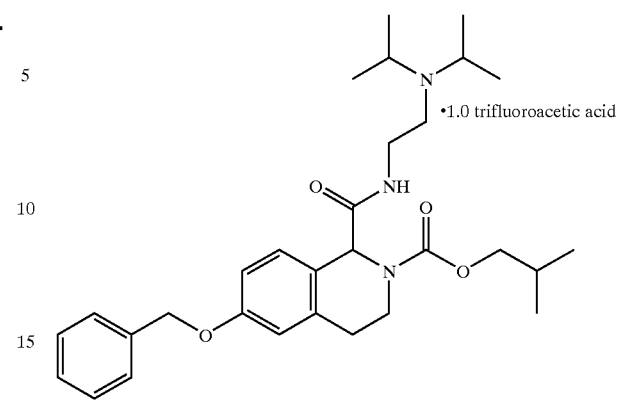

A.

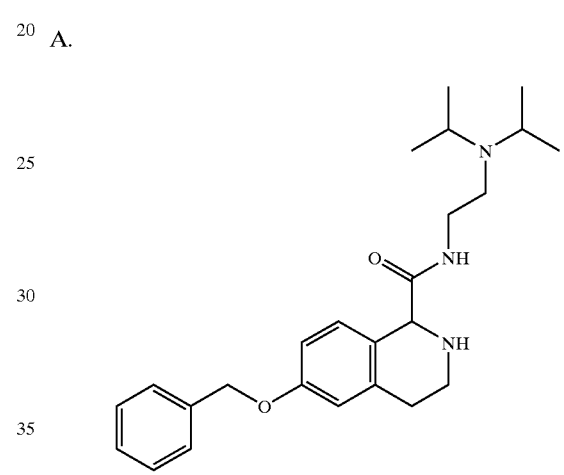

To a flask containing Example 1, title compound, (1.57 g, 3.1 mol) was slowly added 4 N hydrogen chloride in dioxane (10 mL, 40 mol) with a syringe at ambient temperature. It was stirred for 1 h and then concentrated. The residue was dissolved in ethyl acetate and then the pH was adjusted to pH 8 with the addition of 1 N sodium hydroxide solution. The ethyl acetate layer was separated and dried over sodium sulfate. The mixture was filtered and the filtrate concentrated to give the title compound (1.13 g, 89%) as a yellow oil: LC/MS (electrospray, +ions) m/z 410(M+H).

B.

To a 4° C. solution of Part A compound (60.0 mg, 0.147 mmol) and triethylanine (30 μL, 0.215 mmol) in tetrahydrofuran (10 mL) was added isobutyl chloroformate (28.5 µL, 0.220 mmol). The mixture was stirred at 0° C. to 10° C. for 1 h. The mixture was concentrated, and the concentrate was purified by preparative HPLC, eluting with a gradient system of 30–100% B (where A 90% water, 10% methanol, 0.2% trifluoroacetic acid and B 90% methanol, 10% water, 0.2% trifluoroacetic acid), to give the title compound (81 mg, 89%) as a yellow oil:HPLCa rt =3.99 min; LC/MS (electrospray, +ions) m/z 510(M+H).

EXAMPLE 47 to 54

In a manner analogous to that of Example 46, Examples 47–54 compounds listed in the table below were prepared from Part A compound from Example 46 and the respective chloroformate.

| Example No. | $X_1$—R1 | LC/MS (M + H) + |
|---|---|---|
| 47 | benzyl ($C_6H_5CH_2$—$X_1$) | 544 |
| 48 | $CH_3$—$X_1$ | 468 |
| 49 | $H_3C$—$CH_2$—$X_1$ | 482 |
| 50 | $H_3C$—$(CH_2)_2$—$X_1$ | 496 |
| 51 | $H_3C$—$(CH_2)_3$—$X_1$ | 510 |
| 52 | $H_2C$=CH—$CH_2$—$X_1$ | 494 |
| 53 | (menthyl)—$X_1$ | 592 |

| Example No. | $X_1$—R1 | LC/MS (M + H) + |
|---|---|---|
| 54 | phenyl—$X_1$ | 530 |

EXAMPLE 55

A.

To a −5° C. solution of methyl 2-hydroxyisobutyrate (118 mg, 1.0 mmol) and triethylamine (139 µL, 1.0 mmol) in dichloromethane (4 mL) was added 1.9 M phosgene in toluene (0.8 mL, 1.5 mmol). After stirring for 1 h between −5 to 0° C., the reaction mixture was concentrated and used in the next procedure without purification.

B.

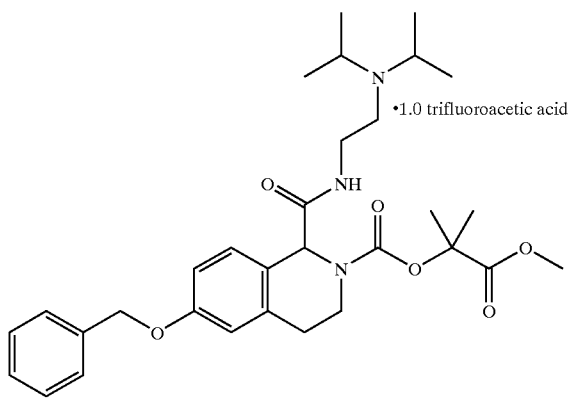

At 0° C., a solution of Part A compound (1.0 mmol) in dichloromethane (5 mL) was treated with Part A compound from Example 46 (45 mg, 0.11 mmol) followed by triethylamine (111 μL, 0.80 mmol). The reaction mixture was stirred at 0° C. to 5° C. for 2 h and then concentrated. Purification by preparative HPLC, eluting with a gradient system of 30–100% B (where A=90% water, 10% methanol, 0.2% trifluoroacetic acid and B=90% methanol, 10% water, 0.2% trifluoroacetic acid), gave the title compound (52.2 mg, 71%) as a yellow oil: HPLCa rt=3.81 min; LC/MS (electrospray, +ions) m/z 554(M+H).

EXAMPLES 56 to 62

In a manner analogous to that of Example 55, Examples 56–62 compounds listed in the table below were prepared from Part A compound from Example 46 and the respective chloroformate prepared as in Example 55 Part A.

| Example No. | Structure | LC/MS (M + H)+ |
| --- | --- | --- |
| 56 | 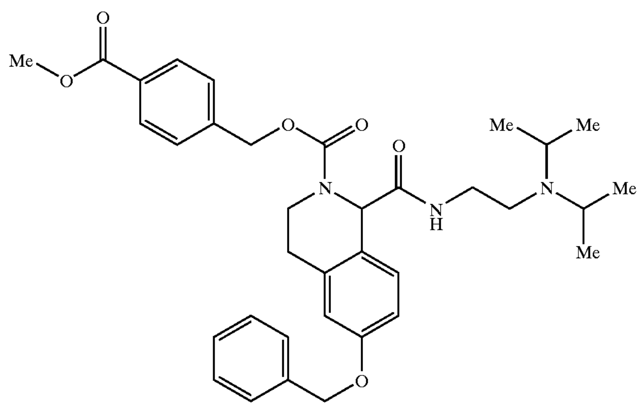 | 602 |
| 57 | 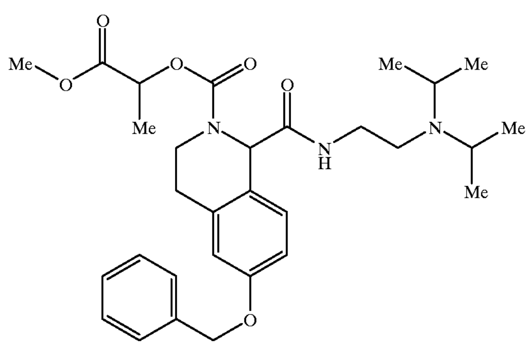 | 540 |
| 58 | 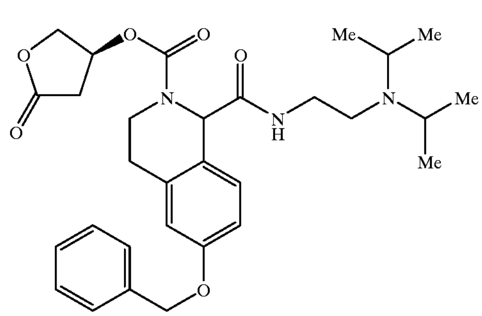 | 538 |

-continued
| Example No. | Structure | LC/MS (M + H)+ |
|---|---|---|
| 59 | 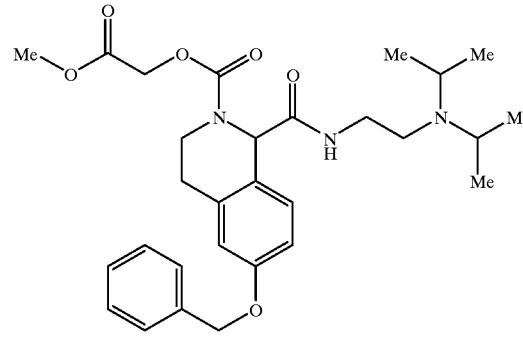 | 526 |
| 60 | 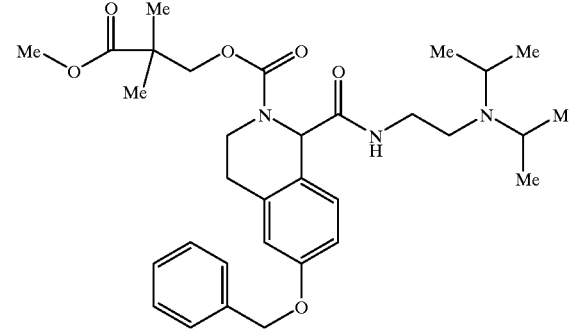 | 568 |
| 61 | 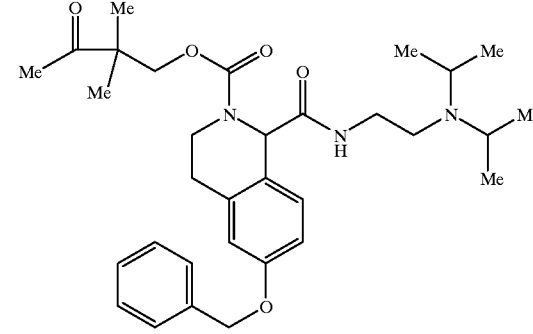 | 538 |
| 62 | 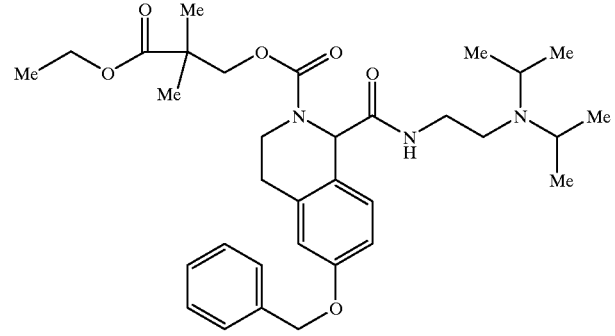 | 568 |

EXAMPLE 63

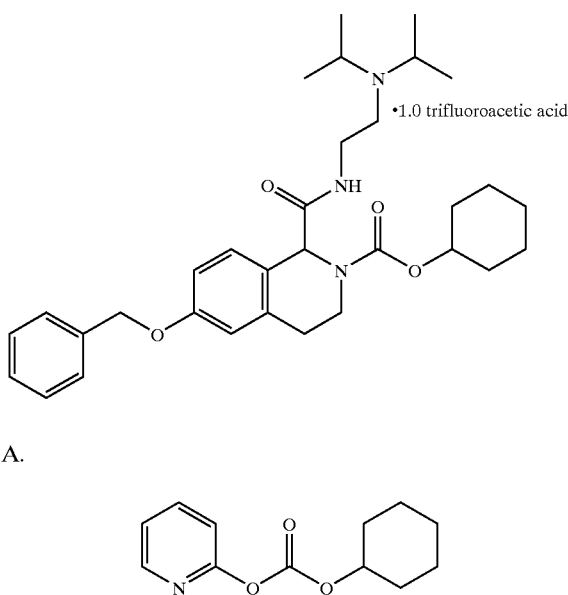

A.

A mixture of cyclohexanol (12.5 μL, 0.12 mmol), carbonic acid di-2-pyridyl ester (25.9 mg, 0.12 mmol) and triethylamine (16.7 μL, 0.12 mmol) in dichloromethane (5 mL) was stirred at ambient temperature overnight. The reaction mixture was concentrated, and the residue was partitioned between ethyl acetate (20 mL) and concentrated sodium carbonate solution. The two layers were separated, and the organic layer was washed with brine and dried over magnesium sulfate. The mixture was filtered, and the filtrate was concentrated. The title product was purified by silica gel preparative TLC, eluting with 1:1 dichloromethane/ethyl acetate, and isolated in a yield of 26 mg (98%).

B.

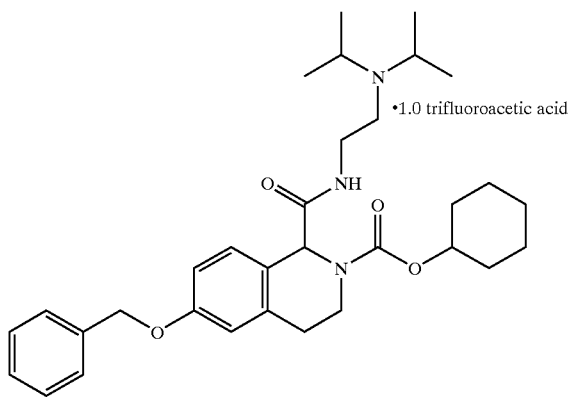

To a solution of Part A compound from Example 46 (81.8 mg, 0.20 mmol) and triethylamine (27.8 μL, 0.20 mmol) in dichloromethane (7 mL) was added Part A compound (26 mg, 0.12 mmol). The reaction mixture was stirred at ambient temperature under nitrogen for 12 h. The mixture was purified by a SCX column as follows. The column was conditioned by rinsing with methanol (10 mL). The reaction mixture was loaded onto the column, followed by methanol (2×20 mL) and finally, the product was eluted with 2 N ammonia in methanol (6 mL). Further purification by preparative HPLC, eluting with 30–100% B (where A=90% water, 10% methanol, 0.2% trifluoroacetic acid and B=90% methanol, 10% water, 0.2% trifluoroacetic acid), gave the title compound (49.7 mg, 65%) as a yellow oil: LC/MS (electrospray, +ions) m/z 536(M+H).

EXAMPLE 64

Isomer A and Isomer B

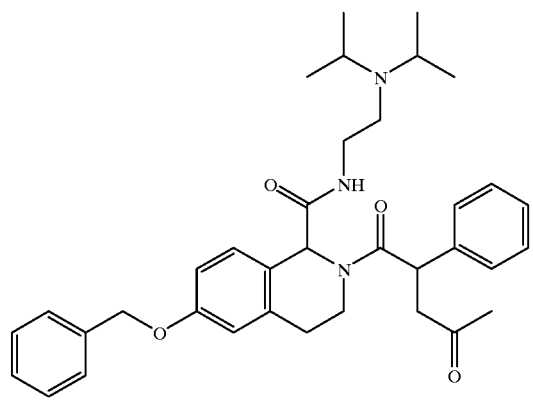

A solution of Part A compound from Example 46 (41.0 mg, 0.1 mmol) in dichloromethane (0.5 mL) was added to 2-phenyllevulinic acid (57.7 mg, 0.3 mmol) in a test tube. To the resultant mixture was added a solution of 1-hydroxybenzotriazole hydrate (33.8 mg, 0.25 mmol) in tetrahydrofuran (0.75 mL) followed by 1,3-diisopropylcarbodiimide (31.6 mg, 0.25 mmol). The reaction was stirred overnight. Methanol (3 mL) was added to ensure the reaction mixture was homogeneous. The mixture was purified by a SCX column as follows. The column was conditioned by rinsing with methanol (10 mL) and then pushing through air (10 mL). The reaction mixture was loaded onto the column. Air (10 mL) was pushed through the column followed by methanol (2×20 mL) and air (10 mL). Finally, the product was eluted with 2 N ammonia in methanol (6 mL) followed by air (10 mL). The solvent was removed from the sample by the use of a speed vacuum to give the two isomers of the title compound (56.5 mg, 97%) as an oil: HPLCb rt=3.73 and 3.92 LC/MS (electrospray, +ions) m/z 584(M+H).

EXAMPLE 65

Isomer A and Isomer B

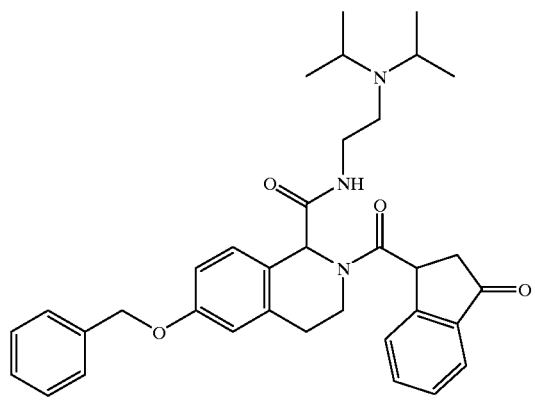

In a manner analogous to that of Example 64, the two isomers of the title compound were prepared from Part A compound from Example 46 (41.0 mg, 0.1 mmol) and 3-oxo-1-indancarboxylic acid (52.9 mg, 0.3 mmol) in yield of 55.2 mg (97%) as an oil: HPLCb rt=3.45 and 3.51 min; LC/MS (electrospray, +ions) m/z 568(M+H).

EXAMPLES 66 to 200

In a manner analogous to that of Examples 64 and 65, Examples 66–200 listed in the table below were prepared from Part A compound from Example 46 (0.1 mmol) and the respective carboxylic acid (0.3 mmol). A few compounds were purified by preparative HPLC, eluting with a gradient system of methanol and water with 0.2% trifluoroacetic acid. These compounds were isolated as trifluoroacetic acid salts.

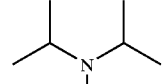

= X₁—R₁

| Example No. | X₁—R₁ | LC/MS (M + H)⁺ |
|---|---|---|
| 66 | 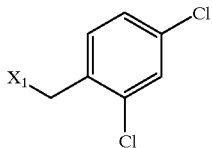 | 546 |
| 67 | 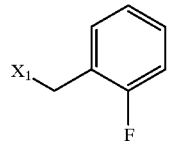 | 546 |
| 68 | 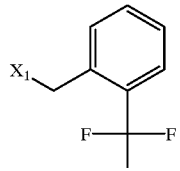 | 546 |
| 69 | 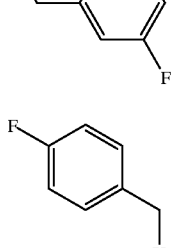 | 562 |

-continued

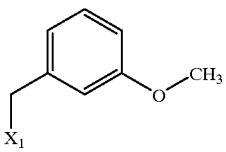

= X₁—R₁

| Example No. | X₁—R₁ | LC/MS (M + H)⁺ |
|---|---|---|
| 70 | 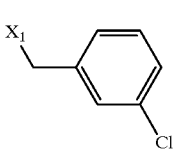 | 597 |
| 71 | 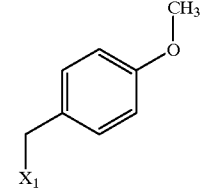 | 596 |
| 72 | 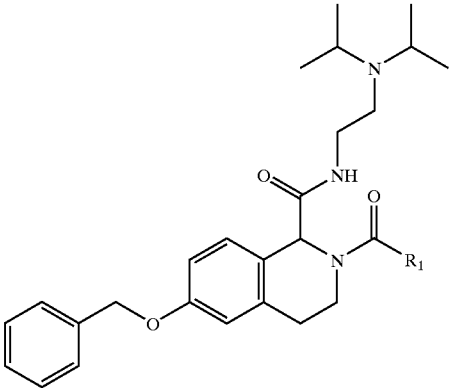 | 596 |
| 73 | 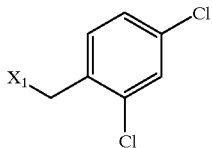 | 558 |
| 74 | 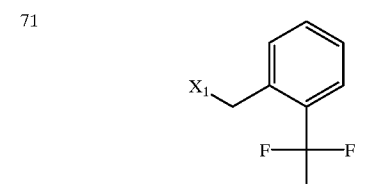 | 558 |
| 75 | 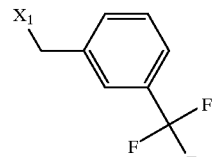 | 558 |

-continued
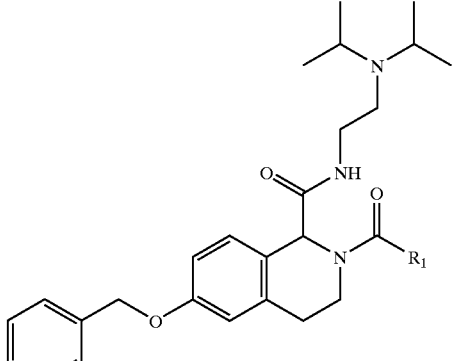
= X₁—R1
| Example No. | X₁—R1 | LC/MS (M + H)⁺ |
|---|---|---|
| 76 | 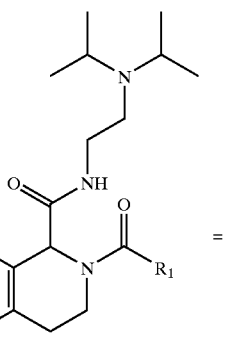 | 618 |
| 77 | 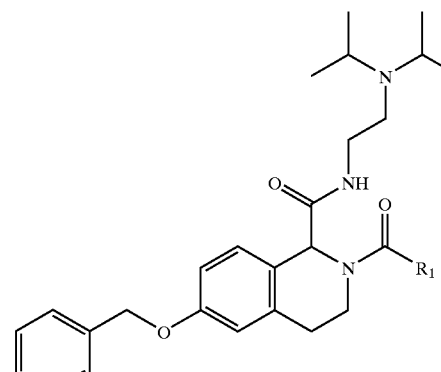 | 572 |
| 78 | 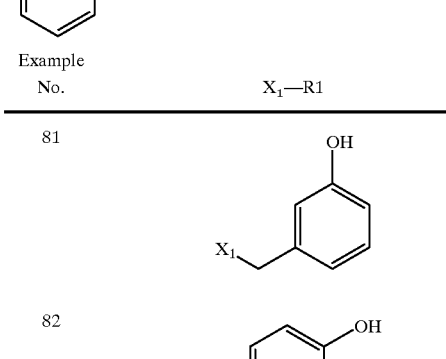 | 634 |
| 79 | 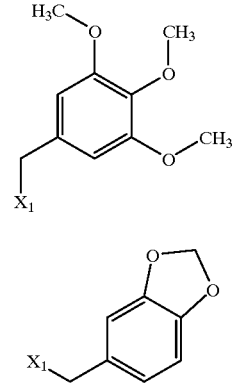 | 634 |
| 80 | 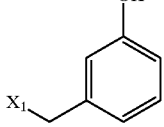 | 544 |
-continued
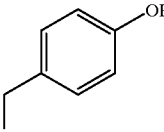
= X₁—R1
| Example No. | X₁—R1 | LC/MS (M + H)⁺ |
|---|---|---|
| 81 | 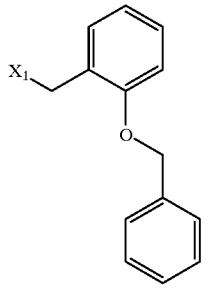 | 544 |
| 82 | 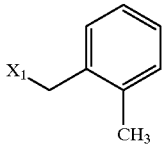 | 544 |
| 83 | 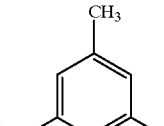 | 542 |
| 84 | 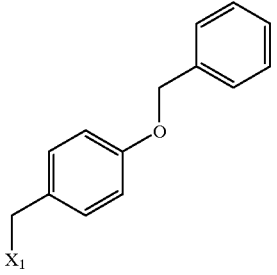 | 556 |
| 85 | 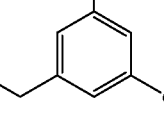 | 570 |
| 86 | 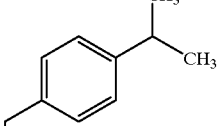 | 604 |

-continued

[Structure: 6-benzyloxy-1,2,3,4-tetrahydroisoquinoline-1-carboxamide with N-(2-(diisopropylamino)ethyl) amide and N2-C(O)-R1 group] = X₁—R1

| Example No. | X₁—R1 | LC/MS (M + H)⁺ |
|---|---|---|
| 87 | X₁-CH₂-(3-nitrophenyl) | 573 |
| 88 | X₁-CH₂-(4-nitrophenyl) | 573 |
| 89 | X₁-CH₂-(4-methylthiophenyl) | 574 |
| 90 | X₁-CHF-phenyl | 546 |
| 91 | X₁-CH(CH₃)-phenyl | 542 |

-continued

[Same core structure] = X₁—R1

| Example No. | X₁—R1 | LC/MS (M + H)⁺ |
|---|---|---|
| 92 | X₁-CH(2-methylphenyl)-(CH₂)₄-CH₃ | 612 |
| 93 | X₁-CH(OH)-phenyl | 544 |
| 94 | X₁-CH(OCH₃)-phenyl | 558 |
| 95 | X₁-CH(phenyl)-CH₂OH | 558 |
| 96 | X₁-CH(pyridyl)-CH₂-C(O)-phenyl | 646 |

-continued
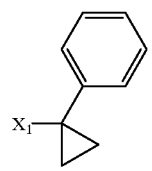
= X₁—R1
| Example No. | X₁—R1 | LC/MS (M + H)⁺ |
|---|---|---|
| 97 | 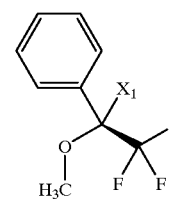 | 554 |
| 98 | 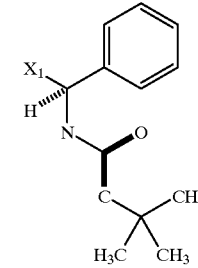 | 626 |
| 99 | 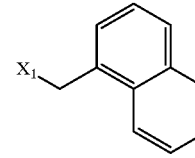 | 643 |
| 100 | 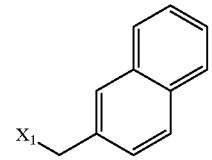 | 578 |
| 101 | 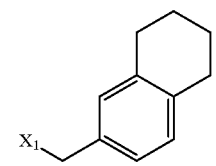 | 578 |
-continued
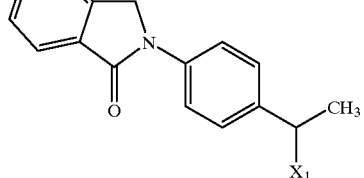
= X₁—R1
| Example No. | X₁—R1 | LC/MS (M + H)⁺ |
|---|---|---|
| 102 | 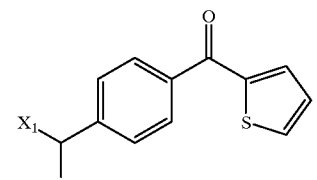 | 582 |
| 103 | 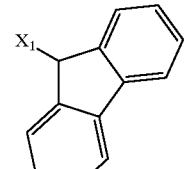 | 673 |
| 104 | 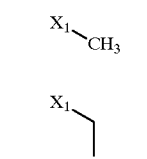 | 652 |
| 105 | 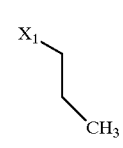 | 602 |
| 106 | X₁—CH₃ | 452 |
| 107 | X₁—CH₂CH₃ | 466 |
| 108 | X₁—CH₂CH₂CH₃ | 480 |

-continued
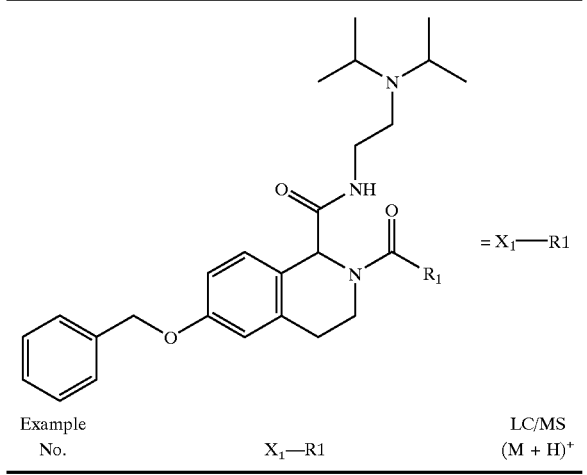
= X₁—R1
| Example No. | X₁—R1 | LC/MS (M + H)⁺ |
|---|---|---|
| 109 | isopropyl | 480 |
| 110 | tert-butyl | 494 |
| 111 | PhCH(NHBoc)– | 643 |
| 112 | 2-chlorophenethyl | 576 |
| 113 | (4-chloro-substituted phenethyl) | 576 |
| 114 | 2-chlorobenzyl-CH₂ | 556 |
-continued
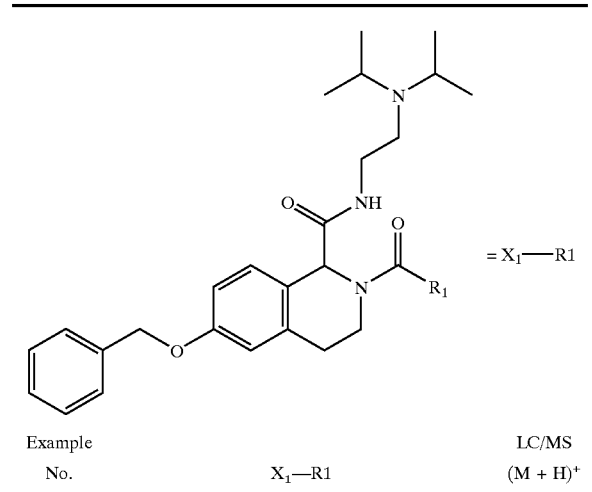
= X₁—R1
| Example No. | X₁—R1 | LC/MS (M + H)⁺ |
|---|---|---|
| 115 | 3-methylphenethyl | 556 |
| 116 | 4-methylphenethyl | 556 |
| 117 | 2-methoxyphenethyl | 572 |
| 118 | 3-methoxyphenethyl | 572 |
| 119 | 4-methoxyphenethyl | 572 |

-continued

[Structure: tetrahydroisoquinoline with 6-benzyloxy, 1-carboxamide-N-CH2CH2-N(iPr)2, 2-C(O)-R1] = X₁—R1

| Example No. | X₁—R1 | LC/MS (M + H)⁺ |
|---|---|---|
| 120 | X₁-CH2CH2-(2,5-dimethoxyphenyl) | 602 |
| 121 | X₁-CH2CH2-(2,3-dimethoxyphenyl) | 602 |
| 122 | X₁-CH2CH2-(3,4-dimethoxyphenyl) | 602 |
| 123 | X₁-CH2CH2-(3,4,5-trimethoxyphenyl) | 632 |
| 124 | X₁-CH2CH2-(3,4-methylenedioxyphenyl) | 586 |

-continued

[Same core structure] = X₁—R1

| Example No. | X₁—R1 | LC/MS (M + H)⁺ |
|---|---|---|
| 125 | X₁-CH2CH2-(2-hydroxyphenyl) | 558 |
| 126 | X₁-CH2CH2-(3-hydroxyphenyl) | 558 |
| 127 | X₁-CH2CH2-(4-hydroxyphenyl) | 558 |
| 128 | X₁-CH2CH2-(2,4-dihydroxyphenyl) | 574 |
| 129 | X₁-CH2CH2-(3,4-dihydroxyphenyl) | 574 |
| 130 | X₁-CH2CH2-(3-trifluoromethylphenyl) | 610 |

-continued
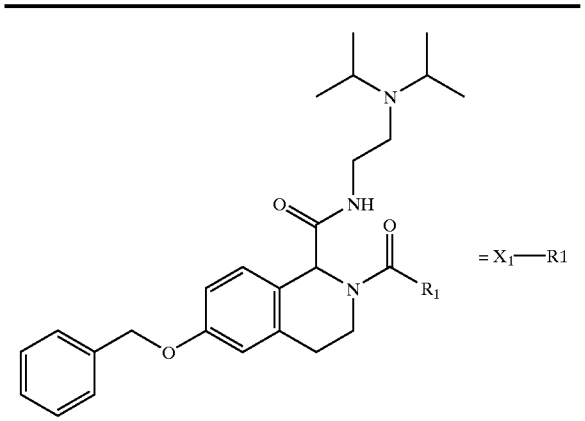
= X₁—R1
| Example No. | X₁—R1 | LC/MS (M + H)⁺ |
|---|---|---|
| 131 | 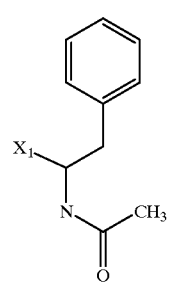 | 599 |
| 132 | 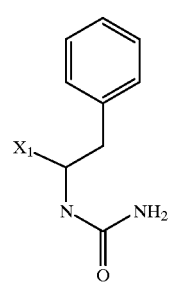 | 600 |
| 133 | 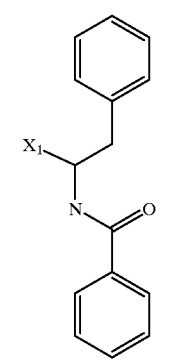 | 661 |
-continued
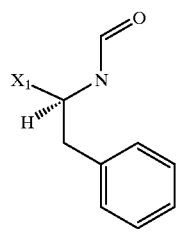
= X₁—R1
| Example No. | X₁—R1 | LC/MS (M + H)⁺ |
|---|---|---|
| 134 | 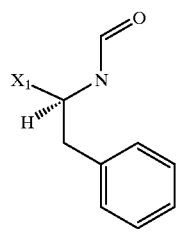 | 585 |
| 135 | 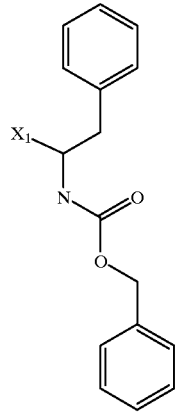 | 691 |
| 136 | 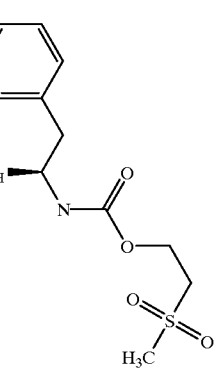 | 707 |

-continued
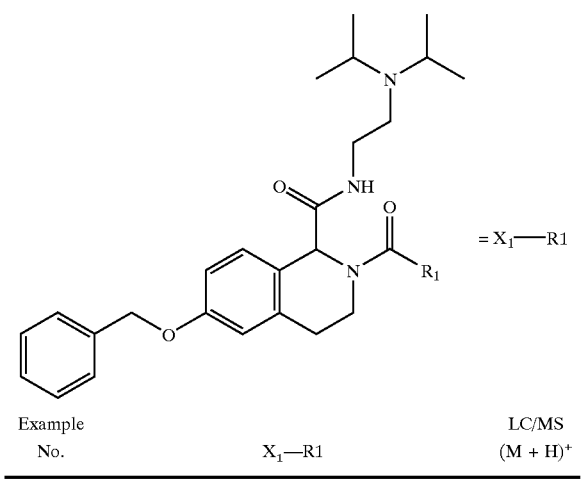
= X₁—R1
| Example No. | X₁—R1 | LC/MS (M + H)⁺ |
|---|---|---|
| 137 | | 711 |
| 138 | | 687 |
| 139 | | 558 |
| 140 | | 556 |
| 141 | | 556 |
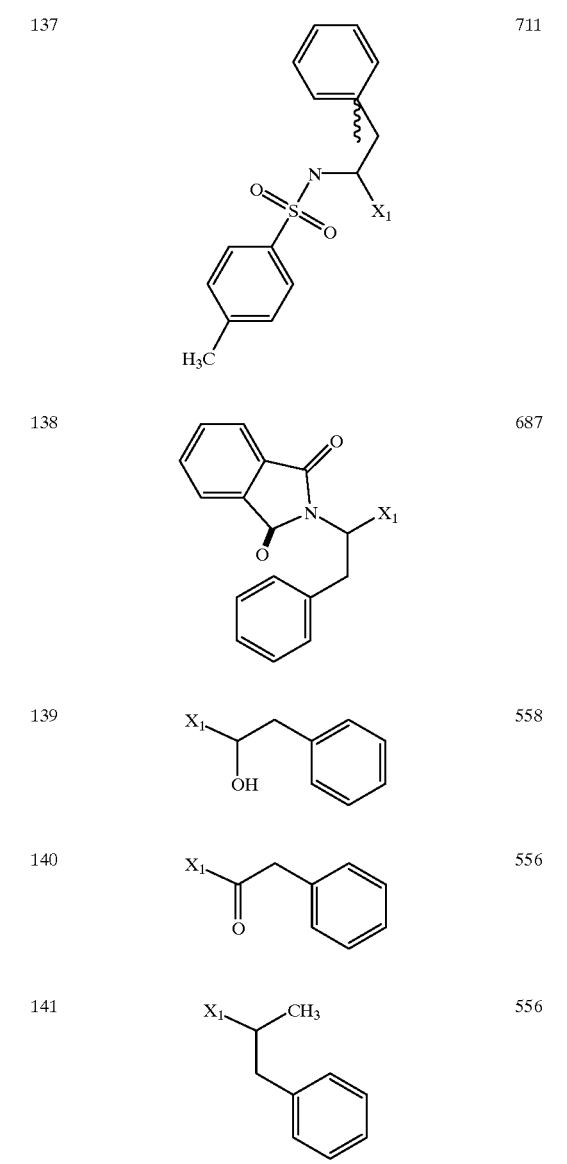
-continued
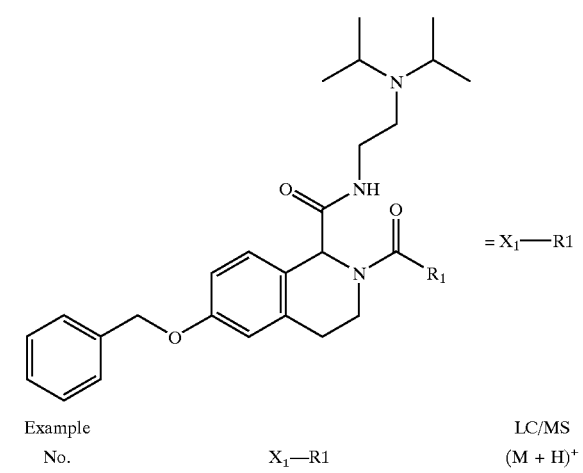
= X₁—R1
| Example No. | X₁—R1 | LC/MS (M + H)⁺ |
|---|---|---|
| 142 | | 556 |
| 143 | | 601 |
| 144 | | 602 |
| 145 | | 572 |
| 146 | | 584 |
| 147 | | 584 |
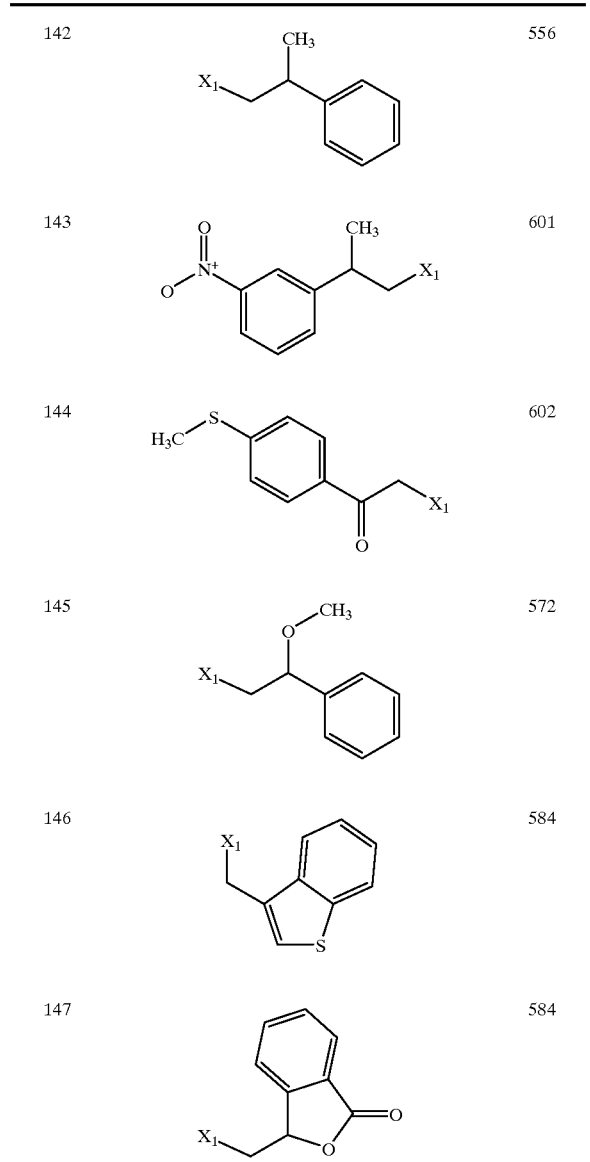

91
-continued
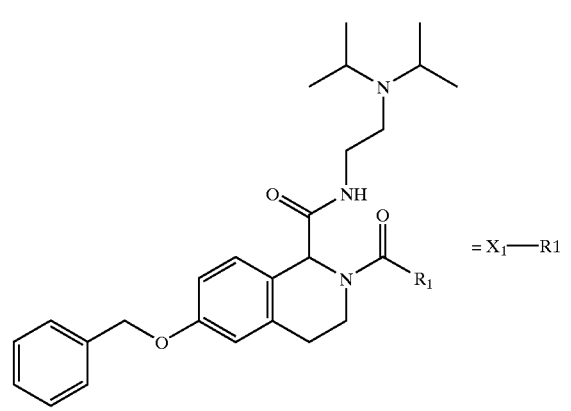
= X₁—R1
| Example No. | X₁—R1 | LC/MS (M + H)⁺ |
|---|---|---|
| 148 | 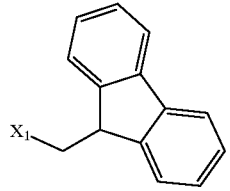 | 616 |
| 149 | 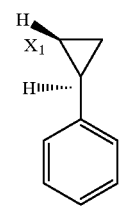 | 554 |
| 150 | 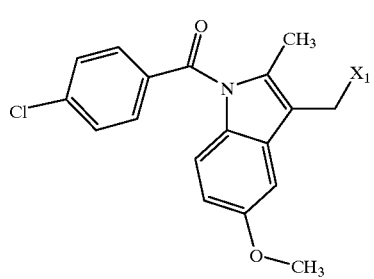 | 749 |
| 151 | 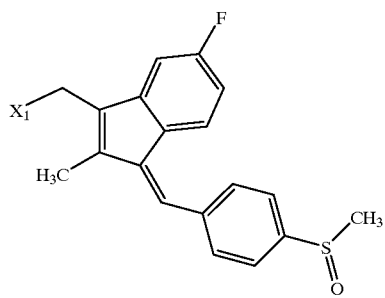 | 748 |
92
-continued
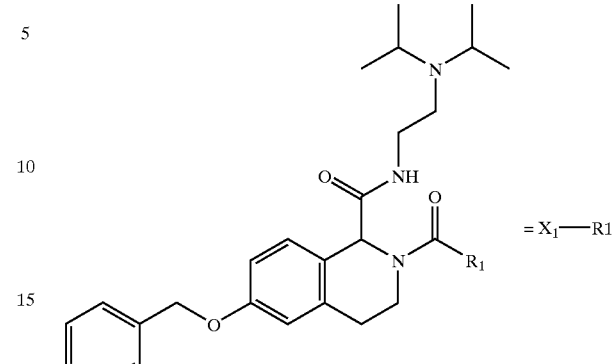
= X₁—R1
| Example No. | X₁—R1 | LC/MS (M + H)⁺ |
|---|---|---|
| 152 | 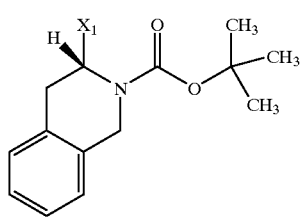 | 669 |
| 153 | 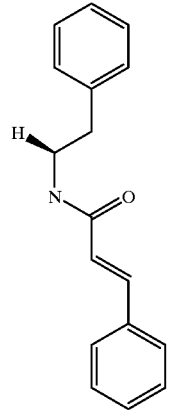 | 637 |
| 154 | 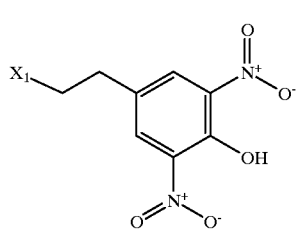 | 648 |
| 155 | 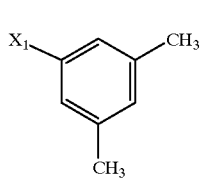 | 542 |

= X₁—R1

| Example No. | X₁—R1 | LC/MS (M + H)⁺ |
|---|---|---|
| 156 | X₁—C₆H₄—OH (4-hydroxyphenyl) | 530 |
| 157 | X₁-(2-biphenyl) | 590 |
| 158 | X₁—C₆H₄—CH₂—C₆H₅ (2-benzylphenyl) | 604 |
| 159 | X₁-(2-naphthyl) | 564 |
| 160 | X₁-(1-naphthyl) | 564 |
| 161 | X₁-(2,3-dimethoxyphenyl) | 574 |
| 162 | X₁-(2-phenoxyphenyl) | 606 |
| 163 | X₁-(2-methoxyphenyl) | 558 |
| 164 | X₁—C₆H₄—OCF₃ (4-trifluoromethoxyphenyl) | 598 |
| 165 | X₁-(2,3-dihydrobenzofuran-5-yl) | 556 |

-continued
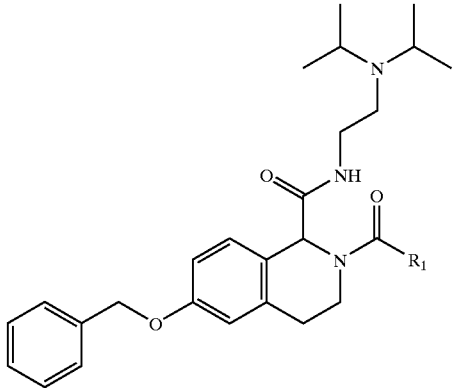
= X₁—R1
| Example No. | X₁—R1 | LC/MS (M + H)⁺ |
|---|---|---|
| 166 | 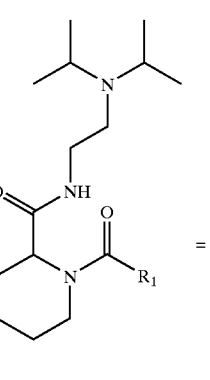 | 606 |
| 167 | 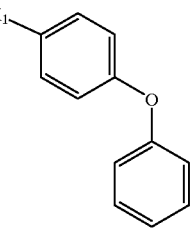 | 558 |
| 168 | 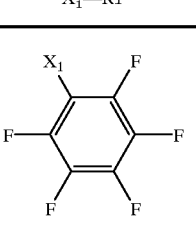 | 620 |
| 169 | 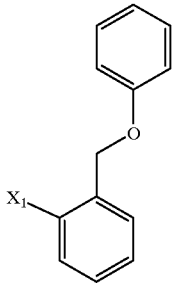 | 606 |
| 170 | 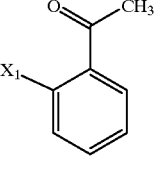 | 532 |
-continued
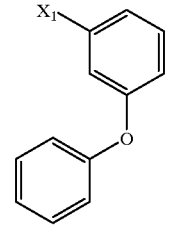
= X₁—R1
| Example No. | X₁—R1 | LC/MS (M + H)⁺ |
|---|---|---|
| 171 | 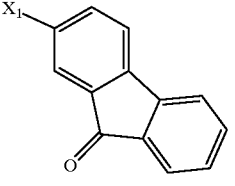 | 604 |
| 172 | 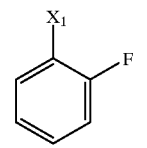 | 556 |
| 173 | 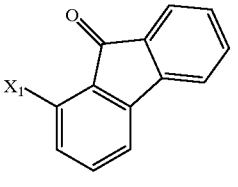 | 616 |
| 174 | 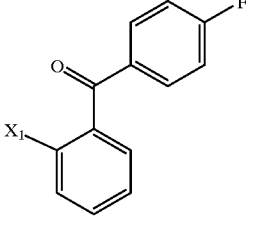 | 616 |
| 175 |  | 636 |

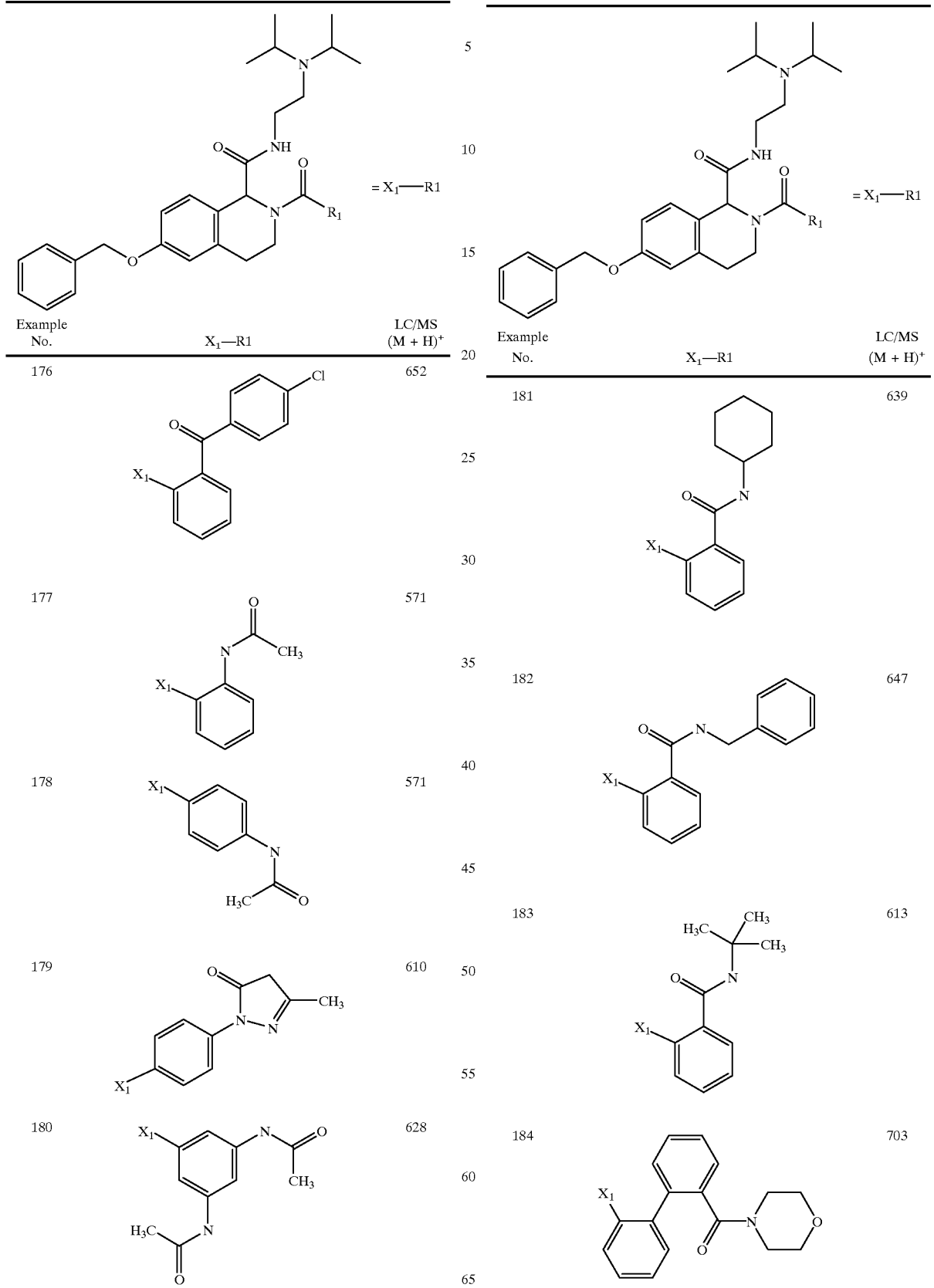

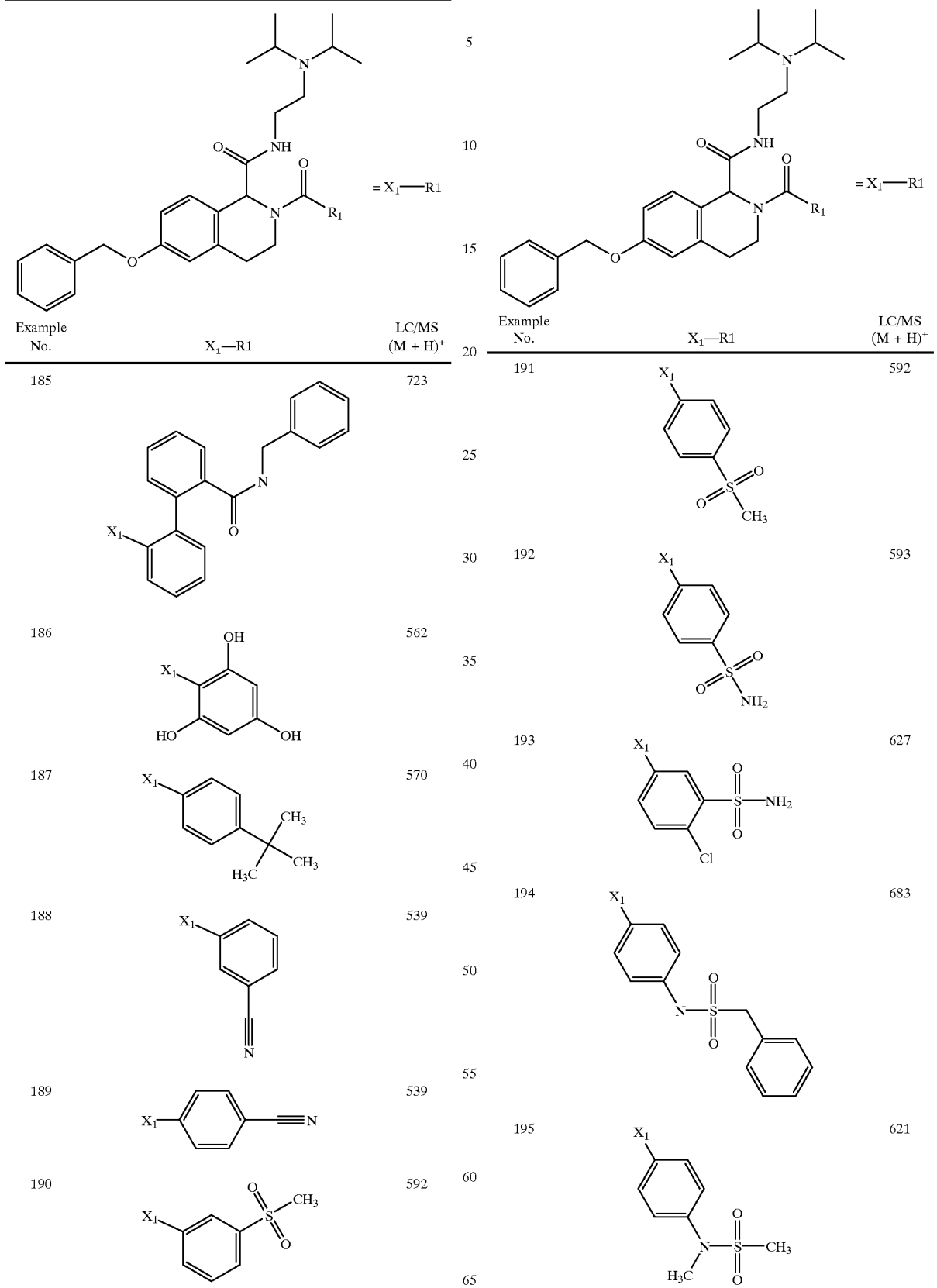

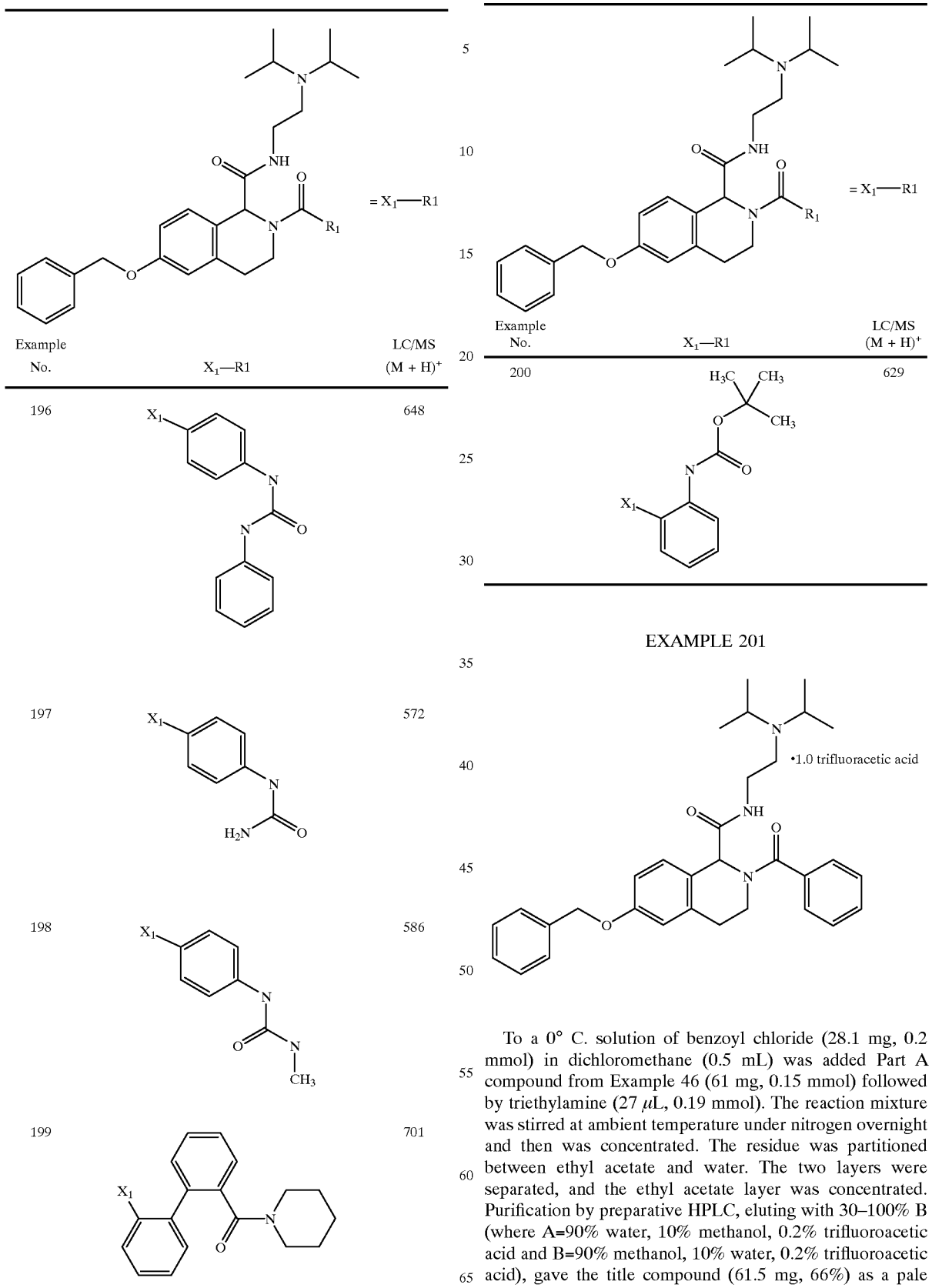

EXAMPLE 201

To a 0° C. solution of benzoyl chloride (28.1 mg, 0.2 mmol) in dichloromethane (0.5 mL) was added Part A compound from Example 46 (61 mg, 0.15 mmol) followed by triethylamine (27 μL, 0.19 mmol). The reaction mixture was stirred at ambient temperature under nitrogen overnight and then was concentrated. The residue was partitioned between ethyl acetate and water. The two layers were separated, and the ethyl acetate layer was concentrated. Purification by preparative HPLC, eluting with 30–100% B (where A=90% water, 10% methanol, 0.2% trifluoroacetic acid and B=90% methanol, 10% water, 0.2% trifluoroacetic acid), gave the title compound (61.5 mg, 66%) as a pale yellow semi-solid/oil: LC/MS (electrospray, +ions) m/z 514 (M+H).

EXAMPLES 202 to 214

In a manner analogous to that of Example 201, Examples 202–214 in the table below were prepared from Part A compound from Example 46 and the respective acid chloride, sulfonyl chloride, sulfamoyl chloride.

| Example No. | $X_1$—X3—R1 | LC/MS (M + H)+ |
|---|---|---|
| 202 | PhCH$_2$C(=O)—X$_1$ | 528 |
| 203 | PhCH$_2$CH$_2$C(=O)—X$_1$ | 542 |
| 204 | (CH$_3$)$_3$CCH$_2$C(=O)—X$_1$ | 508 |
| 205 | CH$_3$SO$_2$—X$_1$ | 488 |
| 206 | CH$_3$CH$_2$SO$_2$—X$_1$ | 502 |
| 207 | CH$_3$CH$_2$CH$_2$SO$_2$—X$_1$ | 516 |
| 208 | CH$_3$(CH$_2$)$_3$SO$_2$—X$_1$ | 530 |
| 209 | PhSO$_2$—X$_1$ | 550 |
| 210 | PhCH$_2$SO$_2$—X$_1$ | 564 |
| 211 | PhCH=CHSO$_2$—X$_1$ | 576 |

EXAMPLES 215 to 229

Examples 215–229 were prepared by methods described in earlier examples and by methods known in the art starting from Part A compound from Example 46 and the corresponding carboxylic acid.

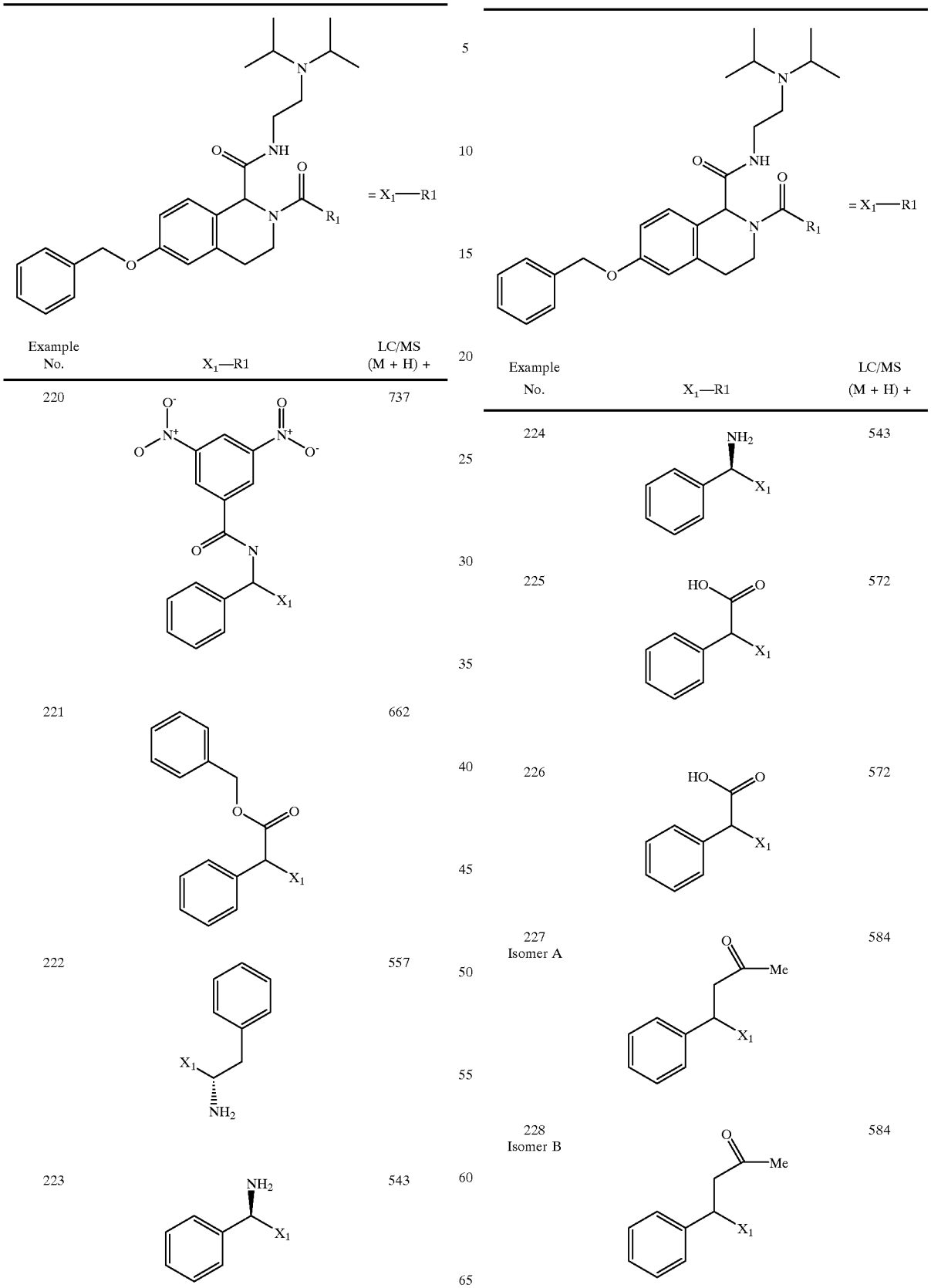

-continued

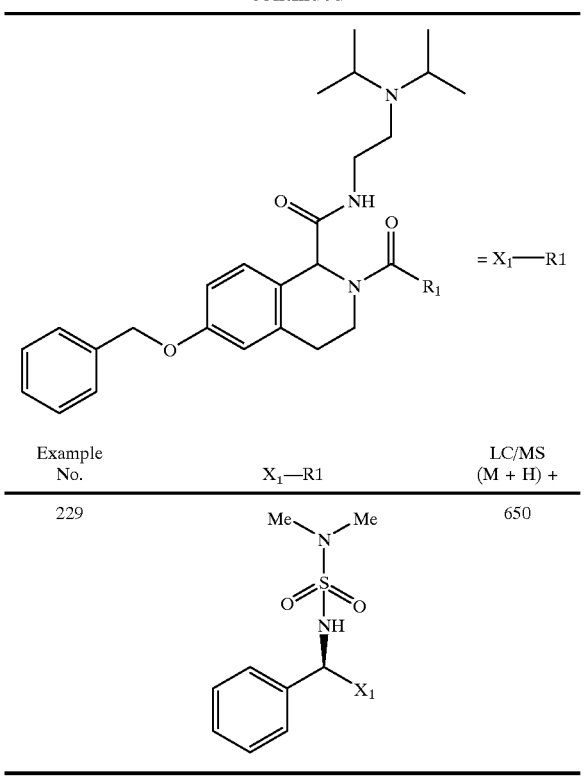

| Example No. | X₁—R1 | LC/MS (M + H) + |
|---|---|---|
| 229 | 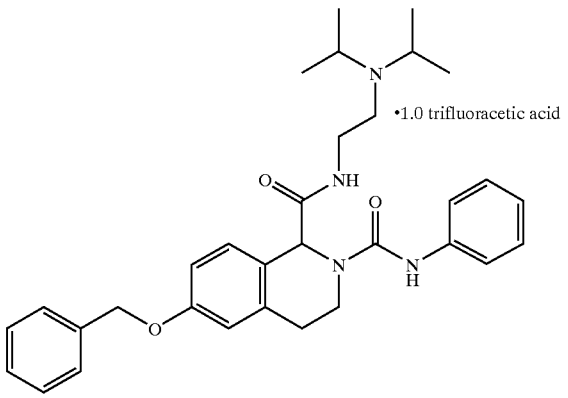 | 650 |

EXAMPLE 230

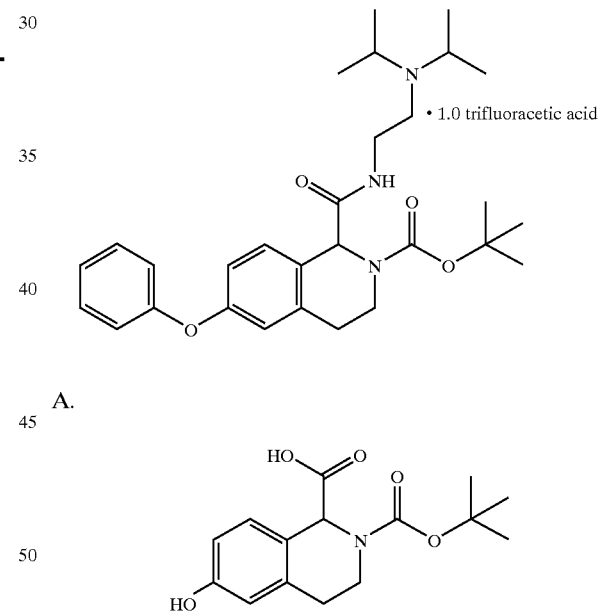

To a solution of Part A compound from Example 46 (61 mg, 0.15 mmol) in dichloromethane (0.5 mL) was added phenyl isocyanate (19.7 mg, 0.165 mmol) via a syringe. Additional dichloromethane (0.5 mL) was added. The reaction mixture was stirred overnight, and then it was concentrated. Purification on preparative HPLC, eluting with a gradient system of 30–100% B (where A=90% water, 10% methanol, 0.2% trifluoroacetic acid and B=90% methanol, 10% water, 0.2% trifluoroacetic acid), gave the title compound (81 mg, 85%) as a white foam: HPLCb rt=3.70 min.; LC/MS (electrospray, +ions) m/z 529 (M+H).

EXAMPLE 231

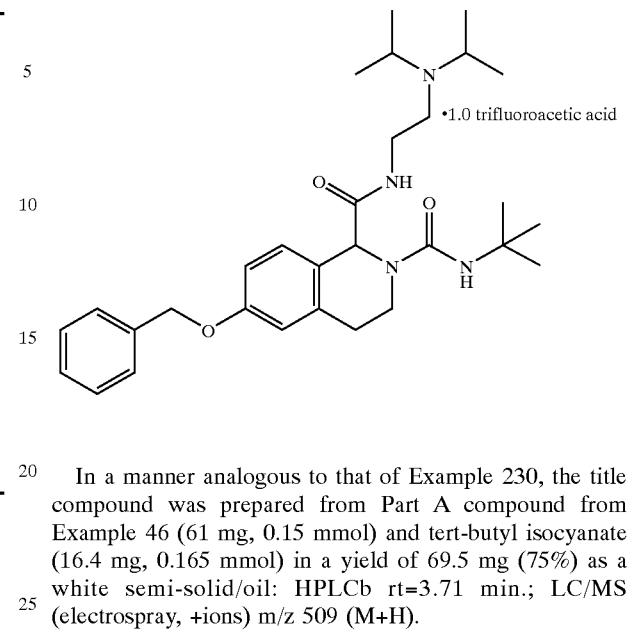

In a manner analogous to that of Example 230, the title compound was prepared from Part A compound from Example 46 (61 mg, 0.15 mmol) and tert-butyl isocyanate (16.4 mg, 0.165 mmol) in a yield of 69.5 mg (75%) as a white semi-solid/oil: HPLCb rt=3.71 min.; LC/MS (electrospray, +ions) m/z 509 (M+H).

EXAMPLE 232

A.

To a solution of Part C compound from Example 1 (1.00 g, 3.25 mmol) in methanol (1 mL) and tetrahydrofuran (1 mL) was added a solution of sodium hydroxide (260 mg, 6.5 mmol) in water (650 μL). The reaction was stirred overnight at ambient temperature, heated at 60° C. for 6 h and then stirred at ambient temperature overnight. The solvent was removed in vacuo, and the residue was partitioned between water and ethyl acetate. The aqueous layer was separated and acidified with 6 N hydrochloric acid solution to pH~3 and extracted with ethyl acetate (2×) The organic layers were dried over sodium sulfate and the mixture was filtered. The filtrate was concentrated to give the title compound (930 mg, 97.5%) as a clear oil, which became a white foam.

B.

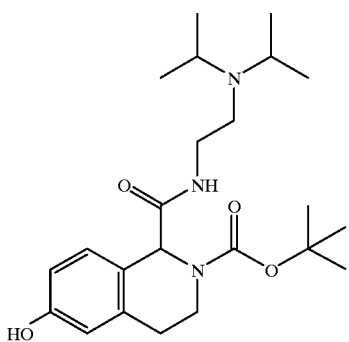

To a solution of Part A compound (500 mg, 1.7 mmol) and diisopropylethylenediamine (326 μL, 1.9 mmol) in dimethylformamide (10 mL) was added diisopropylethylamine (890 μL, 5.1 mmol) followed by 1-hydroxy-7-azabenzotriazole (325 mg, 2.4 mmol) and 1-(3-dimethylaminopropyl)-3-ethylcarbodiimide hydrochloride (327 mg, 1.7 mmol). After stirring the reaction mixture overnight, the mixture was partitioned between ethyl acetate and saturated aqueous sodium bicarbonate solution. The organic layer was washed with water (2×) and brine, and then dried over sodium sulfate. The mixture was filtered and the filtrate concentrated in vacuo to give the title product (587 mg, 82.1%) as a white foam.

C.

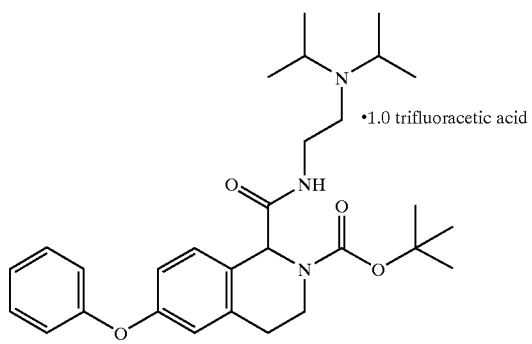

•1.0 trifluoracetic acid

To a slurry of Part B compound (50 mg, 0.12 mmol), phenyl boronic acid (29 mg, 0.24 mmol), copper(II) acetate (22 mg, 0.12 mmol) and 4 Å powdered molecular sieves in dichloromethane (1.2 mL) was added pyridine (48 pL, 0.60 mmol). The reaction was stirred overnight and then was filtered. The filtrate was concentrated to a green oil that was purified by preparative HPLC. The title compound (59 mg, 81%) was obtained as a yellow oil: : HPLCa1 rt=2.2 min.; LC/MS (electrospray, +ions) m/z 496 (M+H).

EXAMPLE 233

Isomer A and Isomer B

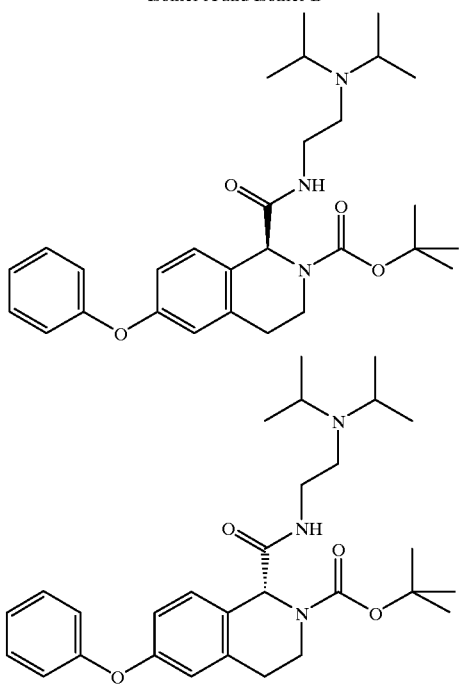

Title compound, Example 232 (70 mg) was resolved on Chiralpak AD column (50×500 mm), eluting with 20% isopropanol/hexanes to give the title compounds, Isomer A (28 mg) and Isomer B (30 mg).

EXAMPLES 234 to 245

In a manner analogous to that of Example 232, Examples 234–245 compounds listed in the table below were prepared from Part B compound from Example 232 (0.12 mmol) and the respective phenylboronic acid (0.24 mmol). A few compounds were purified by preparative HPLC, eluting with a gradient system of methanol and water with 0.2% trifluoroacetic acid. These compounds were isolated as trifluoroacetic acid salts.

| Example No. | $X_1$—R2 | LC/MS (M + H) + |
|---|---|---|
| 234 | $X_1$—⟨benzene⟩—Cl | 531 |

-continued
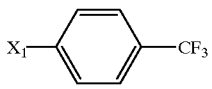
| Example No. | X₁—R2 | LC/MS (M + H)+ |
|---|---|---|
| 235 | 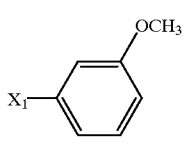 | 564 |
| 236 | 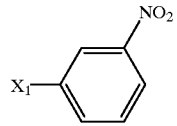 | 541 |
| 237 | 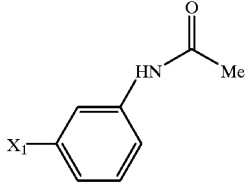 | 526 |
| 238 | 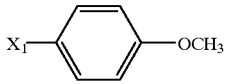 | 565 |
| 239 | 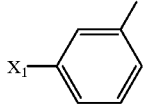 | 542 |
| 240 | 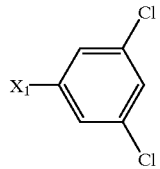 | 524 |
| 241 | 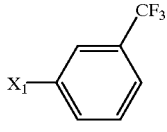 | 524 |
-continued
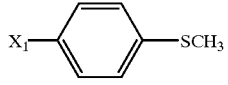
| Example No. | X₁—R2 | LC/MS (M + H)+ |
|---|---|---|
| 242 | 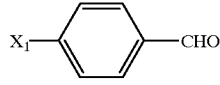 | 526 |
| 243 | 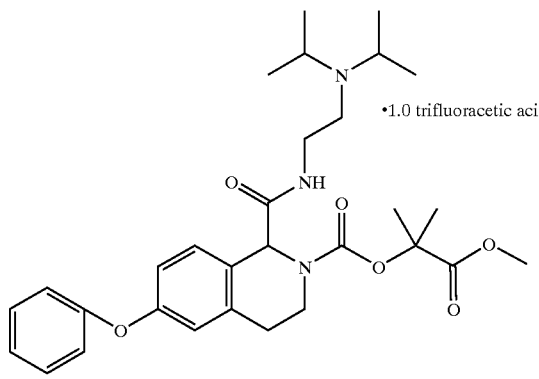 | 553 |
| 244 | 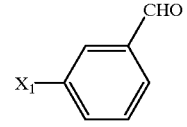 | 514 |
| 245 | | 564 |
EXAMPLE 246

A.

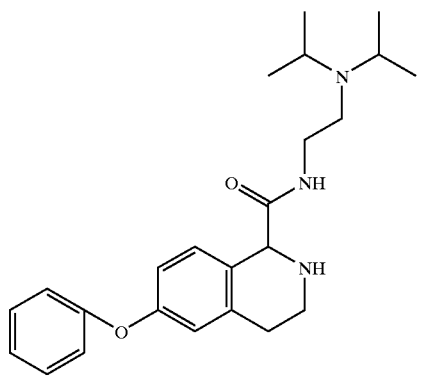

To neat title compound from Example 232 (1.56 g, 3.15 mmol) is added 4N hydrogen chloride (7 mL, dioxane solution) at room temperature. After 3 h, the volatiles were removed in vacuo, the residue redissolved in ethyl acetate and the pH adjusted to 8 with 1N sodium hydroxide. The organic layer was dried and concentrated to give the title compound (1.11 g) as a yellow colored oil. LC/MS (electrospray, +ions) m/z 396(M+H).

B.

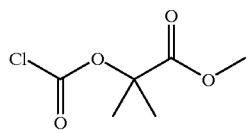

To a 0° C. solution of methyl 2-hydroxyisobutyrate (236 mg, 2.0 mmol) and triethylamine (202 mg, 2.0 mmol) in tetrahydrofuran (5 mL) was added 1.9 M phosgene in toluene (1.68 mL, 3.2 mmol). After stirring for 2 h between −5 to 0° C., the reaction mixture was concentrated and used in the next procedure without purification.

C.

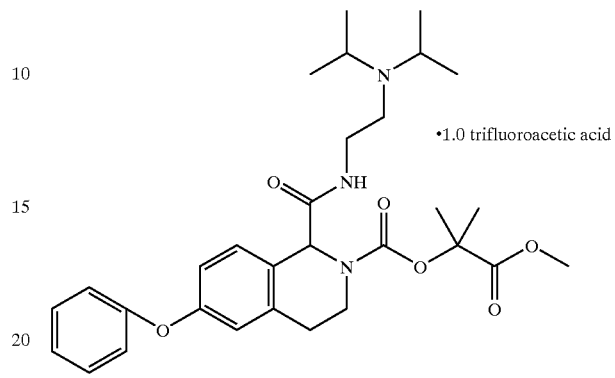

At 0° C., a solution of Part B compound (2.0 mmol) in dichloromethane (5 mL) was treated with Part A compound (118.9 mg, 0.30 mmol) followed by triethylamine (101.2 mg, 1.0 mmol). The reaction mixture was stirred at 0° C. to 5° C. for 2 h and then concentrated. Purification by preparative HPLC, eluting with a gradient system of 40–100% B (where A=90% water, 10% methanol, 0.2% trifluoroacetic acid and B=90% methanol, 10% water, 0.2% trifluoroacetic acid), gave the title compound (115.3 mg) as a yellow oil; LC/MS (electrospray, +ions) m/z 540 (M+H).

EXAMPLES 247 to 250

Examples 247–250 listed below can were prepared as shown in Scheme 11 and employing the procedures described above, the working examples, and methods known in the arts.

| Example No. | Structure | LC/MS (M + H) + |
|---|---|---|
| 247 | (structure shown) | 510 |

-continued

| Example No. | Structure | LC/MS (M + H) + |
|---|---|---|
| 248 | [Structure: 7-benzyloxy-tetrahydroisoquinoline with N-SO2-NMe2, C(O)NH-CH2CH2-N(iPr)2] | 517 |
| 249 | [Structure: 7-phenoxy-tetrahydroisoquinoline with N-SO2-NMe2, C(O)NH-CH2CH2-N(iPr)2] | 503 |

Examples listed below can be prepared from intermediate Part A compound from Example 46 and an alkyl halide:

| Example No. | Structure | LC/MS (M + H) + |
|---|---|---|
| 250 | [Structure: 6-benzyloxy-tetrahydroisoquinoline with N-CH2-C(O)-O-tBu, C(O)NH-CH2CH2-N(iPr)2] | 524 |

Examples listed in the Table below can be prepared employing the procedures described above, the working examples, and methods known in the arts.

| Example No. | Structure | LC/MS (M + H)+ |
|---|---|---|
| 251 | 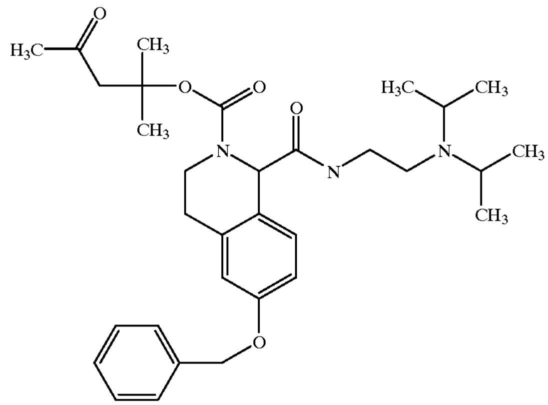 | 552 |
| 252 | 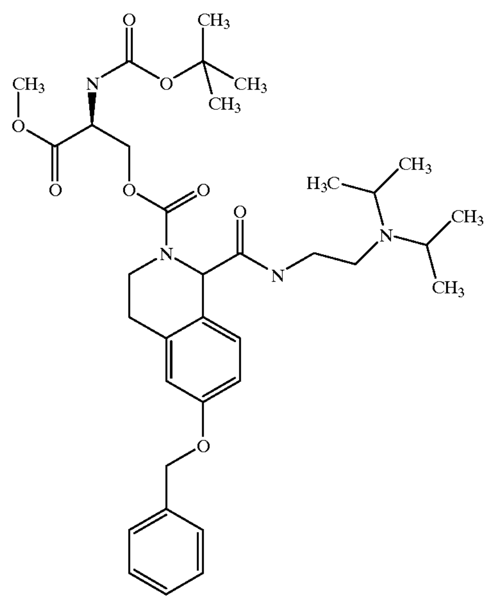 | 655 |
| 253 | 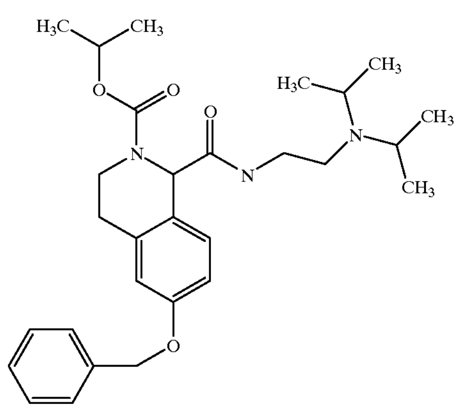 | 496 |

-continued

| Example No. | Structure | LC/MS (M + H) + |
|---|---|---|
| 254 | 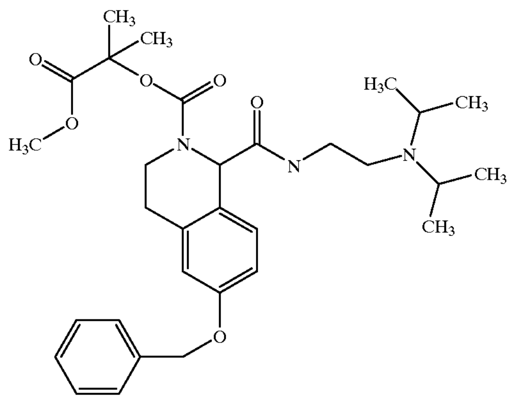 | 554 |
| 255 | 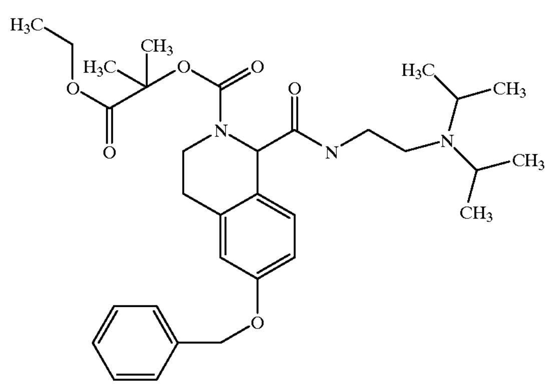 | 568 |
| 256 | 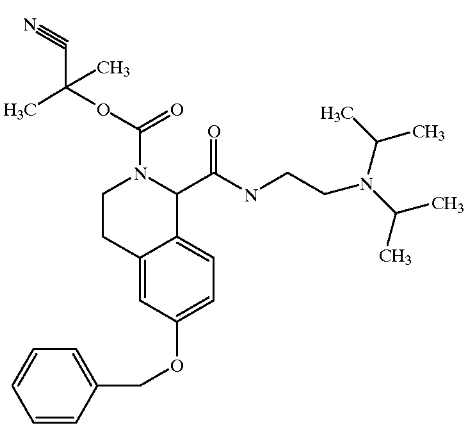 | 521 |

-continued

| Example No. | Structure | LC/MS (M + H) + |
|---|---|---|
| 257 | 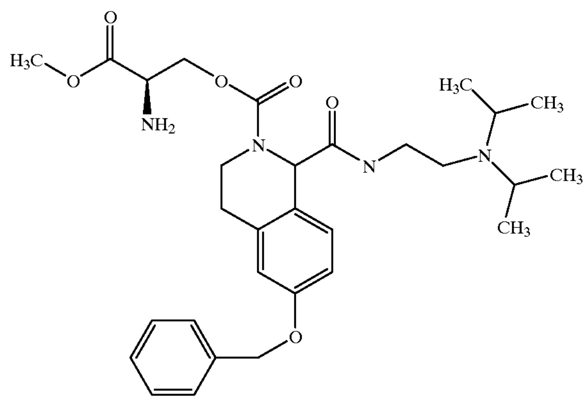 | 555 |
| 258 Isomer A | 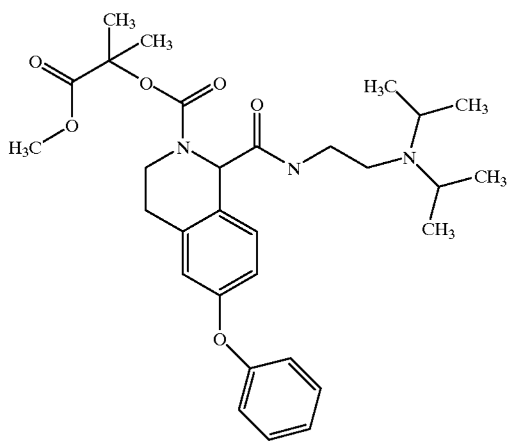 | 540 |
| 259 Isomer B | 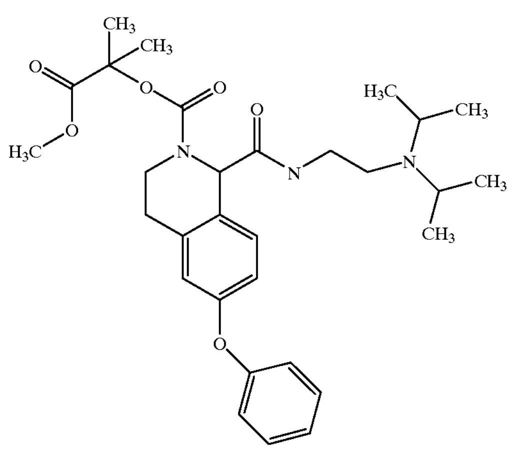 | 540 |

-continued

| Example No. | Structure | LC/MS (M + H) + |
|---|---|---|
| 260 | 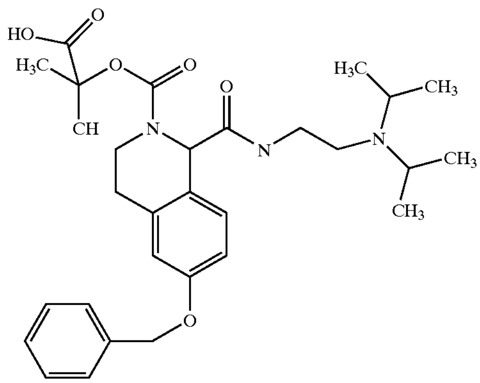 | 540 |
| 261 | 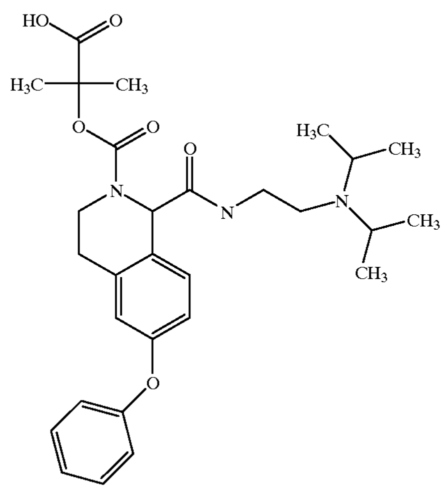 | 526 |
| 262 | 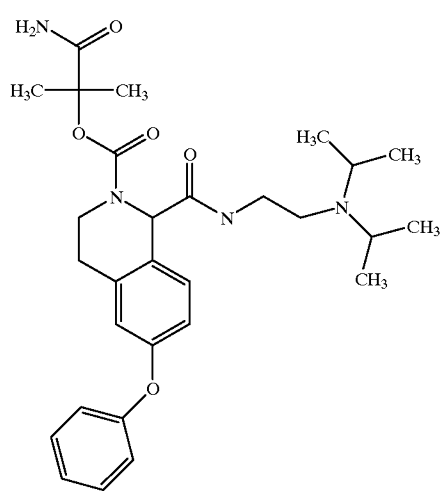 | 525 |

-continued

| Example No. | Structure | LC/MS (M + H) + |
|---|---|---|
| 263 | 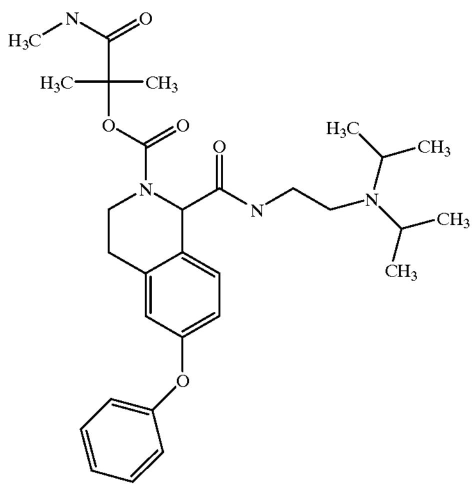 | 539 |
| 264 | 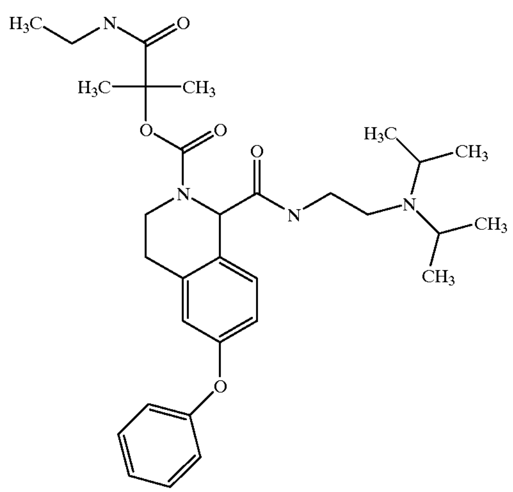 | 553 |
| 265 | 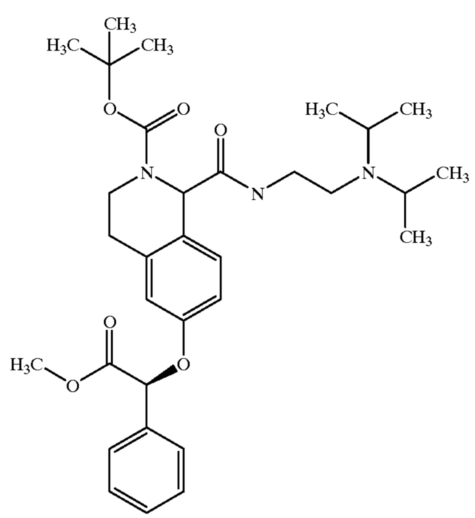 | 568 |

-continued

| Example No. | Structure | LC/MS (M + H) + |
|---|---|---|
| 266 Diastereomer A | 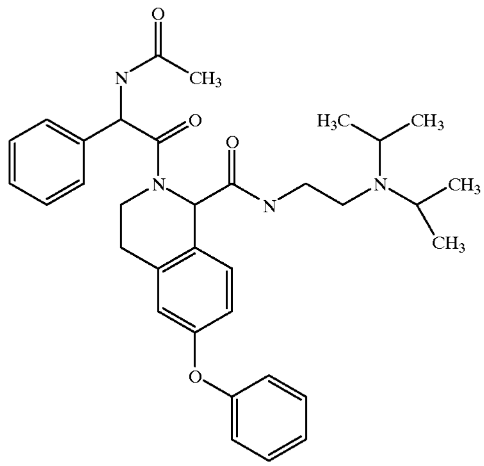 | 571 |
| 267 Diastereomer B | 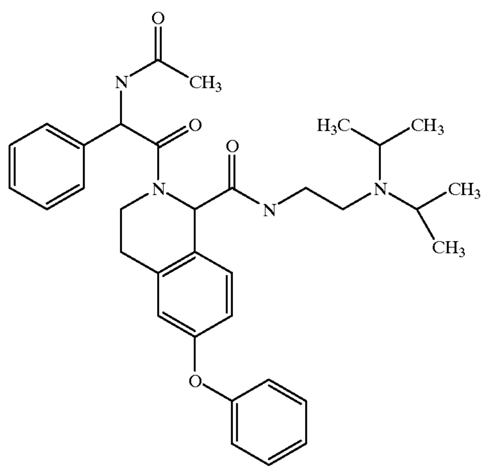 | 571 |
| 268 Diastereomer A | 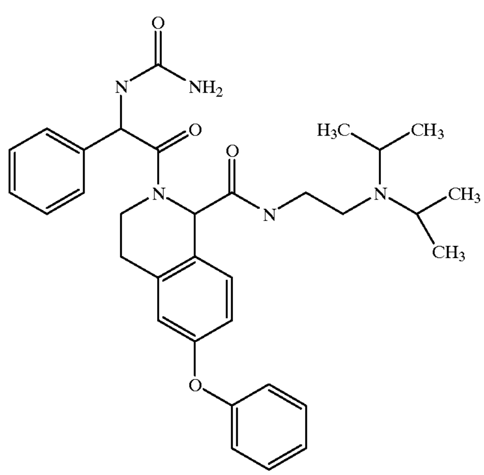 | 572 |

-continued

| Example No. | Structure | LC/MS (M + H) + |
|---|---|---|
| 269 Diastereomer B | 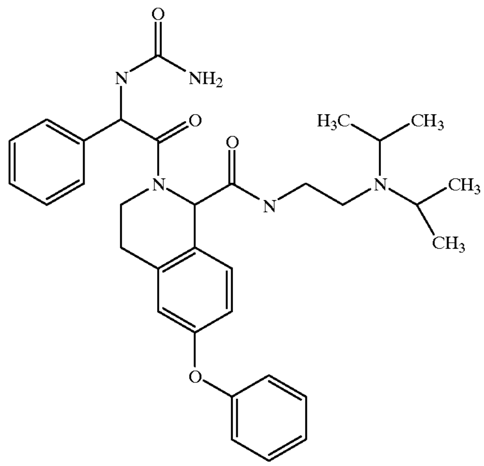 | 572 |
| 270 Diastereomer A | 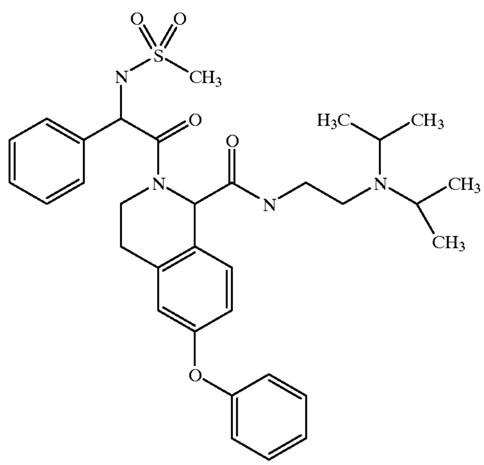 | 607 |
| 271 Diastereomer B | 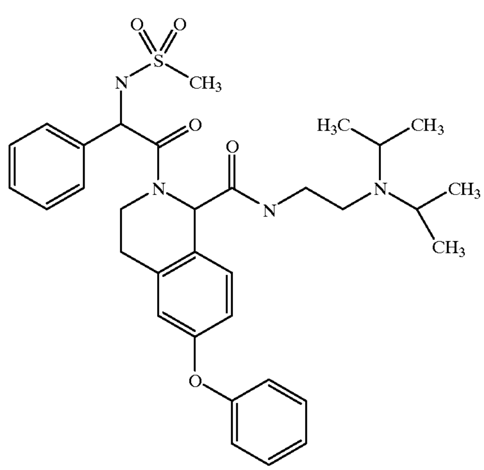 | 607 |

| Example No. | Structure | LC/MS (M + H) + |
|---|---|---|
| 272 Diastereomer A | 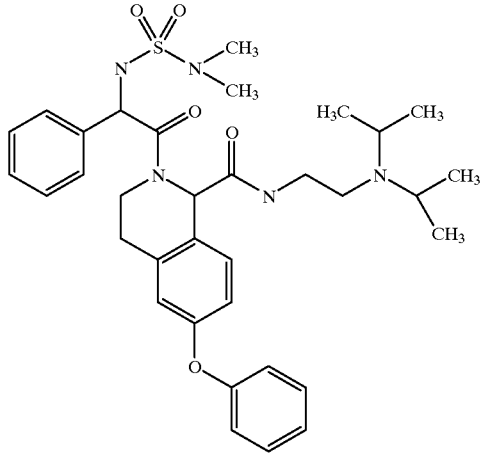 | 636 |
| 273 Diastereomer B | 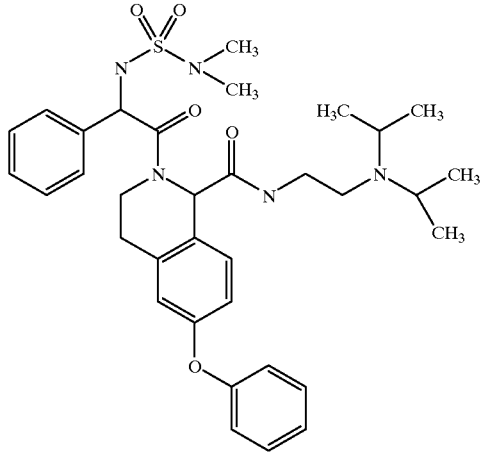 | 636 |
| 274 Diastereomer A | 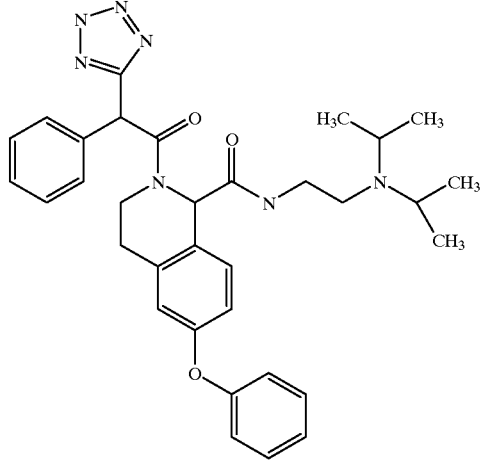 | 582 |

-continued
| Example No. | Structure | LC/MS (M + H) + |
|---|---|---|
| 275 Diastereomer B | 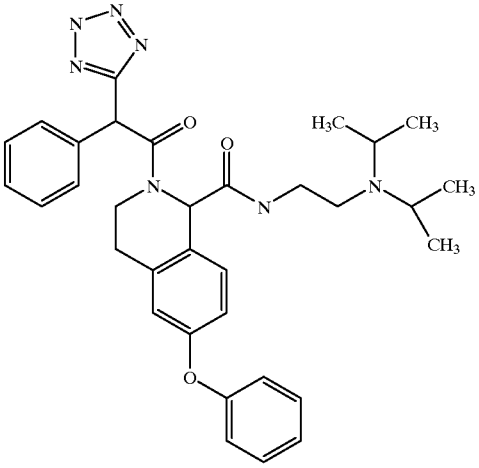 | 582 |
| 276 Diastereomer A | 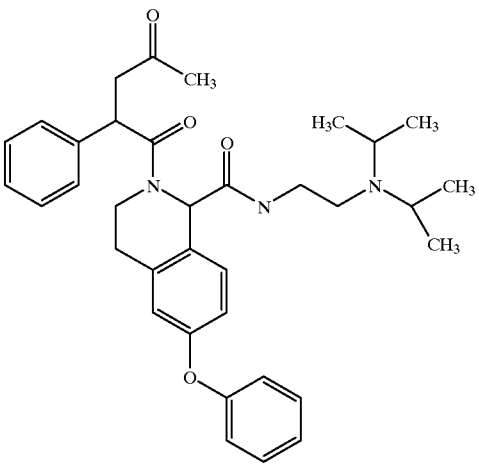 | 570 |
| 277 Diastereomer B | 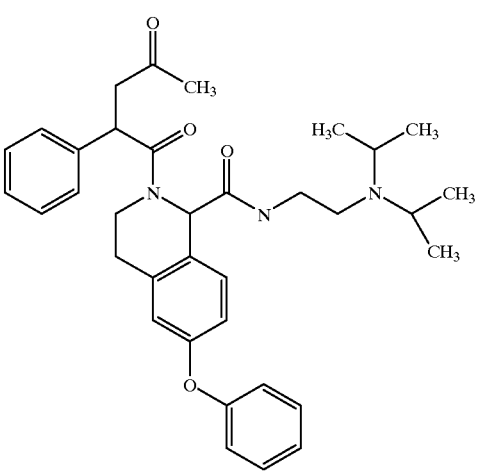 | 570 |

-continued

| Example No. | Structure | LC/MS (M + H) + |
|---|---|---|
| 278 Diastereomer A | 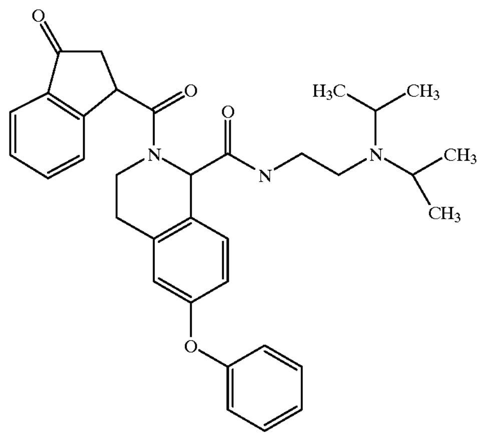 | 554 |
| 279 Diastereomer B | 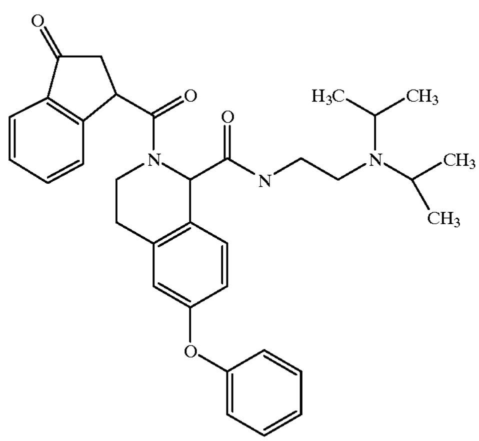 | 554 |
| 280 Isomer A | 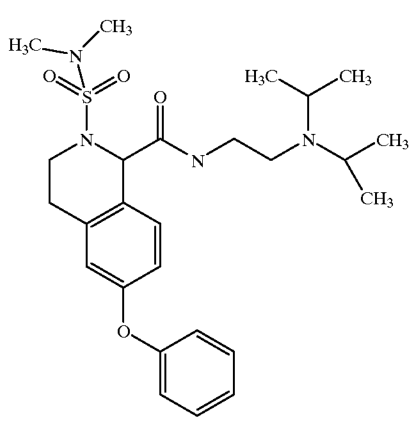 | 503 |

-continued

| Example No. | Structure | LC/MS (M + H) + |
|---|---|---|
| 281 Isomer B | 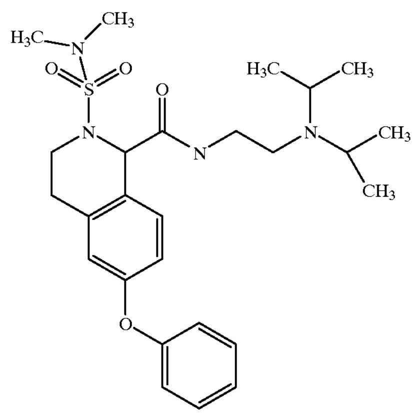 | 503 |
| 282 | 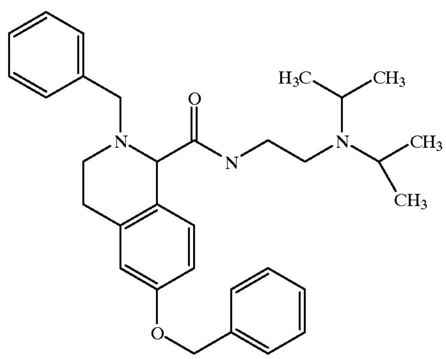 | 500 |
| 283 | 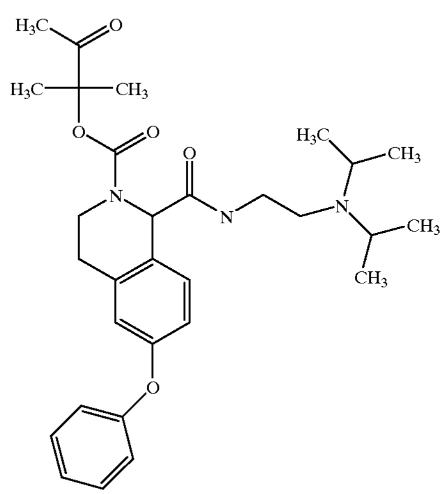 | 524 |

-continued
| Example No. | Structure | LC/MS (M + H) + |
|---|---|---|
| 284 | 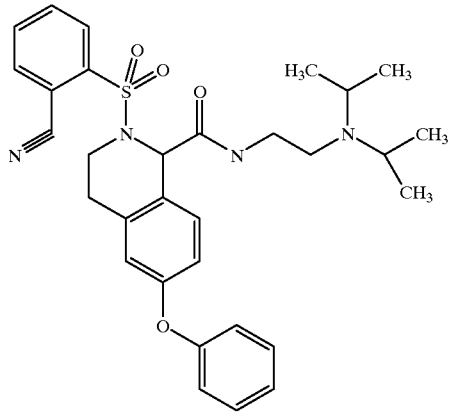 | 561 |
| 285 | 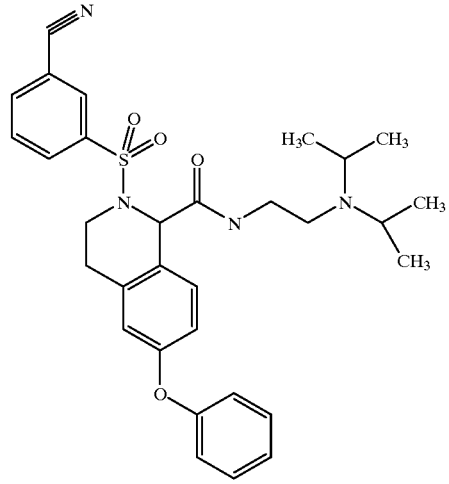 | 561 |
| 286 | 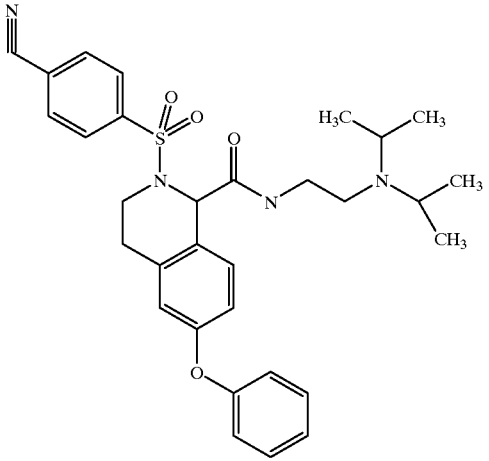 | 561 |

| Example No. | Structure | LC/MS (M + H) + |
|---|---|---|
| 287 | 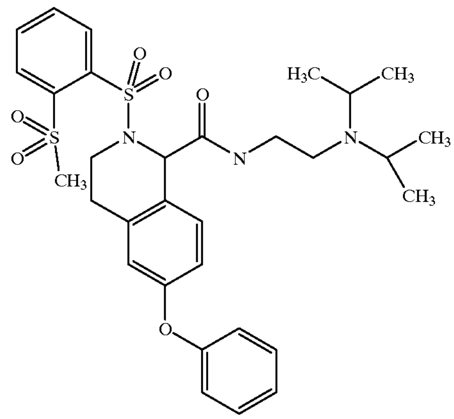 | 614 |
| 288 | 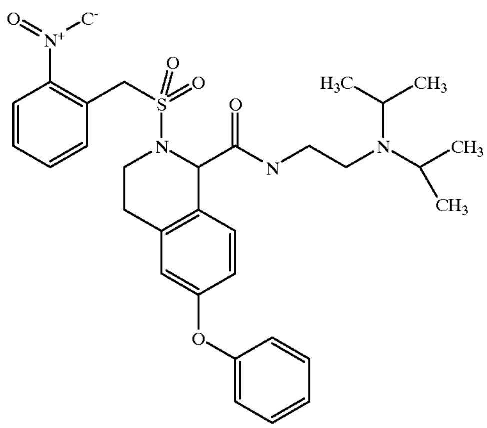 | 595 |
| 289 | 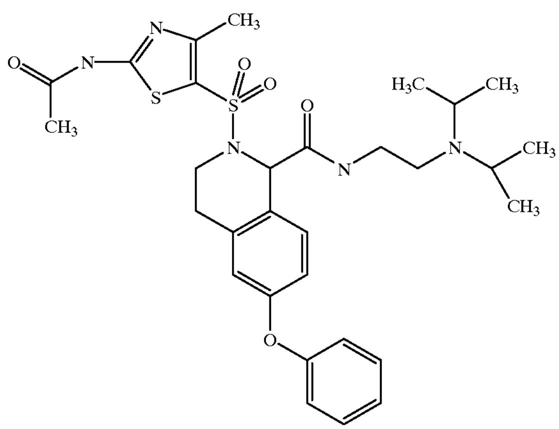 | 614 |

-continued
| Example No. | Structure | LC/MS (M + H) + |
|---|---|---|
| 290 | 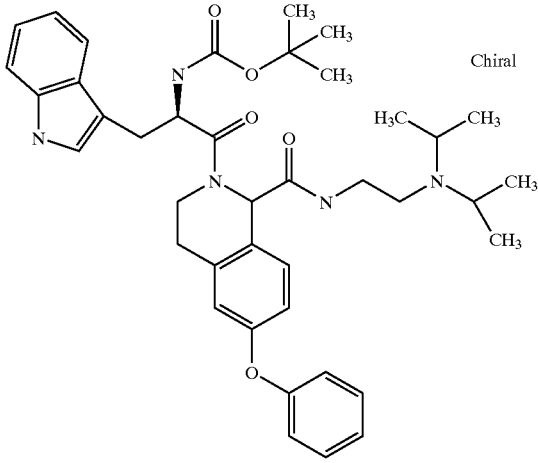 Chiral | 682 |
| 291 | 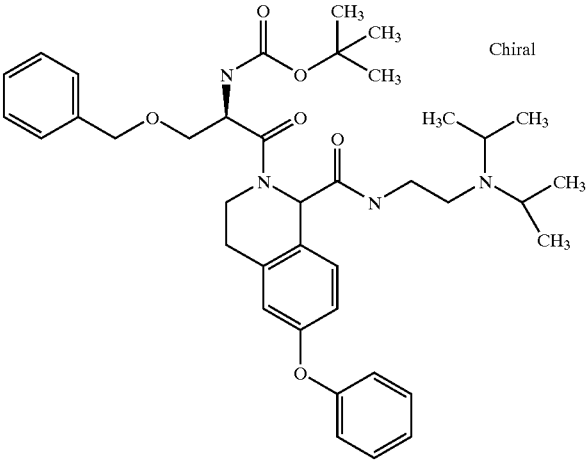 Chiral | 673 |
| 292 | 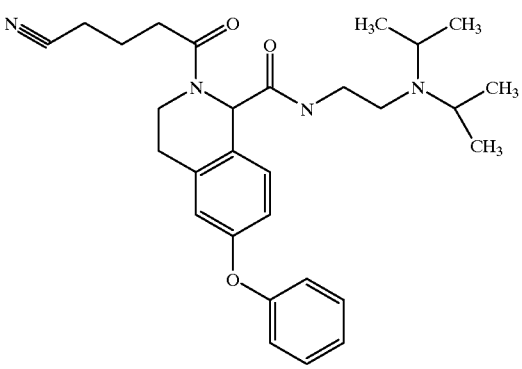 | 491 |

-continued
| Example No. | Structure | LC/MS (M + H) + |
|---|---|---|
| 293 | 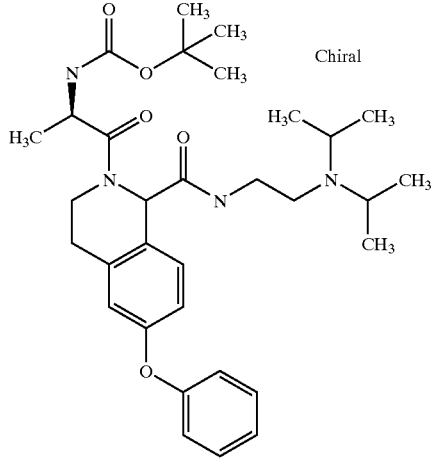 | 567 |
| 294 | 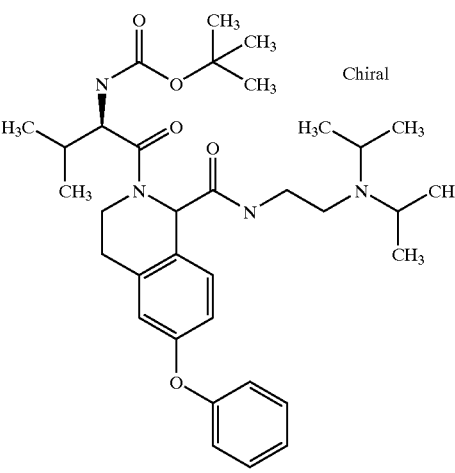 | 595 |
| 295 | 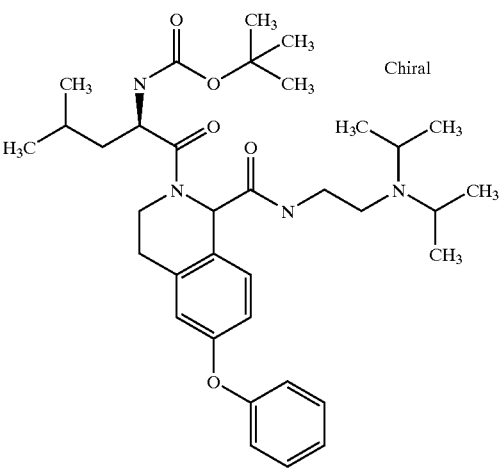 | 609 |

-continued
| Example No. | Structure | LC/MS (M + H)+ |
|---|---|---|
| 296 | 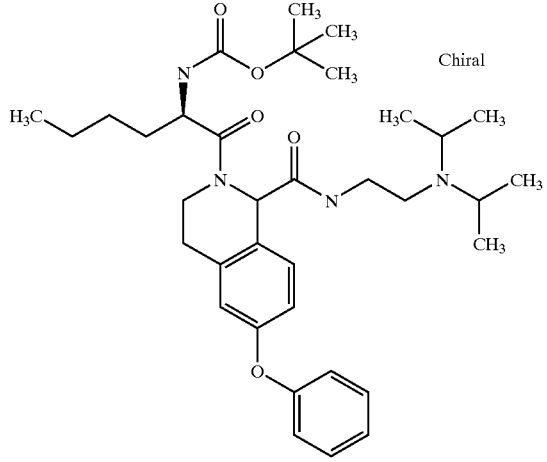 | 609 |
| 297 | 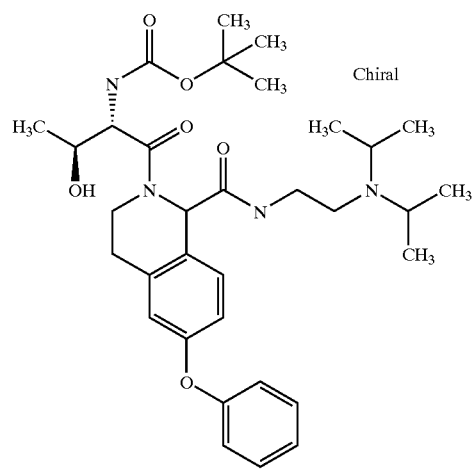 | 597 |
| 298 | 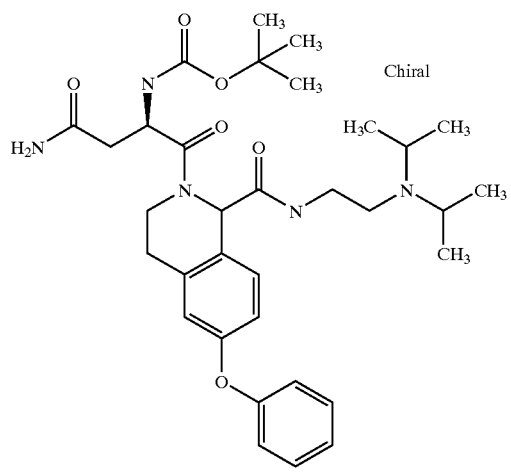 | 610 |

| Example No. | Structure | LC/MS (M + H)+ |
|---|---|---|
| 299 | 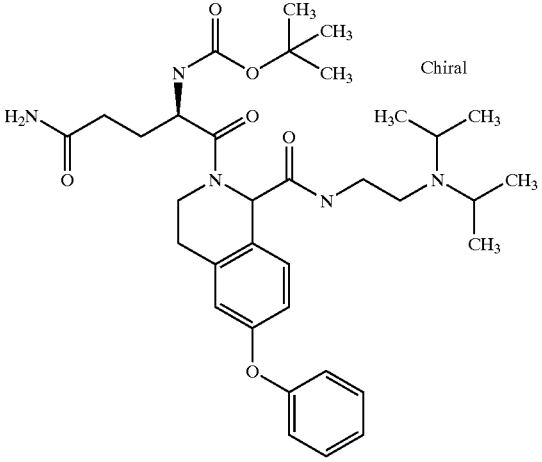 | 624 |
| 300 | 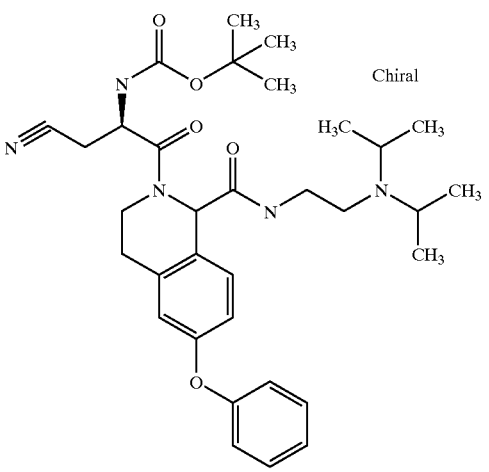 | 592 |
| 301 | 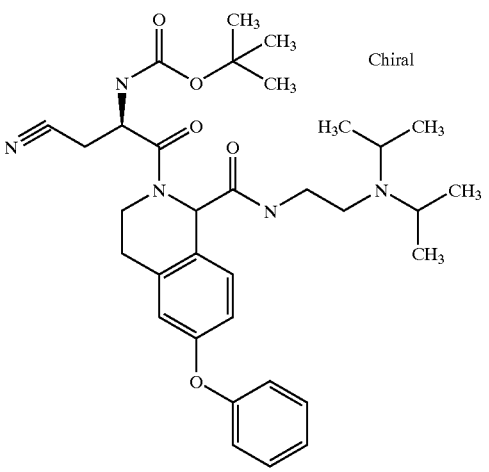 | 592 |

-continued

| Example No. | Structure | LC/MS (M + H) + |
|---|---|---|
| 302 | 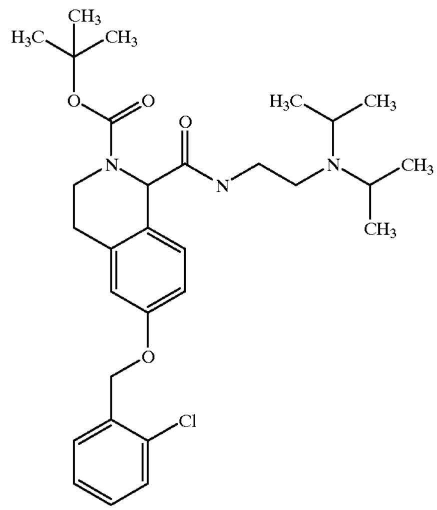 | 545 |
| 303 | 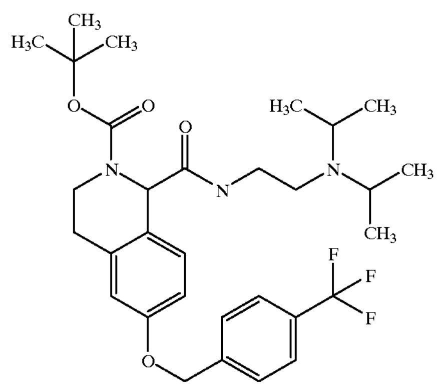 | 578 |
| 304 | 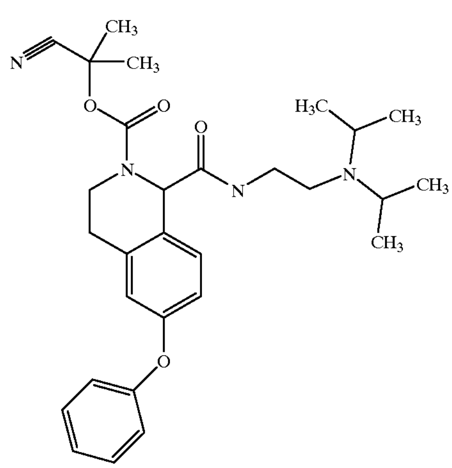 | 507 |

-continued
| Example No. | Structure | LC/MS (M + H) + |
|---|---|---|
| 305 | 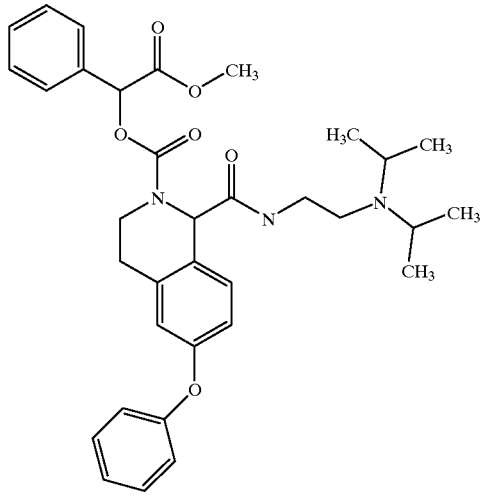 | 588 |
| 306 | 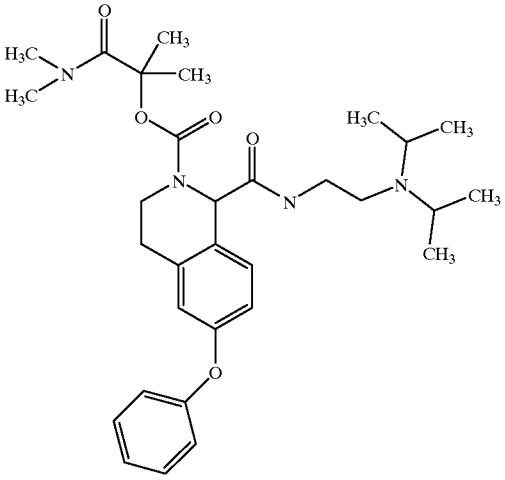 | 553 |
| 307 | 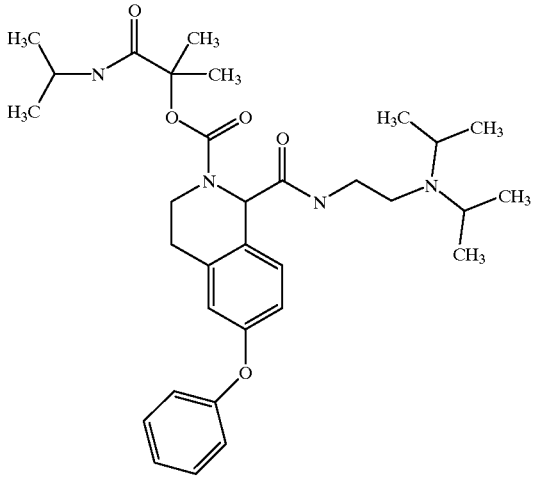 | 567 |

-continued
| Example No. | Structure | LC/MS (M + H) + |
|---|---|---|
| 308 | 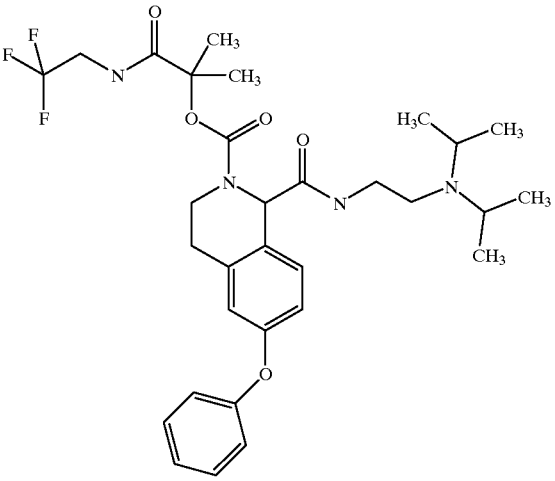 | 607 |
| 309 | 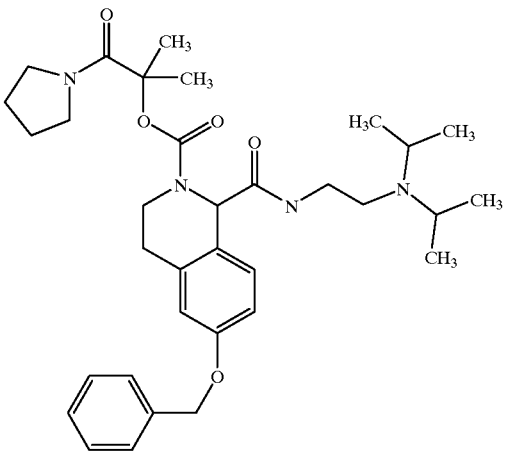 | 593 |
| 310 | 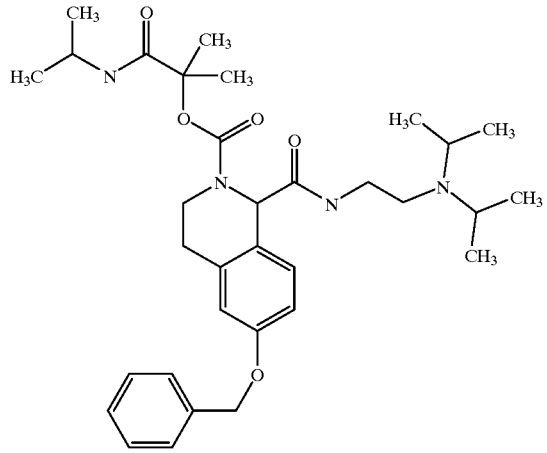 | 581 |

-continued
| Example No. | Structure | LC/MS (M + H) + |
|---|---|---|
| 311 | 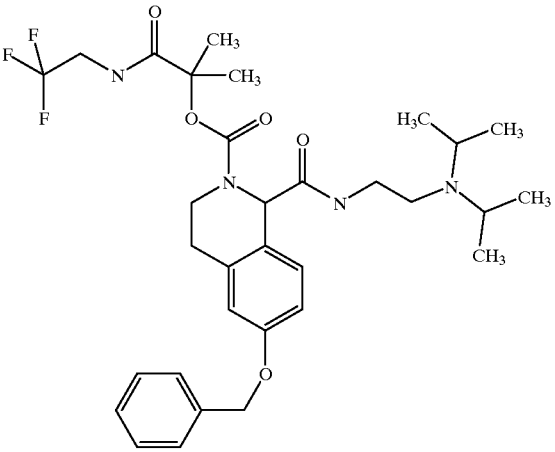 | 621 |
| 312 | 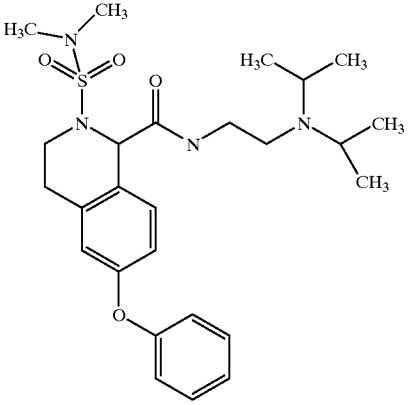 | 502 |
| 313 | 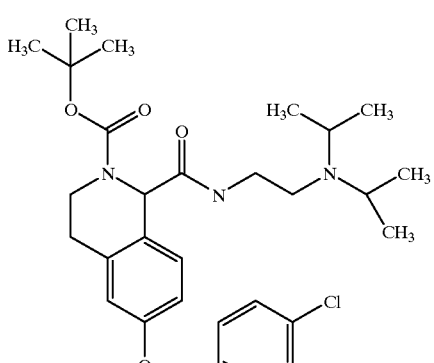 | 545 |

-continued
| Example No. | Structure | LC/MS (M + H) + |
|---|---|---|
| 314 | 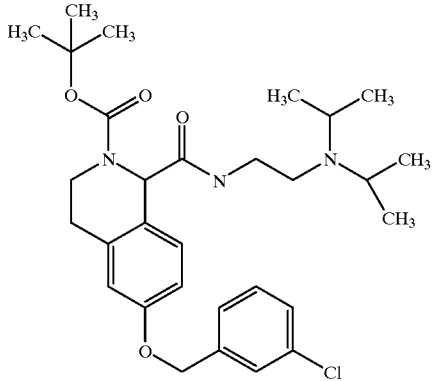 | 545 |
| 315 | 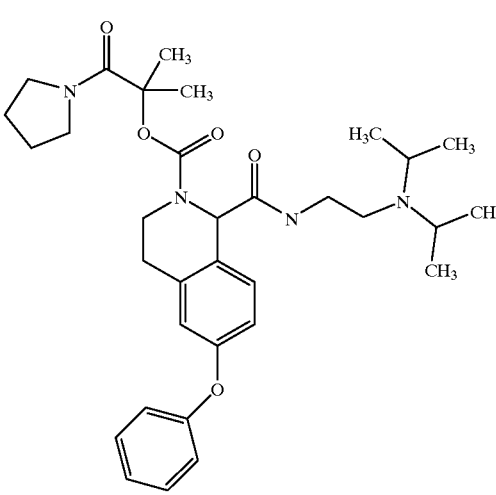 | 579 |
| 316 | 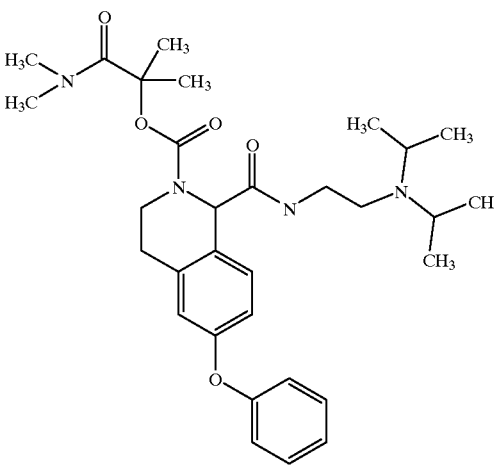 | 567 |

| Example No. | Structure | LC/MS (M + H) + |
|---|---|---|
| 317 | 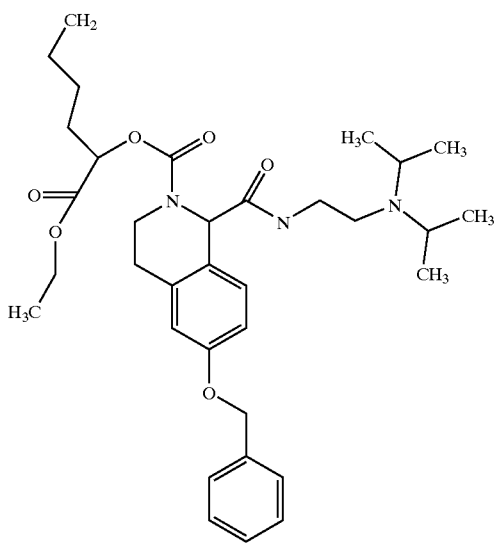 | 596 |
| 318 | 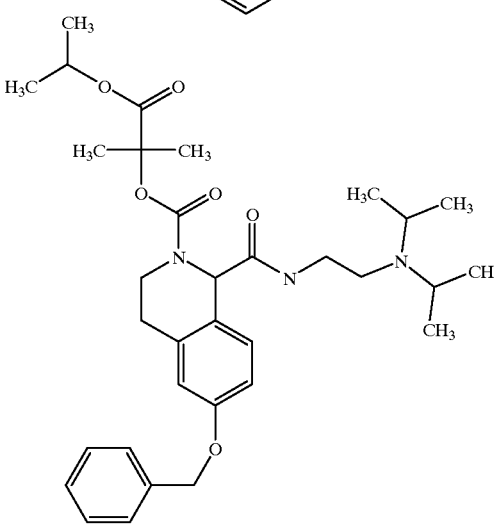 | 582 |
| 319 | 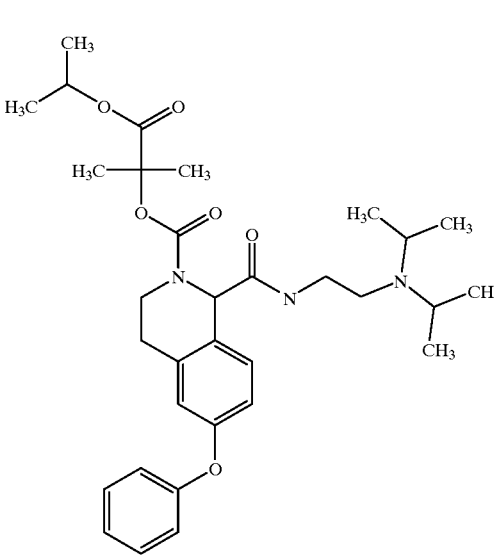 | 568 |

-continued

| Example No. | Structure | LC/MS (M + H) + |
|---|---|---|
| 320 | 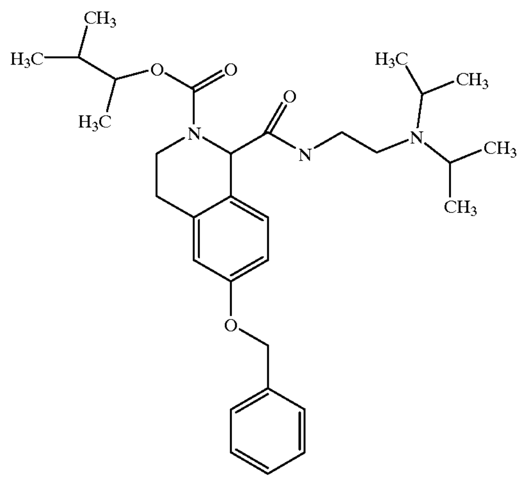 | 524 |
| 321 | 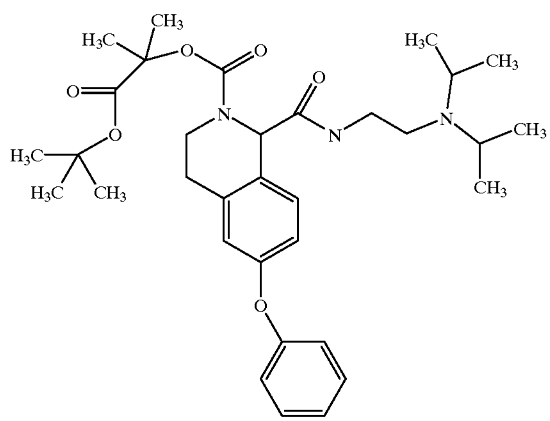 | 582 |
| 322 | 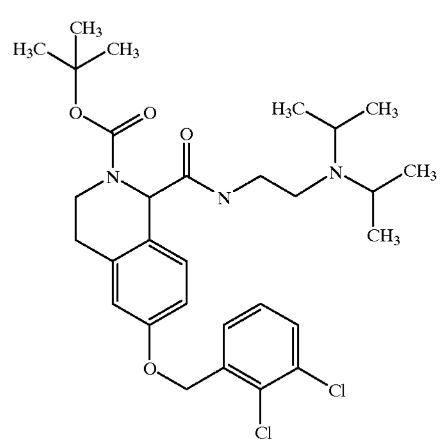 | 579 |

-continued

| Example No. | Structure | LC/MS (M + H) + |
|---|---|---|
| 323 | 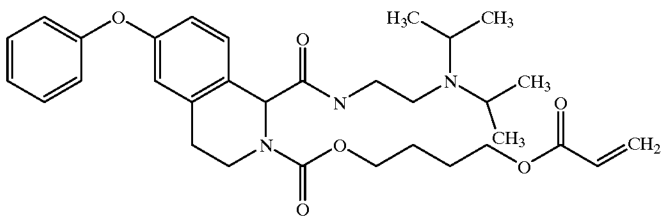 | 566 |
| 324 | 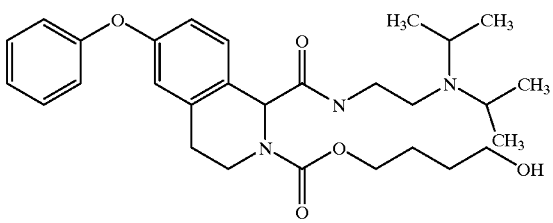 | 512 |
| 325 | 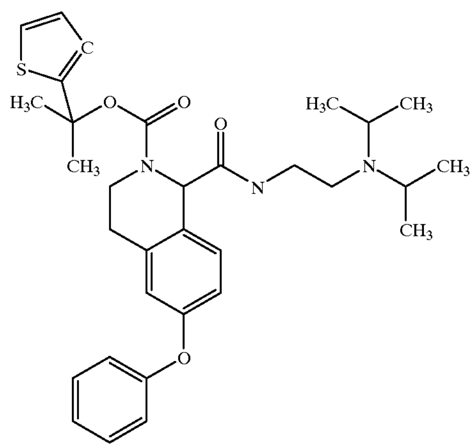 | 565 |
| 326 | 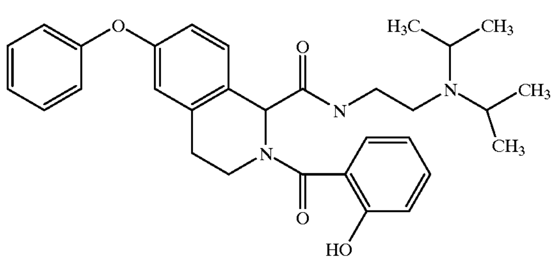 | 516 |
| 327 | 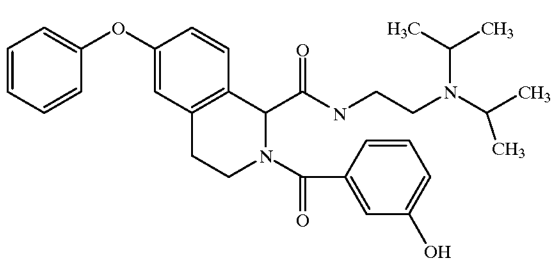 | 516 |

-continued

| Example No. | Structure | LC/MS (M + H) + |
|---|---|---|
| 328 | 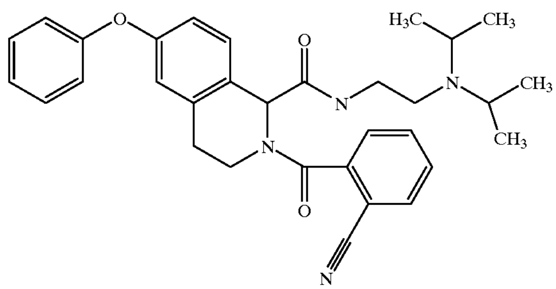 | 525 |
| 329 | 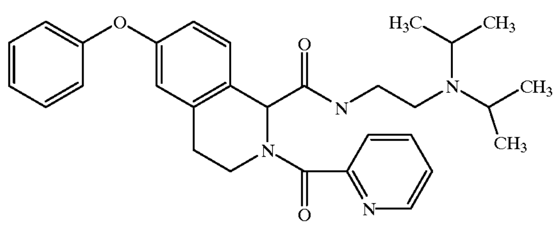 | 501 |
| 330 | 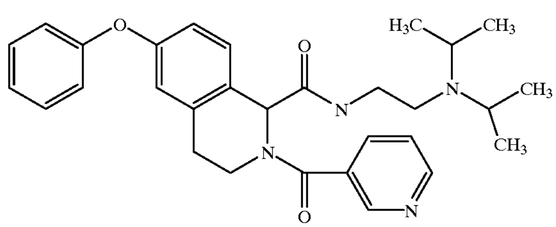 | 501 |
| 331 | 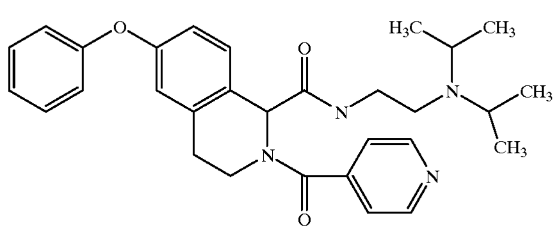 | 501 |
| 332 | 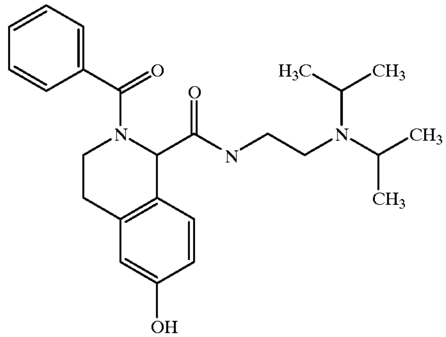 | 424 |

-continued

| Example No. | Structure | LC/MS (M + H) + |
|---|---|---|
| 333 | 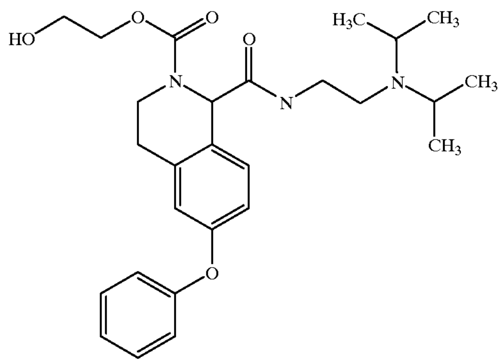 | 484 |
| 334 | 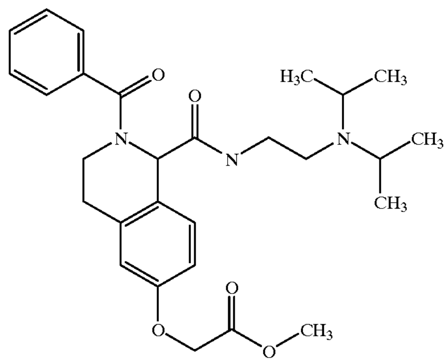 | 496 |
| 335 | 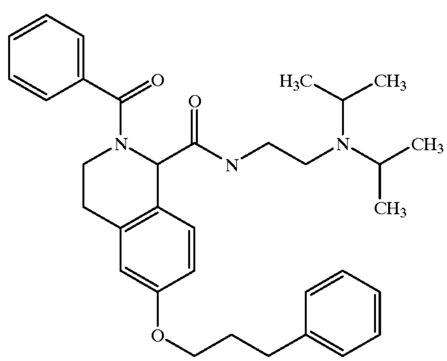 | 542 |
| 336 | 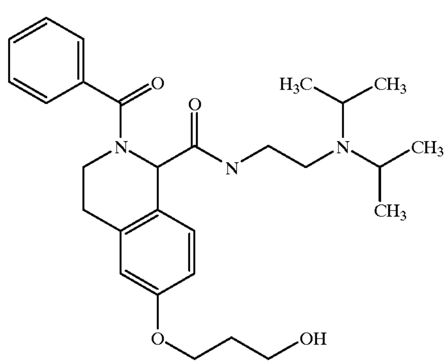 | 482 |

-continued
| Example No. | Structure | LC/MS (M + H) + |
|---|---|---|
| 337 | 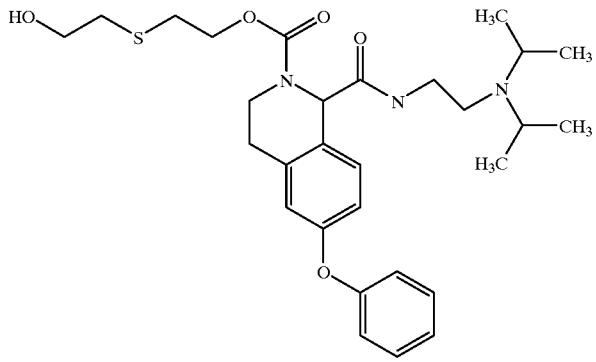 | 544 |
| 338 | 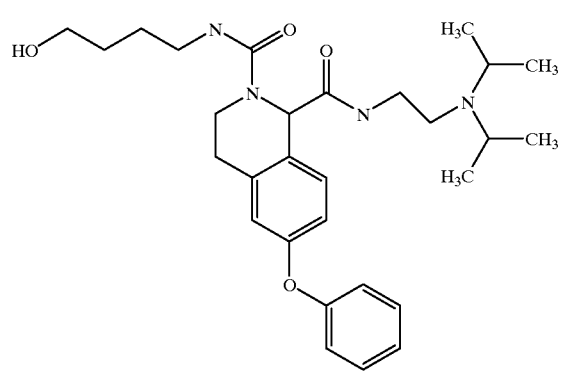 | 511 |
| 339 | 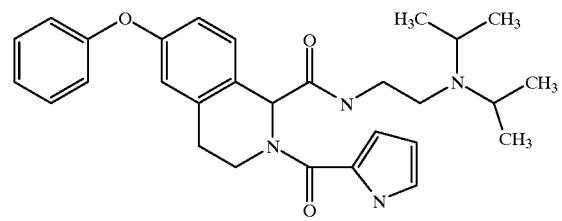 | 489 |
| 340 | 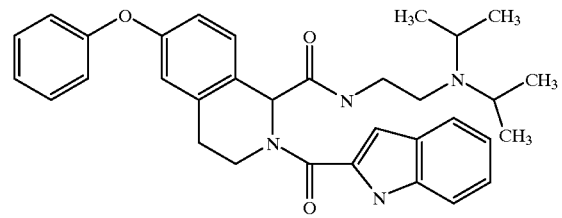 | 539 |
| 341 | 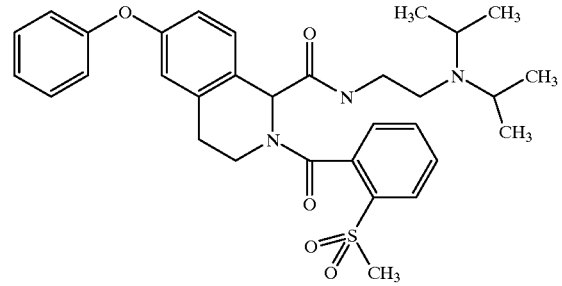 | 587 |

-continued

| Example No. | Structure | LC/MS (M + H) + |
|---|---|---|
| 342 | 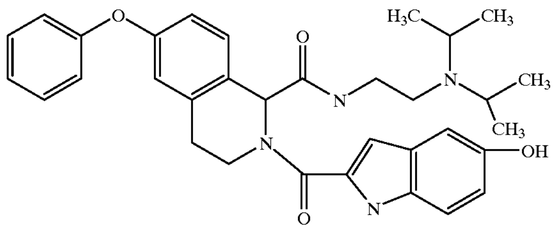 | 555 |
| 343 | 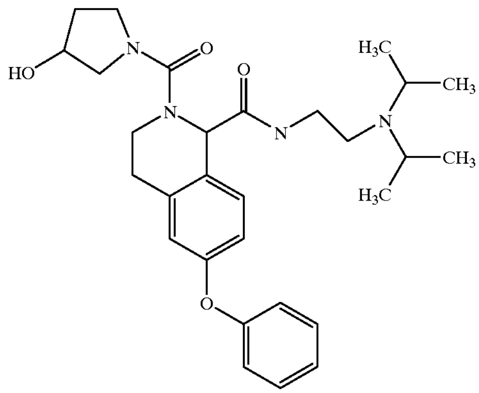 | 509 |
| 344 | 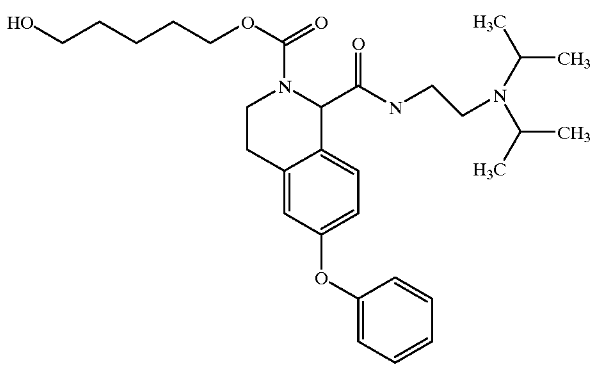 | 526 |
| 345 | 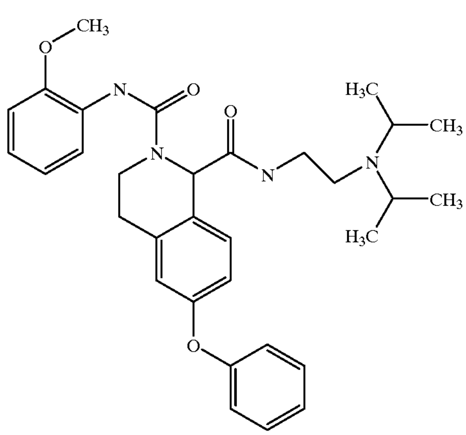 | 546 |

-continued

| Example No. | Structure | LC/MS (M + H) + |
|---|---|---|
| 346 | 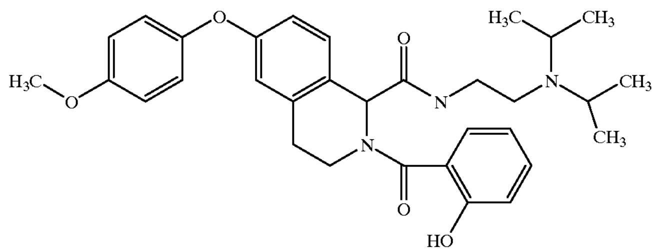 | 546 |
| 347 | 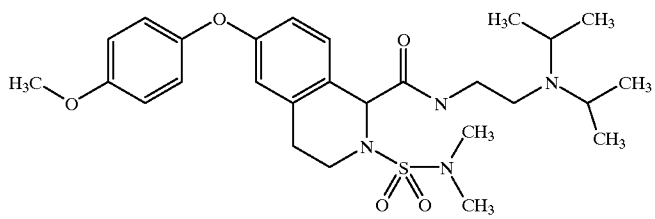 | 533 |
| 348 | 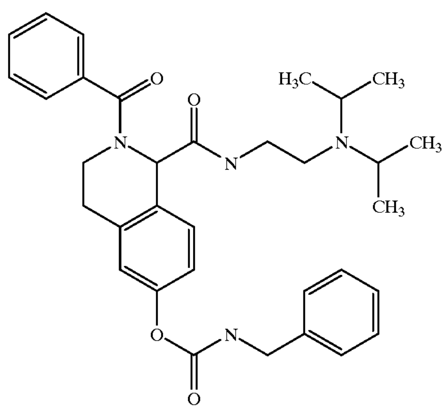 | 557 |
| 349 | 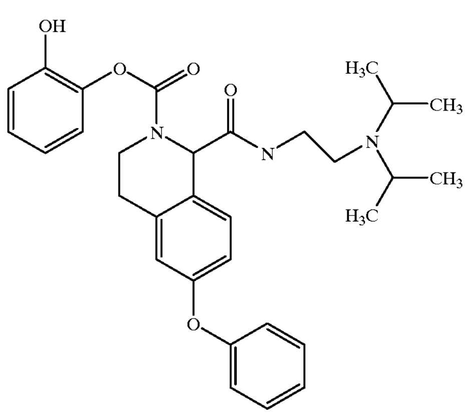 | 532 |

We claim:

1. A compound which has the structure

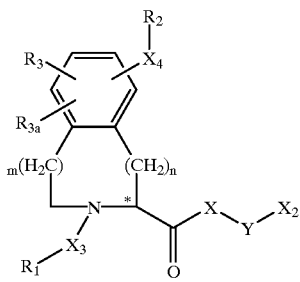

pharmaceutically acceptable salts, prodrug esters, and all stereoisomers thereof wherein $R_1$ is alkyl, aryl, alkenyl, alkynyl, arylalkyl, arylalkenyl, cycloalkyl, cycloalkylalkyl, cycloalkyl-alkoxy, alkoxyalkyl, alkylthioalkyl, aryloxyalkyl, arylalkoxyalkyl, cyclohetero-alkyl, cycloheteroalkylalkyl, heteroaryl, or heteroaryl-alkyl, and where these groups may be optionally substituted with 1 to 3 J1 groups which may be the same or different and the $R_1$ aryls may be further optionally substituted with 1 to 5 halogens, aryl, $-CF_3$, $-OCF_3$, 1–3 hydroxyls, 2 of which substituents where possible, may be joined by a methylene bridge;

$R_2$ is H, alkyl, aryl, alkenyl, alkynyl, arylalkyl, arylalkenyl, cycloalkyl, cycloalkylalkyl, alkoxyalkyl, aryloxyalkyl, arylalkoxyalkyl, cycloheteroalkyl, cycloheteroalkylalkyl, cycloalkylalkoxy, heteroaryl, or heteroarylalkyl, and where these groups may be optionally substituted with a J1a group and the aryls may be further optionally substituted with 1 to 5 halogens, $-CF_3$, $-OCF_3$, or 1–3 hydroxyls;

X is a bond, $-O-$, or $-NR_4-$;

$R_3$ and $R_{3a}$ are the same or different and are independently selected from H, alkoxy, halogen, $-CF_3$, alkyl, or aryl;

$R_4$, $R_{4a}$, $R_{4b}$, $R_{4c}$, $R_{4d}$, $R_{4e}$, $R_{4f}$, $R_{4g}$, $R_{4h}$, $R_{4i}$, $R_{4j}$, $R_{4k}$, and $R_{4l}$ are the same or different and are independently selected from H, $C_1$–$C_6$alkyl, or aryl;

m and n are the same or different and are independently 0 or 1;

Y is

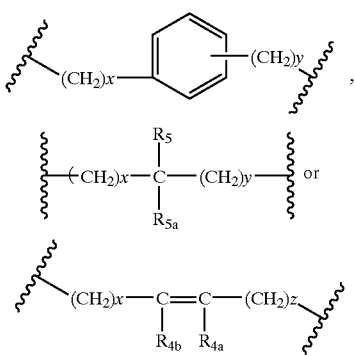

where x and y are the same or different and are independently 0 to 3 and z is 1 to 3;

$R_5$ and $R_{5a}$ are the same or different and are independently H, alkyl, alkoxy, hydroxyl, halogen, $-CF_3$, aryl, alkaryl, and cycloalkyl; or $R_5$ and $R_{5a}$ can be independently joined to one or both of $R_6$ and $R_7$ groups to form an alkylene bridge of 1 to 5 carbon atoms; or $R_5$ and $R_{5a}$ can be joined together to form a ring of from 4–7 carbon atoms;

$X_2$ is

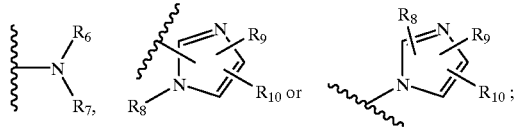

$R_6$ and $R_7$ are the same or different and are independently selected from H and alkyl, where the alkyl may be optionally substituted with halogen, 1 to 3 hydroxyls, 1 to 3 $C_1$–$C_{10}$alkanoyloxy, 1 to 3 $C_1$–$C_6$ alkoxy, phenyl, phenoxy, $C_1$–$C_6$alkoxycarbonyl; or $R_6$ and $R_7$ can together form $-(CH_2)_tX_5(CH_2)_u-$ where $X_5$ is $-C(R_{4c})(R_{4d})-$, $-O-$ or $-N(R_{4e})-$, t and u are the same or different and are independently 1–3;

$R_8$ is H, $C_1$–$C_6$alkyl, $-CF_3$, alkaryl, or aryl, and with the alkyl and aryl groups being optionally substituted with 1 to 3 hydroxyls, 1 to 3 $C_1$–$C_{10}$alkanoyloxy, 1 to 3 $C_1$–$C_6$ alkoxy, phenyl, phenoxy or $C_1$–$C_6$ alkoxycarbonyl;

$R_9$ and $R_{10}$ are the same or different and are independently selected from H, $C_1$–$C_6$alkyl, $-CF_3$, alkaryl, aryl, or halogen, and with the alkyl and aryl groups being optionally substituted with 1 to 3 hydroxyls, 1 to 3 $C_1$–$C_{10}$ alkanoyloxy, 1 to 3 $C_1$–$C_6$ alkoxy, phenyl, phenoxy or $C_1$–$C_6$alkoxycarbonyl;

$X_3$ is a bond, $-C(O)-$, $-C(O)O-$, $-C(O)N(R_{4f})-$, $-S(O)_2-$, or $-S(O)_2N(R_{4f})-$;

$X_4$ is a bond, $-O-$, $-OC(O)-$, $-N(R_{4g})-$, $-N(R_{4g})C(O)-$, $-N(R_{4g})C(O)N(R_{4h})-$, $-N(R_{4g})S(O)_2-$, $-N(R_{4g})S(O)_2N(R_{4h})$, $-OC(O)N(R_{4g})-$, $-C(O)-$, $-C(O)N(R_{4g})-$, $-S-$, $-S(O)_2-$, or $-S(O)_2N(R_{4g})-$;

J1 and J1a are the same or different and are independently nitro, halogen, hydroxyl, $-OCF_3$, $-CF_3$, alkyl, $-(CH_2)_vCN$, $-(CH_2)_vN(T_{1a})C(O)T_1$, $-(CH_2)_vN(T_{1a})C(O)$ $OT_1$, $-(CH_2)_vN(T_{1a})C(O)N(T_{1b})T_1$, $-(CH_2)_vNT_1(T_{1a})$, $-(CH_2)_vN(T_{1a})$ $SO_2T_1$, $-(CH_2)_vC(O)N(T_{1a})T_1$, $-(CH_2)_vC(O)OT_1$, $-(CH_2)_vOC(O)OT_1$, $-(CH_2)_vOC(O)T_1$, $-(CH_2)_vOC(O)OT_1$, $-(CH_2)_vOC(O)T_1$, $-(CH_2)_vOC(O)N(T_{1a})T_1$, $-(CH_2)_vN(T_{1a})SO_2N(T_{1a})T_1$, $-(CH_2)_vOT_1$, $-(CH_2)_vSO_2T_1$, $-(CH_2)_vSO_2N(T_{1b})T_1$, $-(CH_2)_vC(O)T_1$, $-(CH_2)_vCH(OH)T_1$, or heteroaryl as defined below, with v being 0–3;

$T_1$, $T_{1a}$ and $T_{1b}$ are the same or different and are independently H, alkyl, alkenyl, alkynyl, lower alkylthioalkyl, alkoxyalkyl, aryl, arylalkyl, heteroaryl, heteroarylalkyl, cycloheteroalkyl, or cycloalkyl, each of which may be optionally substituted with halogen, hydroxyl, $-C(O)NR_{4i}R_{4j}$, $-NR_{4i}C(O)R_{4j}$, $-CN$, $-N(R_{4i})SO_2R_{11}$, $-OC(O)R_{4i}$, $-SO_2NR_{4i}R_{4j}$, $-SOR_{11}$, $-SO_2R_{11}$, alkoxy, $-COOH$, cycloheteroalkyl, or $-C(O)OR_{11}$; with the proviso that $T_1$ cannot be hydrogen when it is connected to sulfur as in $SO_2T_1$;

or $T_1$ and $T_{1a}$ or $T_1$ and $T_{1b}$ can together form $-(CH_2)_rX_{5a}(CH_2)_s-$ where $X_{5a}$ is $-C(R_{4k})(R_{4l})-$, —O— or —N($R_{4k}$k), where r and s are the same or different and are independently 1–3;

$R_{11}$ is $C_1$–$C_6$alkyl or aryl;

provided (1) where m is 0 and n is 1, the moiety —$X_4$—$R_2$ is other than alkyl or alkoxy; and (2) where X is a bond and $X_2$ is amino, then m is 1.

2. The compound as defined in claim 1 having the structure

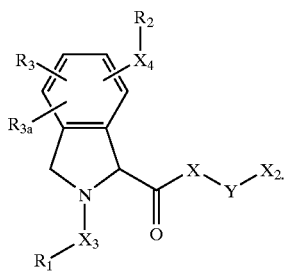

3. The compound as defined in claim 1 having the structure

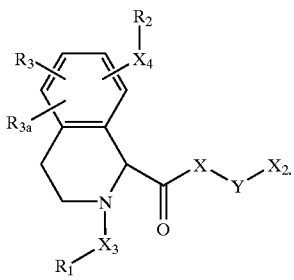

4. The compound as defined in claim 1 having the following structure:

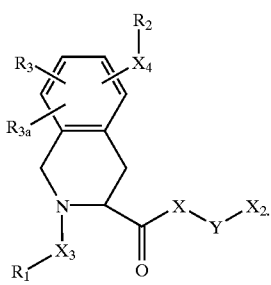

5. The compound as defined in claim 1 having the following structure:

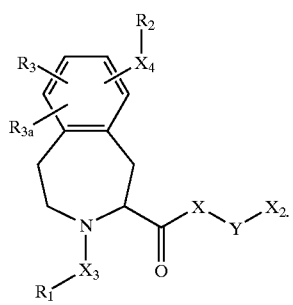

6. The compound as defined in claim 1 wherein $R_1$ is alkyl, aryl, arylalkyl, cycloalkyl, cycloalkylalkyl, alkoxyalkyl, aryloxyalkyl, heteroaryl, or heteroarylalkyl, any of which may be optionally substituted with a J1 group;

$R_2$ is alkyl, aryl, arylalkyl, alkoxyalkyl, aryloxyalkyl, heteroaryl, cycloalkyl, cycloalkylalkyl, or heteroarylalkyl, and these groups may be optionally substituted by J1a;

$R_3$ and $R_{3a}$ are the same or different and are independently selected from H, alkoxy, halogen, or —$CF_3$;

m and n are independently 0 or 1;

X is O or —$NR_4$—;

Y is

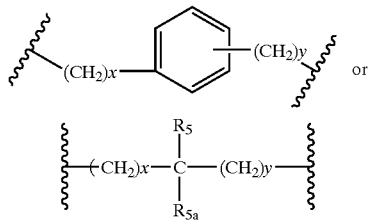

where x and y are independently 0 to 3;

$R_4$ is H or $C_1$–$C_6$ alkyl;

$R_5$ and $R_{5a}$ are the same or different and are independently selected from H, alkyl, or —$CF_3$, or $R_5$ and $R_{5a}$ can be independently joined to one or both of $R_6$ and $R_7$ groups to form an alkylene bridge of 1 to 5 carbon atoms;

$X_2$ is

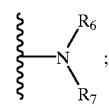

$R_6$ and $R_7$ are the same or different and are independently selected from H, or alkyl, where alkyl may be substituted with halogen, 1 to 2 hydroxyls, 1 to 2 $C_1$–$C_{10}$ alkanoyloxy, 1 to 2 $C_1$–$C_6$ alkoxy, phenyl, phenoxy, $C_1$–$C_6$ alkoxycarbonyl; or $R_6$ and $R_7$ can together form —($CH_2$)$_t$$X_5$($CH_2$)$_u$— where $X_5$ is —C($R_{4c}$)($R_{4d}$)— or —O—, t and u are the same or different and are independently 1–3;

$X_3$ is —C(O)—, —C(O)O—, or —S(O)$_2$N ($R_{4f}$);

$X_4$ is a bond, —O—, —OC(O)—, or —N($R_{4g}$)C(O)—;

J1 is —($CH_2$)$_v$CN, —($CH_2$)$_v$N($T_{1a}$)C(O)$T_1$, —($CH_2$)$_v$N($T_{1a}$)C(O)O$T_1$, —($CH_2$)$_v$N($T_{1a}$)C(O)N($T_{1b}$)$T_1$, —($CH_2$)$_v$SO$_2$$T_1$, —($CH_2$)$_v$N($T_{1a}$)SO$_2$$T_1$, —($CH_2$)$_v$C(O)N($T_{1a}$)$T_1$, —($CH_2$)$_v$C(O)O$T_1$, —($CH_2$)$_v$OC(O)$T_1$, —($CH_2$)$_v$OC(O)N($T_{1a}$)$T_1$, —($CH_2$)$_v$N($T_{1a}$)SO$_2$N($T_{1b}$)$T_1$, —($CH_2$)$_v$O$T_1$, —($CH_2$)$_v$SO$_2$N($T_{1b}$)$T_1$, —($CH_2$)$_v$C(O)$T_1$, or heteroaryl, with v being 0–2;

J1a is halogen, —($CH_2$)$_v$CN, —($CH_2$)$_v$N($T_{1a}$)C(O)$T_1$, —($CH_2$)$_v$C(O)N($T_{1a}$)$T_1$, —($CH_2$)$_v$C(O)O$T_1$, —($CH_2$)$_v$O$T_1$, or —($CH_2$)$_v$C(O)$T_1$, with v being 0–2; and $T_1$, $T_{1a}$ and $T_{1b}$ are the same or different and are independently selected from H, alkyl, aryl, alkaryl, or cycloalkyl each optionally substituted with halogen, hydroxyl or alkoxy; with the proviso that $T_1$ cannot be hydrogen when it is connected sulfur as in $SO_2T_1$.

7. The compound as defined in claim 1 wherein
$R_1$ is alkyl, aryl, arylakyl, cycloalkyl, or cycloalkylalkyl and where these groups may be optionally substituted with a J1 group;
$R_2$ is alkyl, aryl, arylalkyl, or cycloalkyl, and these groups may be optionally substituted by J1a;
X is —NH or —NCH$_3$;
$R_3$ and $R_{3a}$ are each H;
m is 1;
n is 0;
Y is $$\text{{CH}_2\text{)}x\text{—}\underset{R_{5a}}{\overset{R_5}{C}}\text{—(CH}_2\text{)}y}$$

where x and y are independently 0 or 1, with the proviso that both cannot be 0;
$R_5$ and $R_{5a}$ are the same or different and are independently selected from H, alkyl, or —CF$_3$; or $R_5$ and $R_{5a}$ can be independently joined to one or both of $R_6$ and $R_7$ groups to form an alkylene bridge of 1 to 5 carbon atoms;
$X_2$ is $$\underset{R_7}{\overset{R_6}{N}}$$

$R_6$ and $R_7$ are the same or different and are independently selected from H or alkyl, where alkyl may be optionally substituted with halogen, or 1 to 2 hydroxyls;
$X_3$ is —C(O)—, —C(O)O—, or —S(O)$_2$N(R$_{4f}$)—;
$X_4$ is —O—, or —OC(O)—;
J1 is —(CH$_2$)$_v$CN, —(CH$_2$)$_v$N(T$_{1a}$)C(O)T$_1$, —(CH$_2$)$_v$N(T$_{1a}$)C(O)OT$_1$, —(CH$_2$)$_v$N(T$_{1a}$)C(O)N(T$_{1b}$)T$_1$, —(CH$_2$)$_v$SO$_2$T$_1$, —(CH$_2$)$_v$N(T$_{1a}$)SO$_2$T$_1$, —(CH$_2$)$_v$C(O)N(T$_{1a}$)T$_1$, —(CH$_2$)$_v$C(O)OT$_1$, —(CH$_2$)$_v$OC(O)T$_1$, —(CH$_2$)$_v$OC(O)N(T$_{1a}$)T$_1$, —(CH$_2$)$_v$N(T$_{1a}$)SO$_2$N(T$_{1b}$)T$_1$, —(CH$_2$)$_v$OT$_1$, —(CH$_2$)$_v$SO$_2$N(T$_{1a}$)T$_1$, —(CH$_2$)$_v$C(O)T$_1$, or heteroaryl as defined below, with v being 0–2;
J1a is halogen, —CF$_3$, —(CH$_2$)$_v$CN, —(CH$_2$)$_v$N(T$_{1a}$)C(O)T$_1$, —(CH$_2$)$_v$C(O)N(T$_{1a}$)T$_1$, —(CH$_2$)$_v$C(O)OT$_1$, —(CH$_2$)$_v$OT$_1$, or —(CH$_2$)$_v$C(O)T$_1$, with v being 0–2; and
$T_1$, $T_{1a}$ and $T_{1b}$ are the same or different and are independently selected from H, alkyl, aryl, or alkaryl, optionally substituted with halogen, hydroxyl or alkoxy; with the proviso that $T_1$ cannot be hydrogen when it is connected to sulfur as in $SO_2T_1$.

8. The compound as defined in claim 1 wherein
$R_1$ is alkyl, aryl, arylakyl, cycloalkyl, heteroaryl or heteroarylalkyl and where these groups may be optionally substituted with a J1 group;
$R_2$ is aryl, arylalkyl, or cycloalkyl, where these groups may be optionally substituted with one or more J1a;

X is —N(R$_4$)— where R$_4$ is H or alkyl;
$R_3$ and $R_{3a}$ are each H;
m is 1;
n is 0;
Y is $$\text{{CH}_2\text{)}x\text{—}\underset{R_{5a}}{\overset{R_5}{C}}\text{—(CH}_2\text{)}y}$$

where x and y are independently 0 or 1;
$R_5$ and $R_{5a}$ are the same or different and are independently selected from H, alkyl, or —CF$_3$;
$X_2$ is $$\underset{R_7}{\overset{R_6}{N}}$$

$R_6$ and $R_7$ are the same or different and are independently selected from H or alkyl, where alkyl may be optionally substituted with halogen, or 1 to 2 hydroxyls;
$X_3$ is —C(O)—, —C(O)O—, —S(O)$_2$— or —S(O)$_2$N(R$_{4f}$)—;
$X_4$ is —O—, or —OC(O)—;
J1 is alkyl, —(CH$_2$)$_v$CN, —(CH$_2$)$_v$N(T$_{1a}$)C(O)T$_1$, —(CH$_2$)$_v$N(T$_{1a}$)C(O)OT$_1$, —(CH$_2$)$_v$N(T$_{1a}$)C(O)N(T$_{1b}$)T$_1$, —(CH$_2$)$_v$SO$_2$T$_1$, —(CH$_2$)$_v$N(T$_{1a}$)SO$_2$T$_1$, —(CH$_2$)$_v$C(O)N(T$_{1a}$)T$_1$, —(CH$_2$)$_v$C(O)OT$_1$, —(CH$_2$)$_v$OC(O)T$_1$, —(CH$_2$)$_v$OC(O)N(T$_{1a}$)T$_1$, —(CH$_2$)$_v$N(T$_{1a}$)SO$_2$N(T$_{1b}$)T$_1$, —(CH$_2$)$_v$OT$_1$, —(CH$_2$)$_v$SO$_2$N(T$_{1a}$)T$_1$, —(CH$_2$)$_v$C(O)T$_1$, or heteroaryl as defined below, with v being 0–2;
J1a is halogen, —CF$_3$, —(CH$_2$)$_v$CN, (CH$_2$)$_v$N(T$_{1a}$)C(O)T$_1$, —(CH$_2$)$_v$C(O)N(T$_{1a}$)T$_1$, —(CH$_2$)$_v$C(O)OT$_1$, —(CH$_2$)$_v$OT$_1$, or —(CH$_2$)$_v$C(O)T$_1$, with v being 0–2; and
$T_1$, $T_{1a}$ and $T_{1b}$ are the same or different and are independently selected from H, alkyl, aryl, or alkaryl, optionally substituted with halogen, hydroxyl or alkoxy; with the proviso that $T_1$ cannot be hydrogen when it is connected to sulfur as in $SO_2T_1$.

9. A compound as defined in claim 1 having the structure

-continued
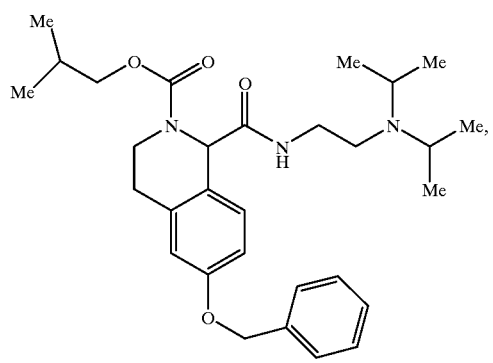
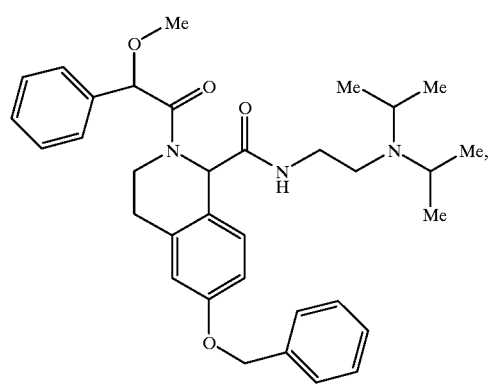
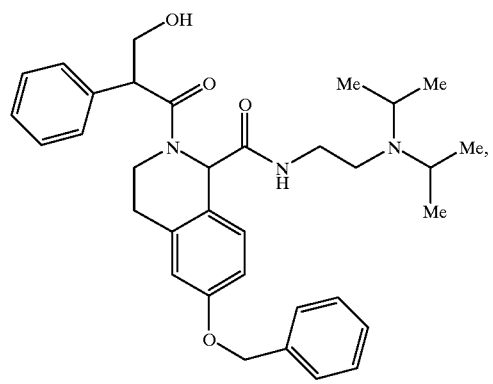
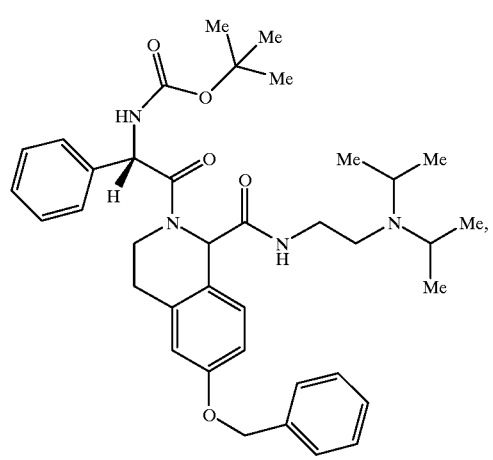
-continued
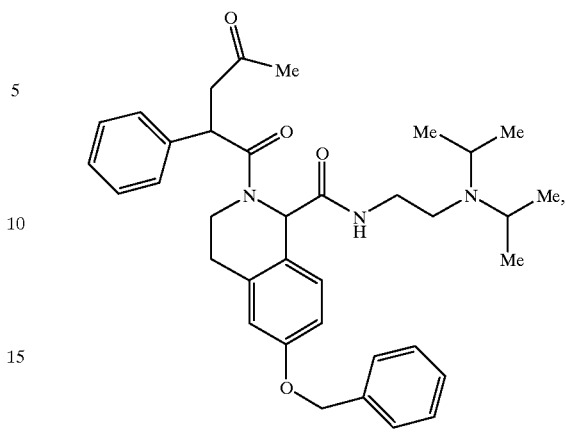
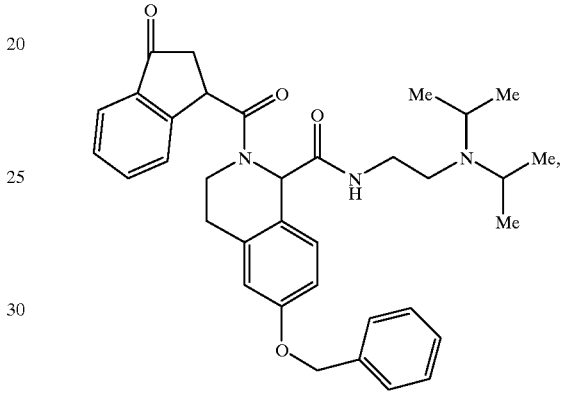
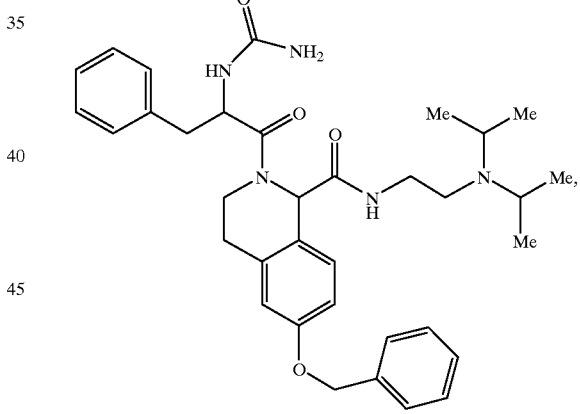
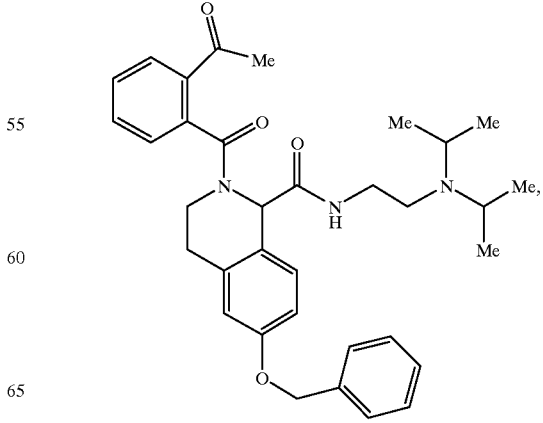

187
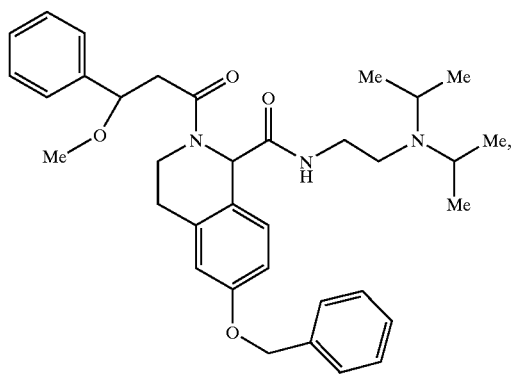
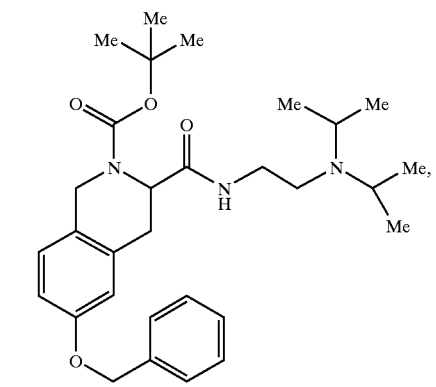
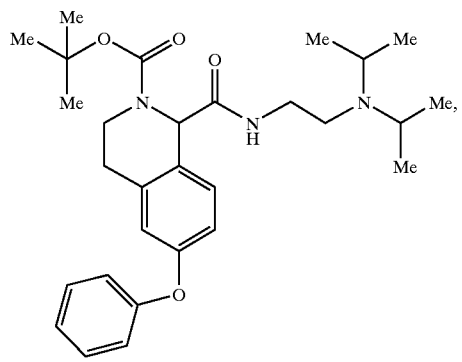
racemic
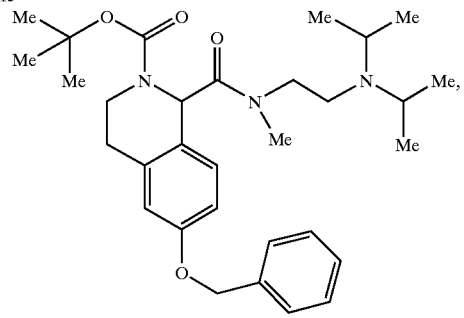
188
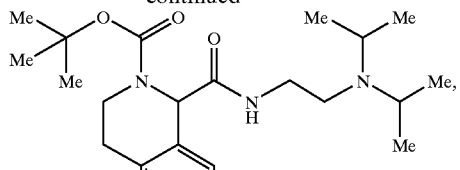
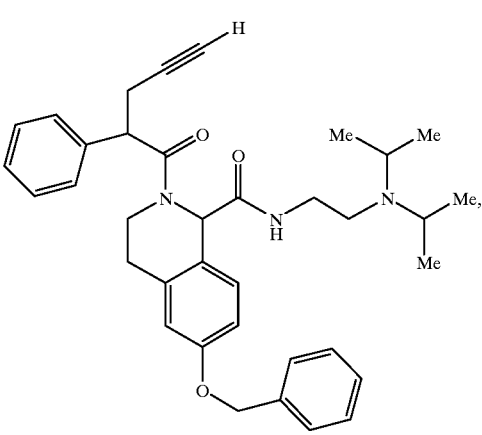
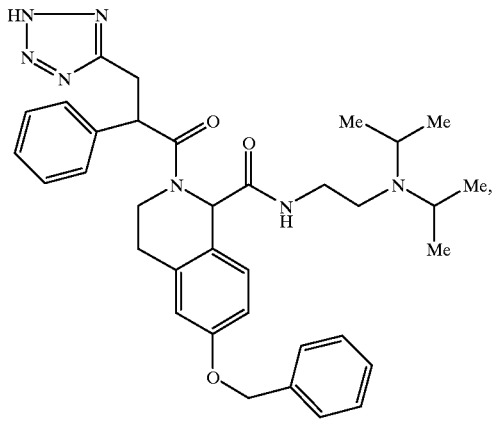
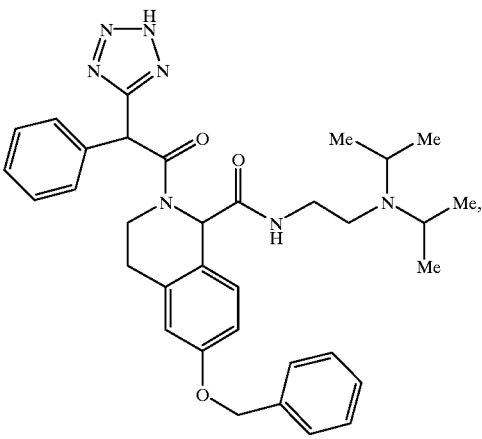

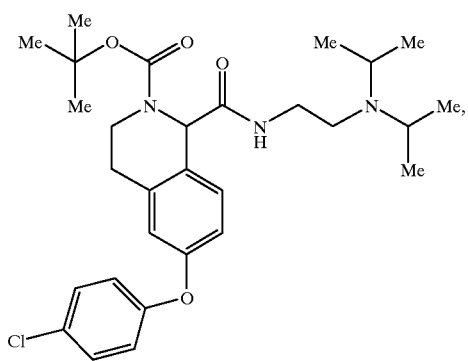
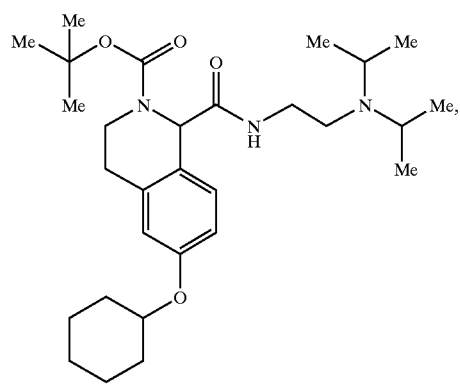
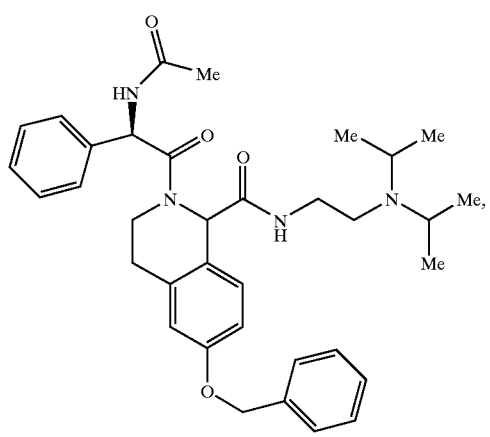
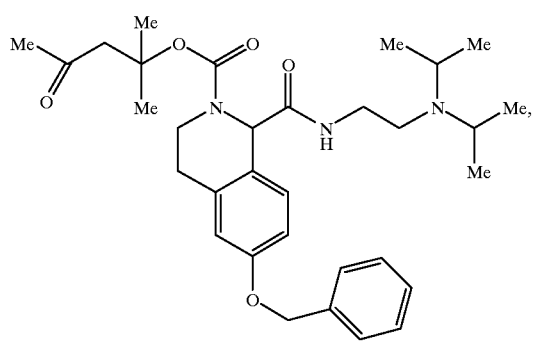
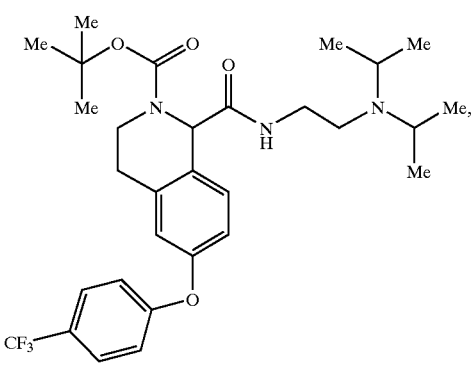
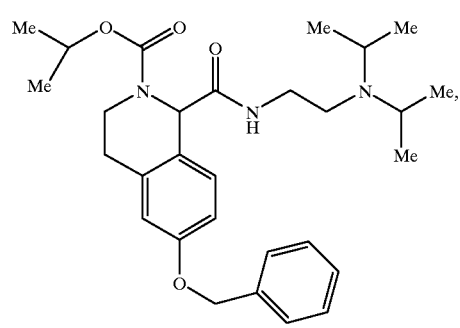
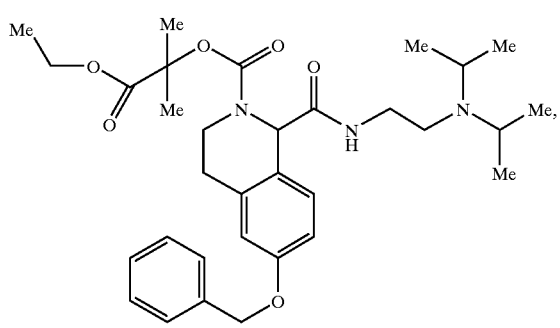

191
-continued
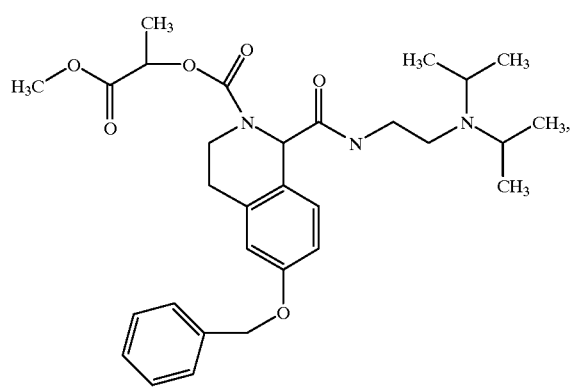
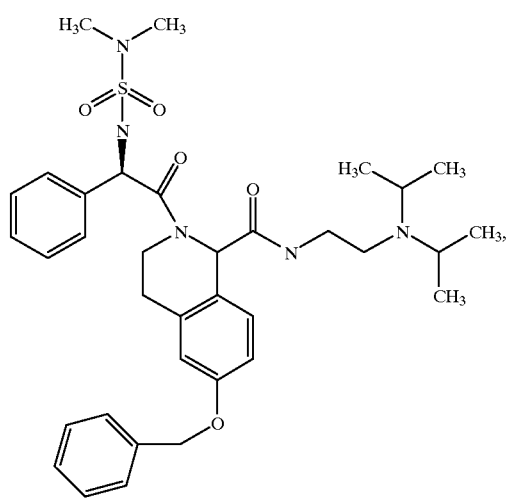
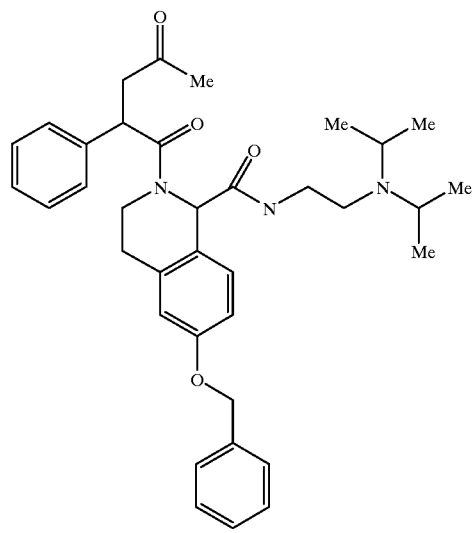
Diastereomer A
192
-continued
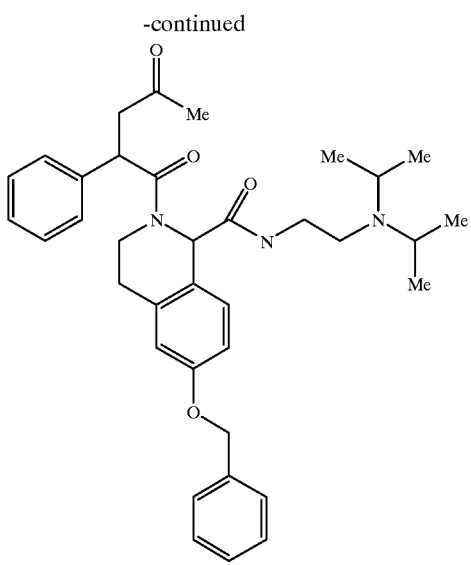
Diastereomer A
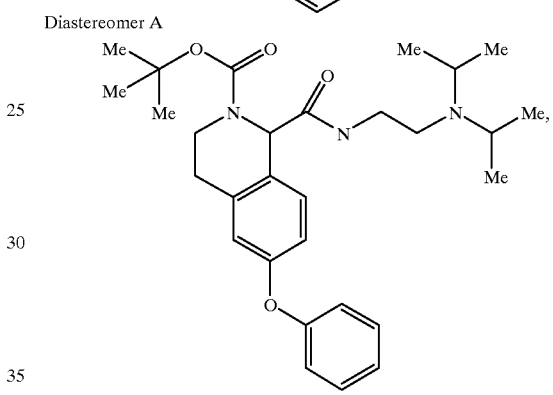
Isomer A
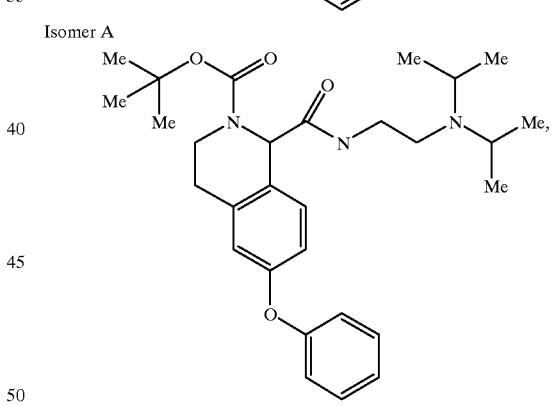
Isomer B
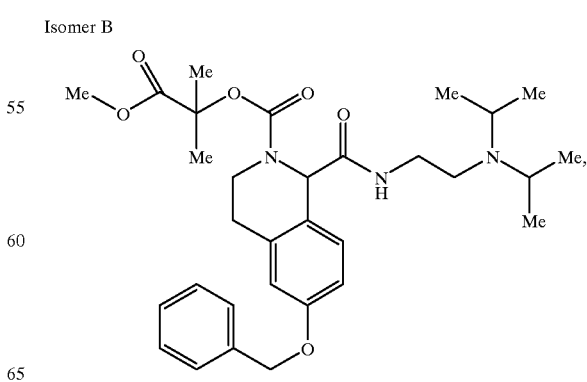

193
-continued
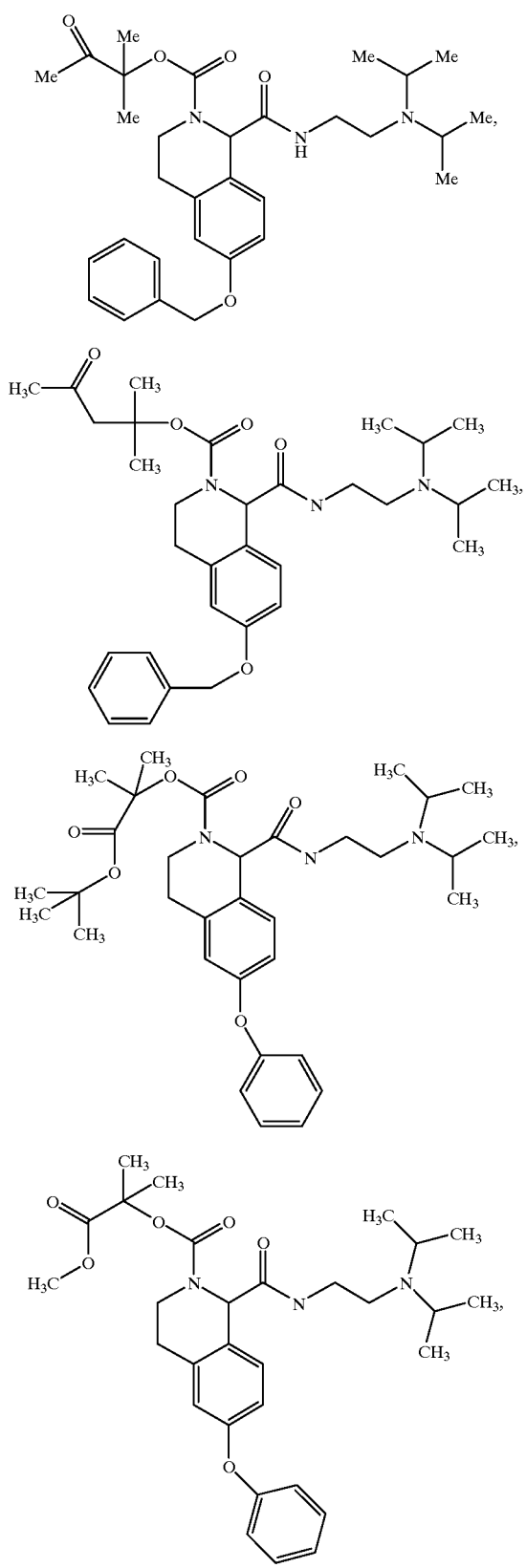
Isomer A
194
-continued
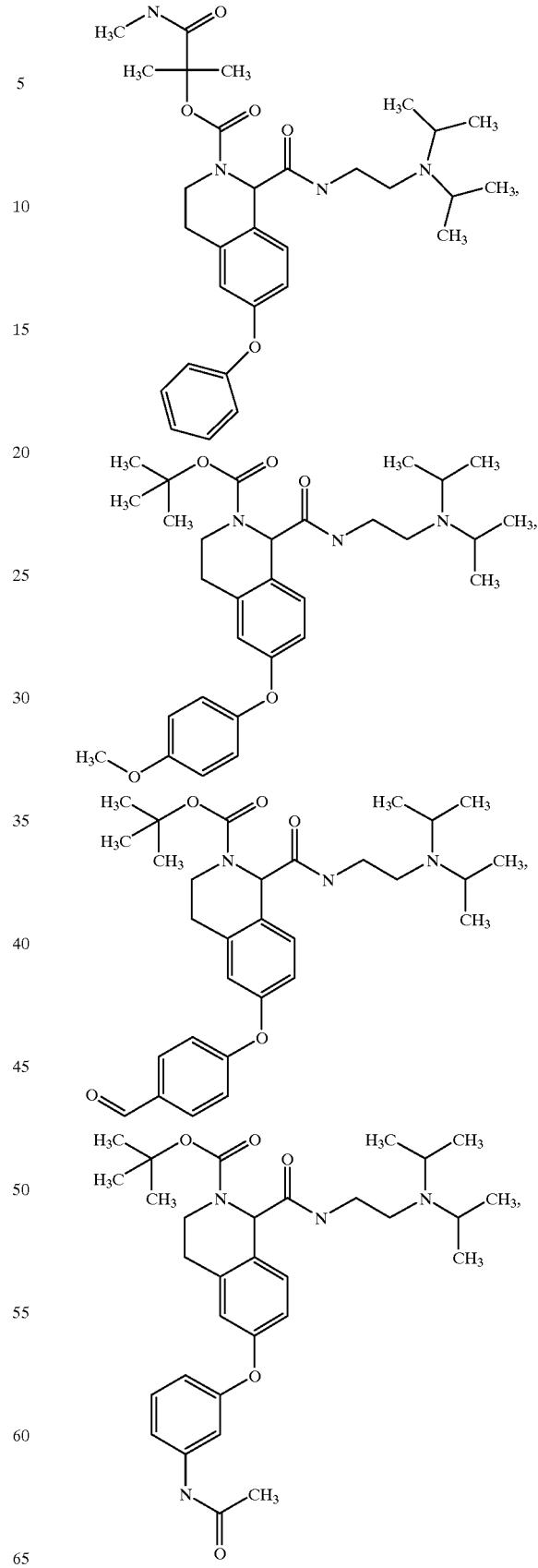

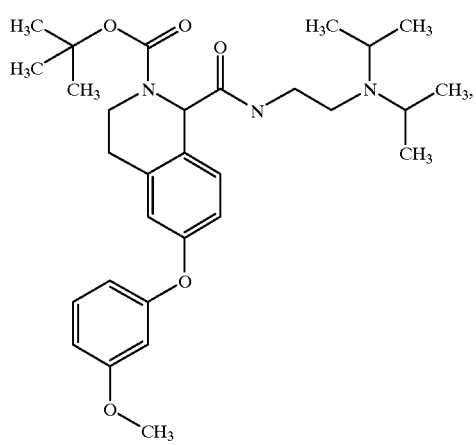
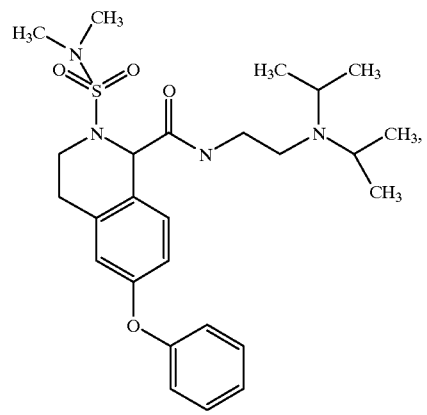
Isomer A
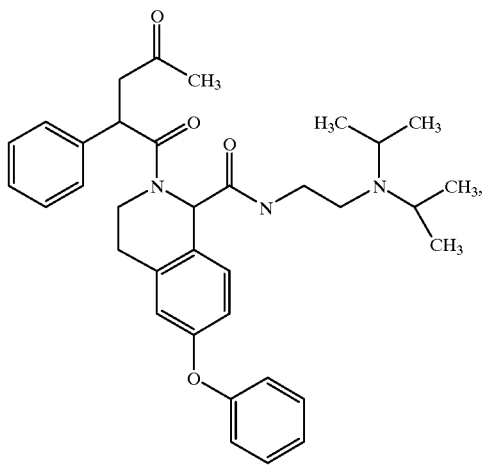
Diastereomer A
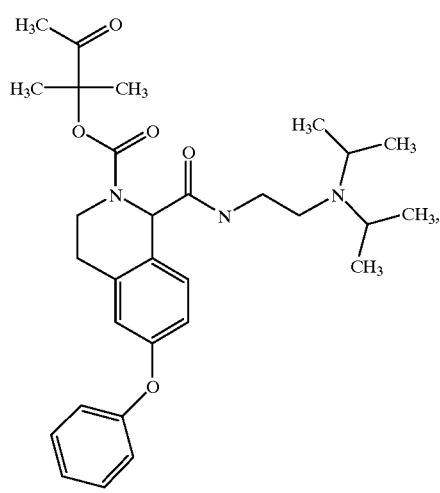
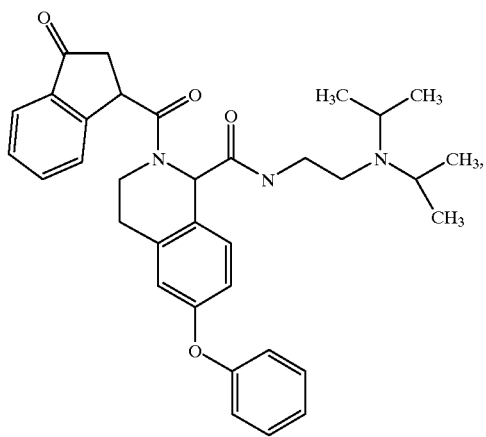
Diastereomer A
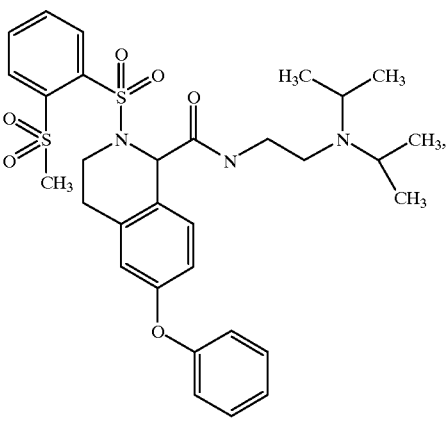

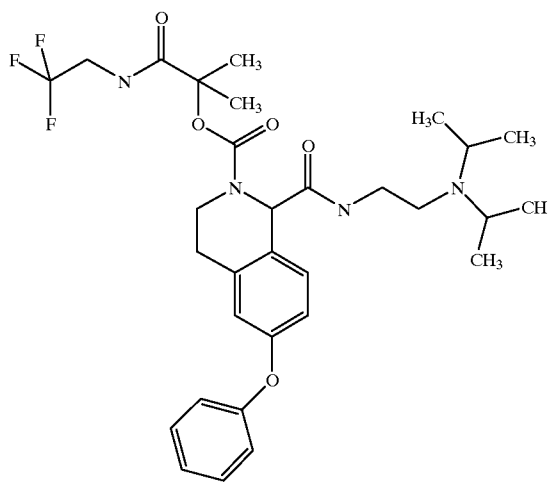
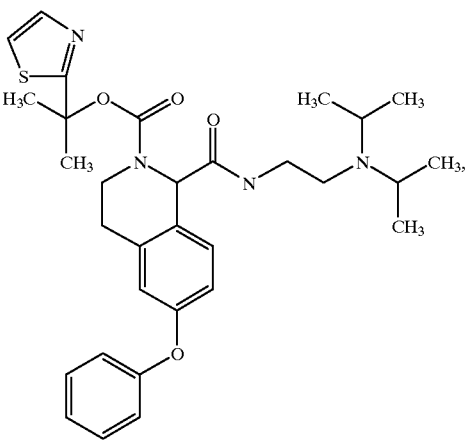
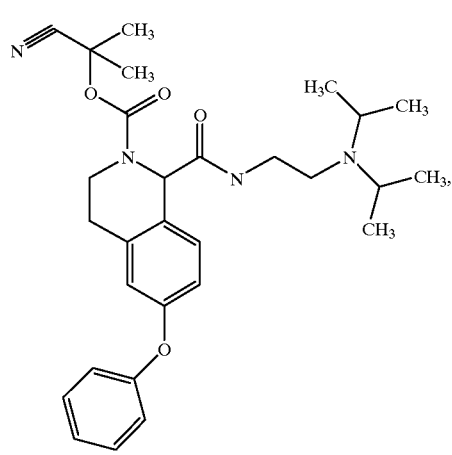
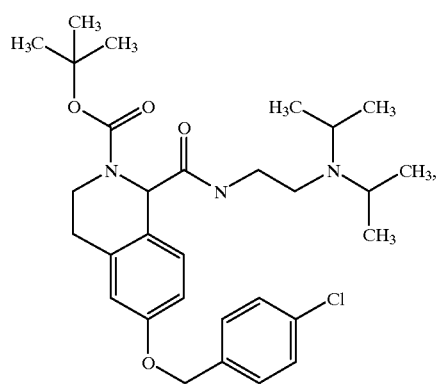
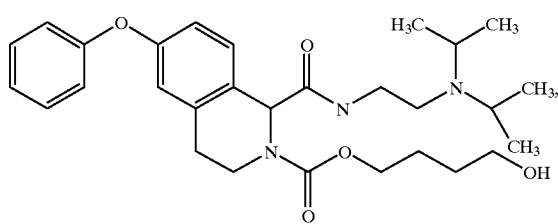
10. The compound as defined in claim 8 having the structure 199
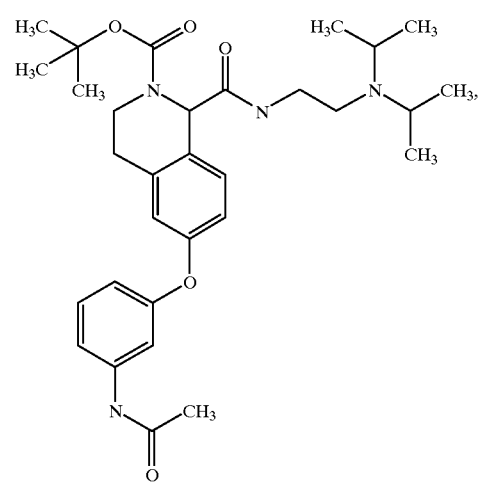
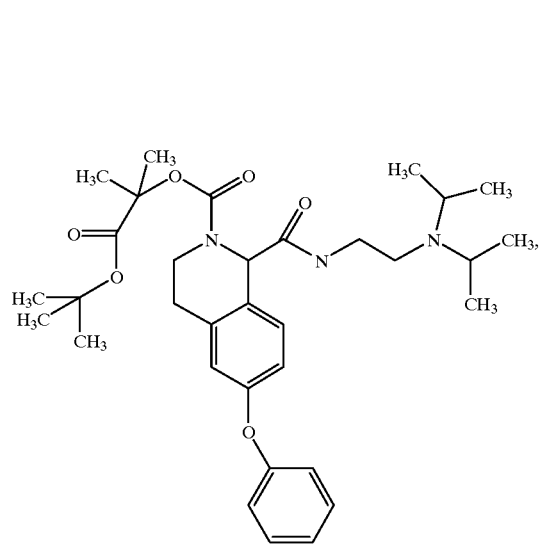
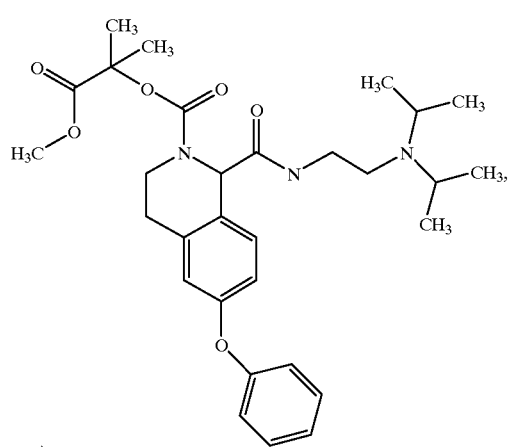
Isomer A
200
-continued
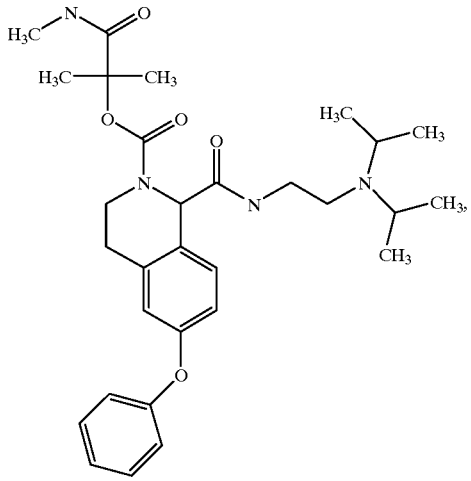
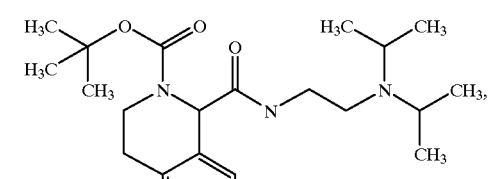
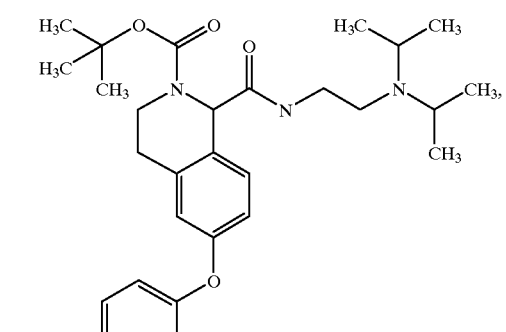
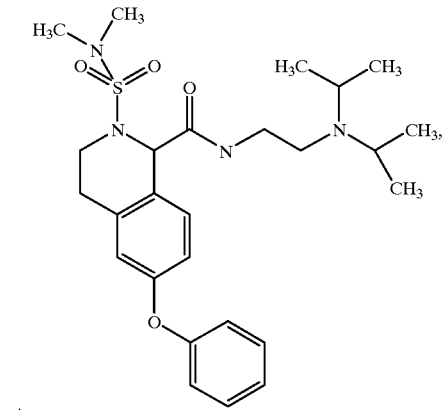
Isomer A 201
-continued
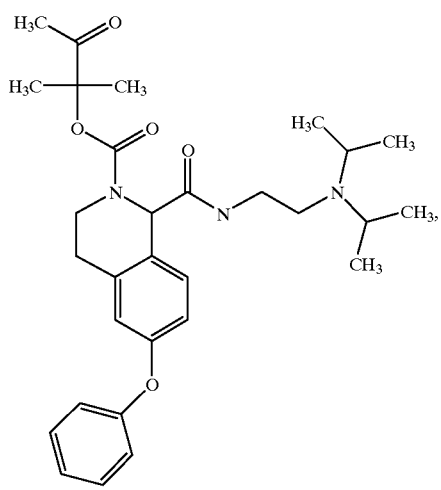
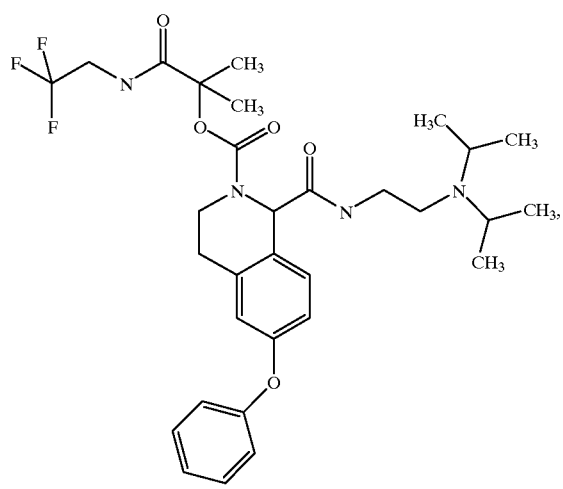
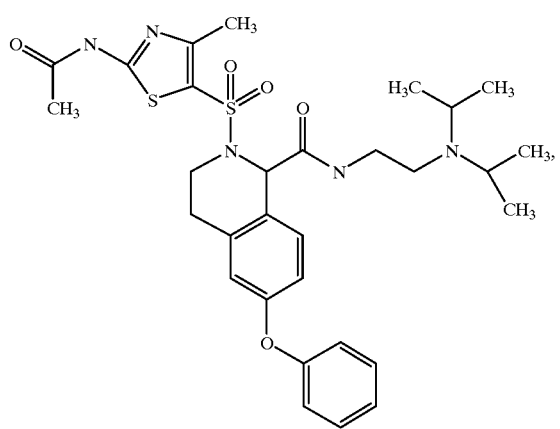
202
-continued
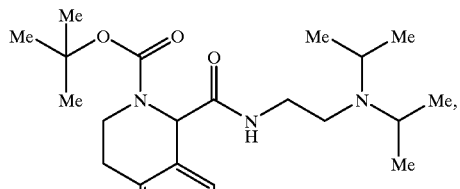
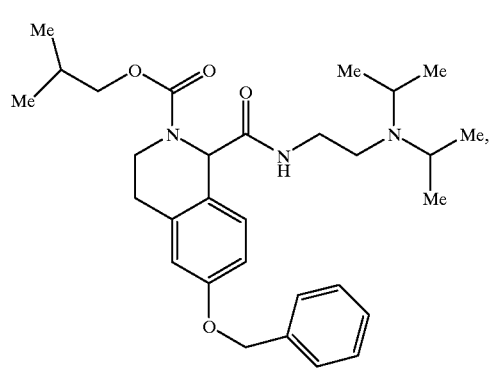
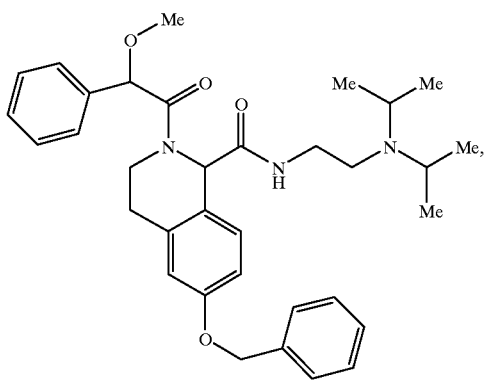
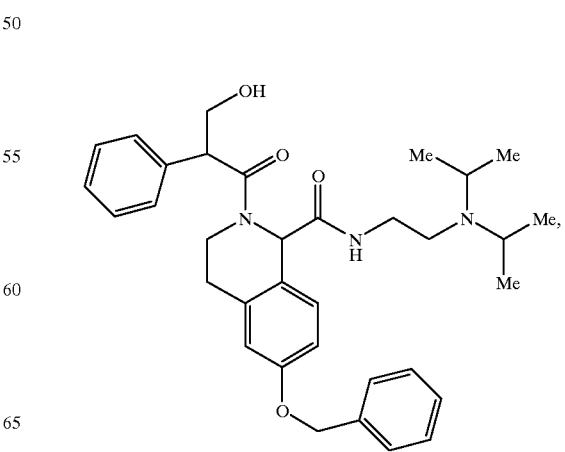

203
-continued
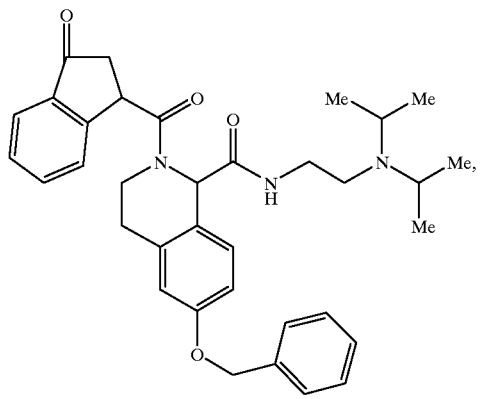
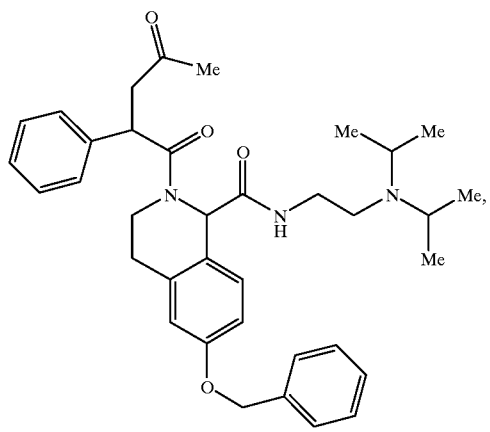
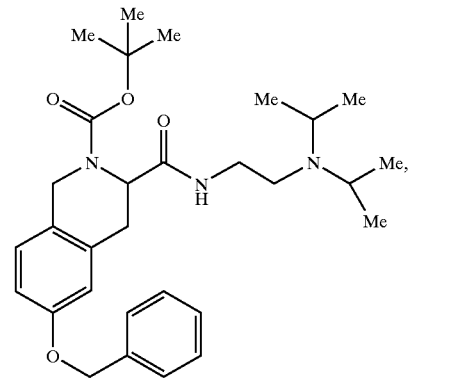
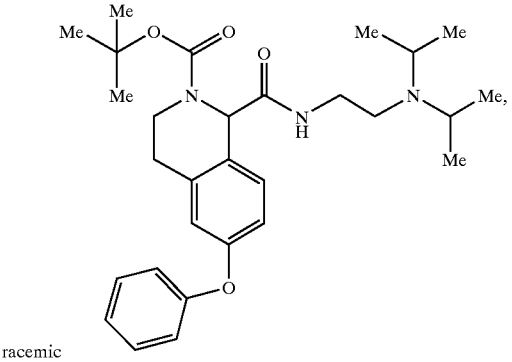
racemic
204
-continued
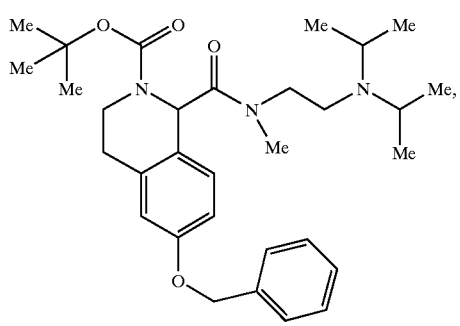
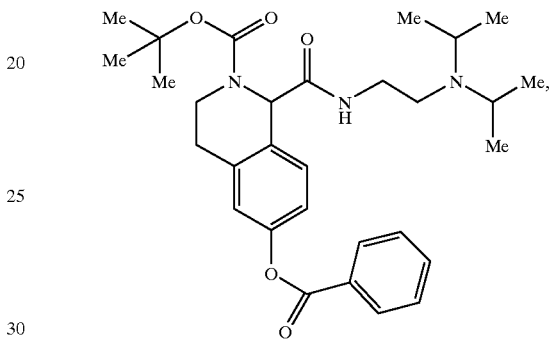
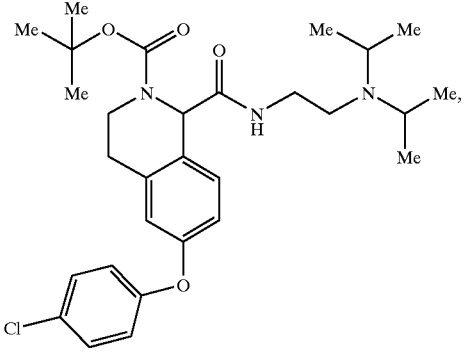
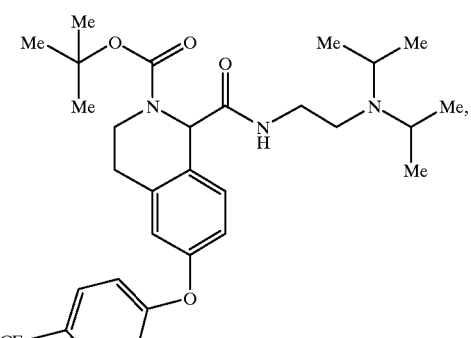

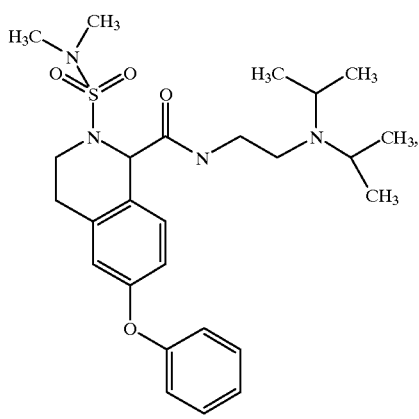
Isomer A
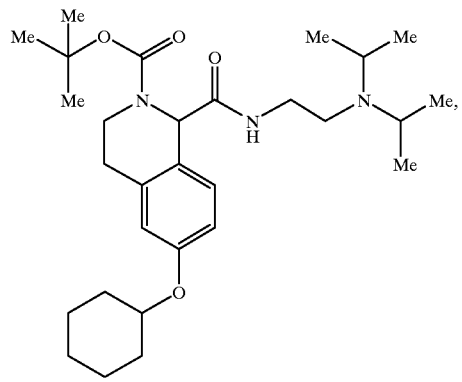
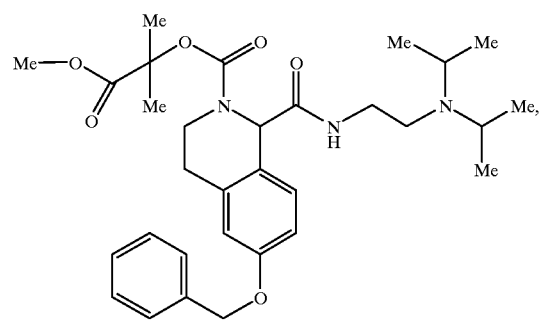
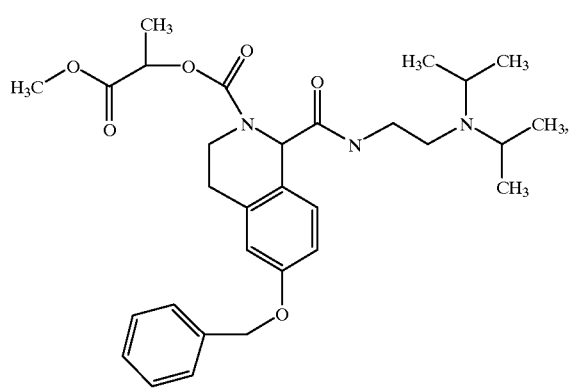
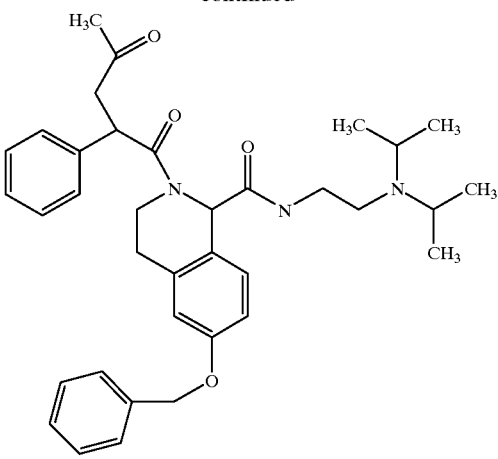
Isomer A
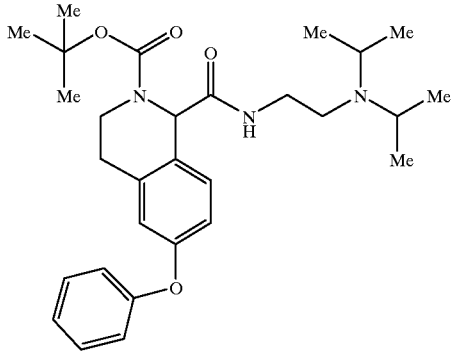
Isomer A
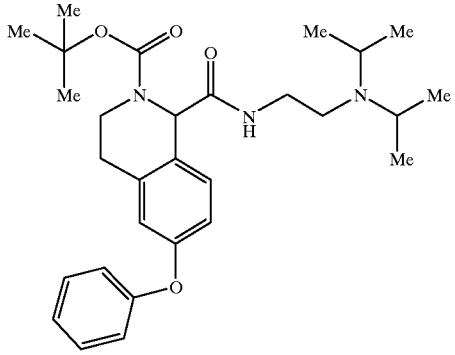
Isomer B
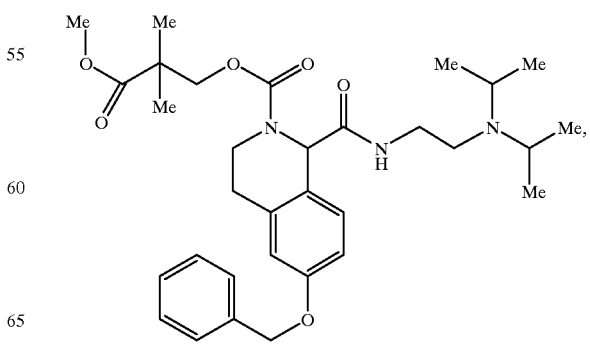

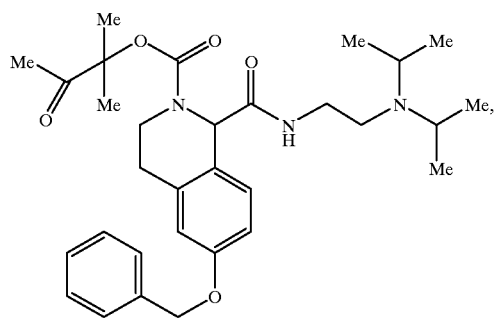

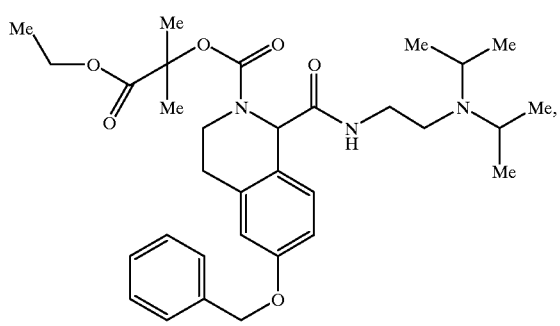

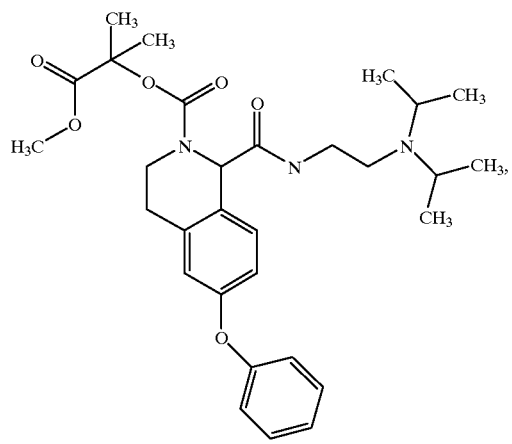

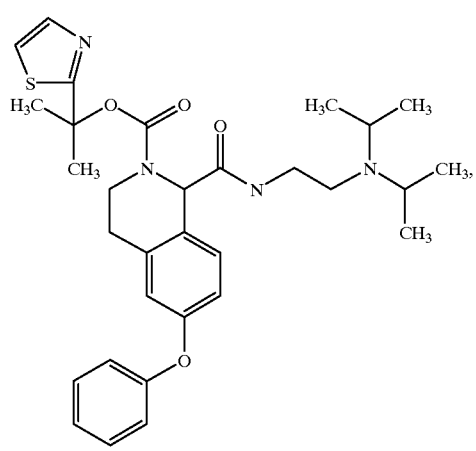

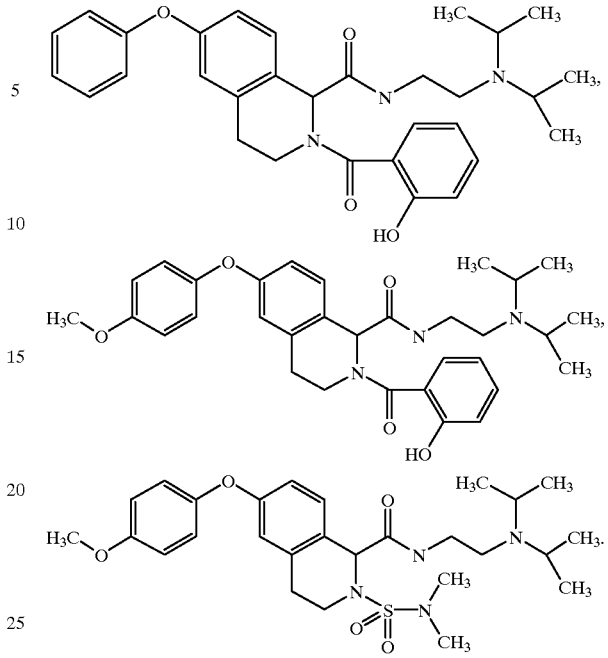

11. A pharmaceutical composition comprising a compound as defined in claim 1 and a pharmaceutically acceptable carrier therefor.

12. A pharmaceutical composition of claim 11 further comprising at least one additional therapeutic agent selected from parathyroid hormone, bisphosphonates, estrogen, testosterone, selective estrogen receptor modulators, selective androgen receptor modulators, progestin receptor agonists, anti-diabetic agents, anti-hypertensive agents, anti-inflammatory agents, anti-osteoporosis agents, anti-obesity agents, cardiac glycosides, cholesterol lowering agents, or thyroid mimetics.

13. A method for increasing levels of endogenous growth hormone, which comprises administering a therapeutically effective amount of a compound as defined in claim 1 to a patient in need thereof.

14. A method for treating obesity which comprises administering a therapeutically effective amount of a compound as defined in claim 1 to a patient in need thereof.

15. A method for treating osteoporosis which comprises administering a therapeutically effective amount of a compound as defined in claim 1 to a patient in need thereof.

16. A method for treating renal disease which comprises administering a therapeutically effective amount of a compound as defined in claim 1 to a patient in need thereof.

17. A method for treating congestive heart failure, cardiac myopathy or cardiac dysfunction associated with valvular disease which comprises administering a therapeutically effective amount of a compound as defined in claim 1 to a patient in need thereof.

18. A method for treating cachexia which comprises administering a therapeutically effective amount of a compound as defined in claim 1 to a patient in need thereof.

19. A method for treating HIV wasting syndrome, muscular atrophy, lipodistrophy, long term critical illness, sarcopenia, stimulating wound healing and/or the immune system, increasing muscle mass and/or strength, maintaining muscle strength and function in the elderly, or treating fraility or ARFD in the elderly which comprises administering a therapeutically effective amount of a compound as defined in claim 1 to a patient in need thereof.

20. A method for treating anorexia which comprises administering a therapeutically effective amount of a compound as defined in claim 1 to a patient in need thereof.

21. A method for treating sleep disorders which comprises administering a therapeutically effective amount of a compound as defined in claim 1 to a patient in need thereof.

22. A method for treating depression which comprises administering a therapeutically effective amount of a compound as defined in claim 1 to a patient in need thereof.

23. A method for improving cognitive function which comprises administering a therapeutically effective amount of a compound as defined in claim 1 to a patient in need thereof.

24. A method for improving the immune response to vaccination which comprises administering a therapeutically effective amount of a compound as defined in claim 1 to a patient in need thereof.

25. A method for accelerating the recovery of hip fracture which comprises administering a therapeutically effective amount of a compound as defined in claim 1 to a patient in need thereof.

26. A method for treating Syndrome X, which comprises administering a therapeutically effective amount of a compound as defined in claim 1 to a patient in need thereof.

27. A method for treating diabetes and/or increasing lean body mass, which comprises administering a therapeutically effective amount of a compound as defined in claim 1 to a patient in need thereof.

28. A pharmaceutical composition of claim 11 further comprising at least one nutritional supplement.

29. A compound of claim 1 having the structure

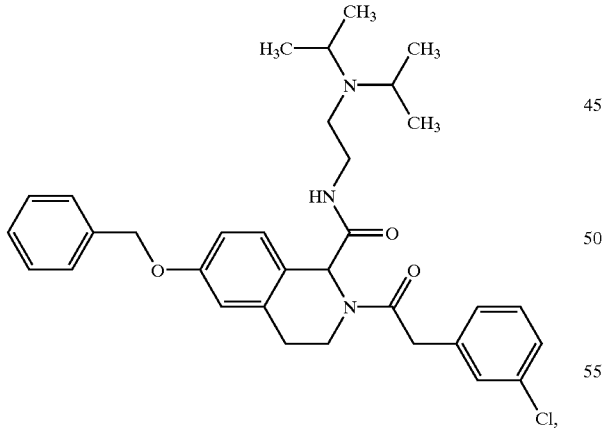

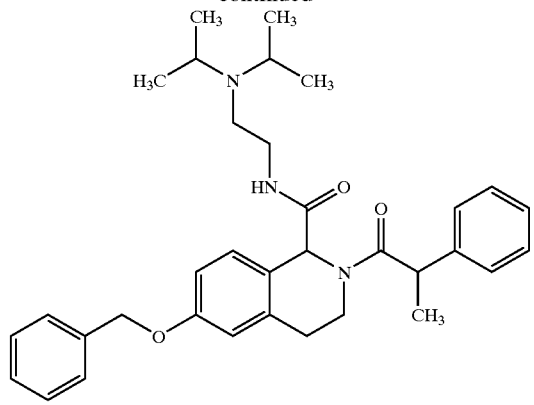

or

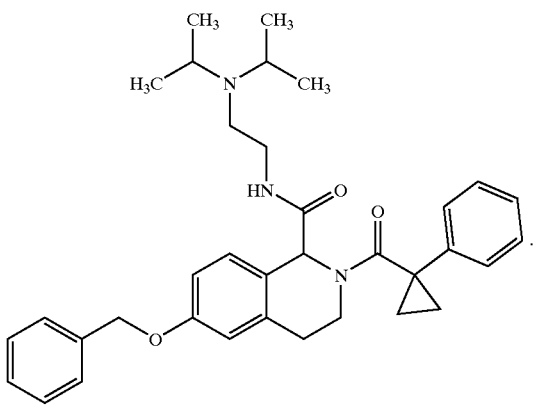

30. A compound of claim 1 having the structure

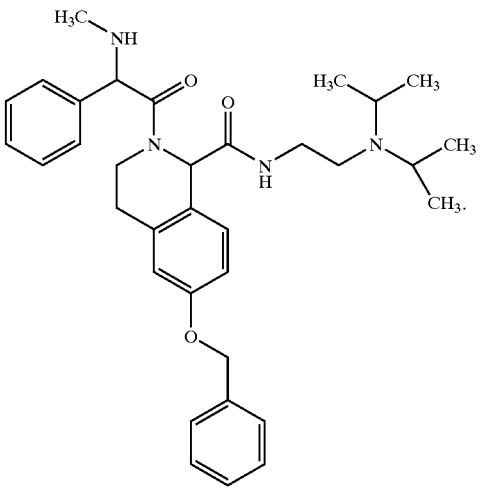

* * * * *